US012180280B2

(12) United States Patent
Li et al.

(10) Patent No.: US 12,180,280 B2
(45) Date of Patent: Dec. 31, 2024

(54) ANTIBODIES BINDING HUMAN AND MONKEY CD3 AND USES THEREOF

(71) Applicant: Beijing Mabworks Biotech Co. Ltd., Beijing (CN)

(72) Inventors: Jiangmei Li, Beijing (CN); Fangjie Liu, Beijing (CN); Chunyang Jin, Beijing (CN); Yu Liu, Beijing (CN); Sijia Huang, Beijing (CN); Feng Li, Beijing (CN)

(73) Assignee: Beijing Mabworks Biotech Co. Ltd., Beijing (CN)

( * ) Notice: Subject to any disclaimer, the term of this patent is extended or adjusted under 35 U.S.C. 154(b) by 0 days.

(21) Appl. No.: 17/460,591

(22) Filed: Aug. 30, 2021

(65) Prior Publication Data
US 2022/0195043 A1    Jun. 23, 2022

(30) Foreign Application Priority Data
Dec. 23, 2020 (CN) .......................... 202011540874.8

(51) Int. Cl.
*C07K 16/28* (2006.01)
*A61P 35/00* (2006.01)
*C07K 16/30* (2006.01)
*A61K 39/00* (2006.01)

(52) U.S. Cl.
CPC .......... *C07K 16/2809* (2013.01); *A61P 35/00* (2018.01); *C07K 16/2887* (2013.01); *A61K 2039/505* (2013.01); *C07K 2317/24* (2013.01); *C07K 2317/31* (2013.01); *C07K 2317/92* (2013.01)

(58) Field of Classification Search
CPC .......................... C07K 16/00; A61K 39/39541
See application file for complete search history.

(56) References Cited

U.S. PATENT DOCUMENTS

| | | | |
|---|---|---|---|
| 2008/0280297 A1* | 11/2008 | Dalla-Favera | G01N 33/57426 435/6.16 |
| 2011/0190157 A1* | 8/2011 | Kipps | C12Q 1/6809 506/17 |
| 2014/0088295 A1 | 3/2014 | Smith et al. | |
| 2019/0359712 A1 | 11/2019 | Takahashi et al. | |
| 2020/0199231 A1 | 6/2020 | Engelberts et al. | |
| 2020/0299408 A1 | 9/2020 | Chen et al. | |

FOREIGN PATENT DOCUMENTS

| | | |
|---|---|---|
| CN | 112062855 A | 12/2020 |
| WO | 2004108158 A1 | 12/2004 |
| WO | 2012162067 A2 | 11/2012 |
| WO | 2015181098 A1 | 12/2015 |
| WO | 2016020309 A1 | 2/2016 |
| WO | 2018041067 A1 | 3/2018 |
| WO | 2018220099 A1 | 12/2018 |
| WO | 2019045856 A1 | 3/2019 |
| WO | 2020156405 A1 | 8/2020 |
| WO | 2020177321 A1 | 9/2020 |
| WO | 2020247871 A2 | 12/2020 |

OTHER PUBLICATIONS

Kearns (Molecular Cancer Therapeutics, vol. 14, No. 7, p. 1625-1636, 2015) (Year: 2015).*
Paul (Fundamental Immunology, 3rd Edition, 1993, pp. 292-295) (Year: 1993).*
Bendig M. M. (Methods: A Companion to Methods in Enzymology, 1995; 8:83-93) (Year: 1995).*
Rudikoff et al. (Proceedings of the National Academy of Sciences USA, vol. 79, p. 1979-1983, 1982) (Year: 1982).*
Panka (Proceedings of the National Academy of Sciences, USA, vol. 85, p. 3080-3084, 1988) (Year: 1988).*
Bonsignori (Cell, vol. 165, p. 449-463, 2016) (Year: 2016).*
Schiffman et al. (The New England Journal of Medicine, Vo. 353, No. 20, p. 2101-2104, 2005) (Year: 2005).*
Cuzick et al. (The Lancet, vol. 361, p. 296-300, 2003) (Year: 2003).*
Hernandez-Ledesma (Peptides, vol. 30, p. 426-430, 2009) (Year: 2009).*
Baxevanis (Expert Opinion: Drug Discovery, vol. 3, No. 4, p. 441-452, 2008) (Year: 2008).*
Komenaka et al., Clinics in Dermatology, 2004, vol. 22, p. 251-265 (Year: 2004).*
Evans et al. (Q. J. Med 1999: 92: 299-307) (Year: 1999).*
CNPIA, International Search Report and Written Opinion of the International Searching Authority, of the counterpart International application PCT/CN2021/115298 mailed Nov. 25, 2021.
Mineko Ogura, et al., Oral treatment with foralumab, a fully human anti-CD3 monoclonal antibody, prevents skin xenograft rejection in humanized mice, Clinical Immunology (2017) 183, p. 240-246.
CNPIA, First Office Action, of the counterpart Chinese Application No. 02011540874.8, Mar. 9, 2023.
EPO, Supplementary European Search Report for the counterpart European Application No. 21908648, Oct. 22, 2024.

* cited by examiner

*Primary Examiner* — Michael Allen
(74) *Attorney, Agent, or Firm* — Duane Morris LLP; Thomas J. Kowalski

(57) ABSTRACT

Disclosed is a monoclonal antibody that binds human and monkey CD3, or an antigen-binding portion thereof, as well as the use of the antibody or antigen-binding portion thereof in treatment of inflammatory diseases and in preparation of bispecific antibodies. A bispecific antibody against e.g., CD3 and CD20 comprising the antibody or antigen-binding portion thereof of the disclosure, and the use of the bispecific antibody in treatment of diseases such as cancers are also provided.

17 Claims, 15 Drawing Sheets
Specification includes a Sequence Listing.

ic patent application 
ANTIBODIES BINDING HUMAN AND MONKEY CD3 AND USES THEREOF

RELATED APPLICATIONS AND INCORPORATION BY REFERENCE

This application claims priority to Chinese Patent Application No. 202011540874.8 filed Dec. 23, 2020.

The foregoing application, and all documents cited therein or during its prosecution ("appln cited documents") and all documents cited or referenced herein (including without limitation all literature documents, patents, published patent applications cited herein) ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference. Any Genbank sequences mentioned in this disclosure are incorporated by reference with the Genbank sequence to be that of the earliest effective filing date of this disclosure.

SEQUENCE STATEMENT

The instant application contains a Sequence Listing, which has been submitted electronically and is hereby incorporated by reference in its entirety. Said ASCII copy, is named 55556_00066SL.txt and is 58 kb in size.

FIELD OF THE INVENTION

The present disclosure relates to an isolated monoclonal antibody, or an antigen-binding portion thereof, that binds to human and monkey CD3ε, and the use of this antibody or antigen-binding portion thereof in treatment or alleviation of an inflammatory disease such as an autoimmune disease, or in reduction or elimination of graft rejection. The disclosure also provides a bispecific antibody comprising the antibody or the antigen-binding portion thereof, which is against e.g., CD3 and CD20, and the use of such a bispecific antibody in treatment of diseases such as cancers.

BACKGROUND OF THE INVENTION

T Cell and CD3

There are two main immunity mechanisms in the adaptive immune system, cellular and humoral. The cellular immunity is mediated by T cells which are borne from hematopoietic stem cells residing in the bone marrow (in some cases extra-embryonic yolk sac and fetal liver). The hematopoietic stem cells differentiate into multipotent progenitors and then common lymphoid progenitors, and migrate to the thymus to mature. The common lymphoid progenitors that survive and leave the thymus become immunocompetent T cells.

Studies have shown that T cell activation, proliferation and differentiation (to effector cells) occur through simultaneous engagements of the T cell receptor (TCR) and the co-stimulatory molecule on T cells such as CD28 respectively with the MHC/peptide complex and co-stimulatory molecules on the antigen presenting cells.

A T cell receptor complex comprises a TCR molecule and a CD3 molecule. A TCR molecule consists of an alpha ($\alpha$) chain and a beta ($\beta$) chain, or a gamma ($\gamma$) chain and a delta ($\delta$) chain. Each chain contains an extracellular variable region responsible for binding the antigenic peptide, an extracellular constant region proximal to the cell membrane, and a short cytoplasmic tail. Due to the short cytoplasmic tail, the TCR requires CD3 to mediate signal transduction. A CD3 molecule is composed of a gamma ($\gamma$) chain, a delta ($\delta$) chain, two epsilon ($\epsilon$) chains, and two zeta ($\zeta$) chains, forming three dimers $\epsilon\gamma$, $\epsilon\delta$ and $\zeta\zeta$ in the TCR/CD3 complex. The CD3$\gamma$, CD3$\delta$, and CD3$\epsilon$ chains are all type I transmembrane proteins of the immunoglobulin superfamily with an immunoglobulin domain, and the intracellular tails of CD3$\gamma$, CD3$\delta$, CD3$\epsilon$ and CD3$\zeta$ chains contain 10 immunoreceptor tyrosine-based activation motifs (ITAM) in total, the phosphorylation of which enables the CD3 chains bind to ZAP70, a kinase important in T cell signaling cascade. The CD3$\epsilon$ chain has an epitope conserved among species to which most anti-CD3 antibodies binds, including Muromonab-CD3 (or OKT3), the first human anti-CD3 antibody (Jones M et al., (1993) *Journal of Immunology* 150(12): 5429-5435).

CD3 Targeting Antibodies

As the CD3 molecule functions to stabilize TCR structure and perform signal transduction, a lot of antibodies against CD3 have been developed to regulate T cell activation signaling, so as to block or at least reduce undesirable immune responses, thus alleviating inflammatory diseases and/or autoimmune diseases. For example, OKT3 has been approved to reduce/eliminate graft rejection and treat/alleviate autoimmune diseases.

An anti-CD3 antibody may form a bispecific molecule with a functional moiety targeting a disease associated antigen such as a tumor associated antigen. The bispecific molecule physically links T cells to disease associated antigens, resulting in activation of T cells around disease associated cells and accordingly T cell-mediated killings of these cells. For instance, a bispecific molecule specific to both the CD3 molecule and a tumor associated antigen may pull T cells closer to the tumor cells, such that the T cells are activated to release supramolecular attack particles (SMAP) containing more than 280 proteins. The SMAPs exocytose granzymes and performs, where the performs form pores on the plasma membrane of target cells that mediate entry of granzymes into the target cell cytoplasm (S. Bálint et al., (2020) Science 368(6493): 897-901).

Adverse Reactions Induced by Anti-CD3 Antibodies

The anti-CD3 activated T cells, while killing tumor cells, secrete cytokines such as IL-2, IFN-$\gamma$ and TNF-$\alpha$ to promote cell proliferation and differentiation. T cell proliferation and differentiation, on one side, generates more T cells to kill tumor cells, and on the other side, causes severe toxicities, i.e., cytokine release syndrome (CRS), in subjects receiving anti-CD3 therapy. Clinical signs and symptoms of CRS include fever, nausea, headache, rash, rapid heartbeat, low blood pressure, and trouble breathing, mild or life threatening. In the clinical trials of Blincyto® blinatumomab, a bispecific T cell engager antibody against CD19 and CD3, severe CRS and neurological toxicities were observed. Specifically, neurological toxicities occurred in about 50% of the subjects receiving the therapy.

Such CRSs observed in the bispecific therapies also occurred in therapies using mono-specific anti-CD3 antibodies such as OKT3, and the CRSs were believed to be related to cross-linking of antibodies through binding to Fc receptors (FcRs) (Herold K C et al., (2003) *J Clin Invest.*

111(3):409-418). Therefore, in subsequent antibody development, the Fc regions of anti-CD3 antibodies such as Teplizumab were engineered to have weak FcR binding capabilities.

However, the modification to the Fc regions of monospecific anti-CD3 antibodies is not applicable to the bispecific anti-CD3 antibodies, as the binding of the disease associated antigen targeting functional moieties to a target cell renders antibody cross-linking, inducing abundant cytokine release by T cells. Thus, it is extremely important to find an anti-CD3 antibody or an antigen-binding portion thereof that has high CD3 binding affinity but causes less cytokine release, for the development and clinical use of bispecific anti-CD3 antibodies.

Bispecific Anti-CD3 Antibodies Targeting CD3 and CD20

CD20 is a B-cell marker expressed on the surface of malignant and non-malignant pre- and mature B cells, but not on hematopoietic stem cells, pro-B cells or normal plasma cells. CD20 shedding or internalization is not observed upon anti-CD20 antibody binding. In this respect, CD20 is a promising antigen for B cell lymphoma and B cell leukemia diagnosis and/or treatment.

Bispecific antibodies targeting both CD3 and CD20 may physically link T cells and CD20 positive tumor cells such as malignant B cells, inducing T cell activation and T cell mediated attacks to CD20 positive B malignancies.

However, as mentioned above, the administration of such antibodies may inevitably cause severe toxicity. In a multi-center, open-label, phase I/Ib trial (NCT02500407) evaluating the safety and pharmacokinetics of Mosunetuzumab, a CD3 and CD20 binding antibody, the CRSs were observed in 28.9% of patients receiving such therapy. In another multi-center, open-label, phase I/Ib trial for evaluating the efficacy, safety, tolerance and pharmacokinetics of CD20-TCB, a T cell engaging bispecific antibody, in treatment of relapsed or refractory (R/R) B cell non-Hodgkin lymphoma (NHL), CRSs occurred in 67.9% of patients.

Therefore, there is an urgent need for bispecific CD3 and CD20 binding antibodies that have potent anti-tumor effects and cause moderate adverse drug reactions. For construction of such bispecific antibodies, CD3 antibodies or antigen-binding portions thereof having high CD3 affinities and inducing less cytokine release are needed, and the way to combine CD3 antibodies and CD20 antibodies should be optimized. The antibodies are expected to provide a better therapeutic window for CD3-CD20 targeting therapies.

Citation or identification of any document in this application is not an admission that such document is available as prior art to the present invention.

SUMMARY OF THE INVENTION

The inventors of the disclosure have found an anti-CD3 antibody or an antigen-binding portion thereof that specifically binds human and monkey CD3ε. Compared to prior art anti-CD3 antibodies, the antibody or antigen-binding portion thereof of the disclosure has comparable, if not higher, human/monkey CD3ε binding capability, and thus provides comparable, if not better, efficacy in treatment of inflammatory diseases and/or auto-immune diseases. More importantly, the antibody or antigen-binding portion thereof the disclosure, while providing comparable or higher CD3 binding capability, induces reduced T cell activation, resulting in less serious side effects. A bispecific antibody using the antibody or antigen-binding portion thereof of the disclosure also produces lower toxicity to bodies.

While not wishing to be bound to any theory, the inventors of the disclosure believe that the CD3ε epitope the antibody or antigen-binding portion thereof of the disclosure binds and/or the configuration of the antibody-antigen-cell complex contributes to the antibody or antigen-binding portion's high CD3ε binding affinity and the reduced cytokine release by T cells. The antibody or antigen-binding portion thereof of the disclosure retains such characteristics when it becomes part of a bispecific antibody against CD3ε and a disease associated antigen such as CD20, i.e., the bispecific antibody shows high killing capability against target cells and causes less cytokine release.

Thus, in a first aspect, the present disclosure provides an isolated monoclonal antibody, for example, a mouse, chimeric or humanized antibody, or an antigen-binding portion thereof, that binds to CD3ε, which may comprise (i) a heavy chain variable region that may comprise a VH CDR1 region, a VH CDR2 region and a VH CDR3 region, wherein the VH CDR1 region, the VH CDR2 region and the VH CDR3 region may comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 1 (X1=S), 2 (X1=D) and 3 (X1=L, X2=Y), respectively; (2) SEQ ID NOs: 1 (X1=T), 2 (X1=I) and 3 (X1=L, X2=Y), respectively; (3) SEQ ID NOs: 1 (X1=T), 2 (X1=D) and 3 (X1=I, X2=W), respectively; or (4) SEQ ID NOs: 1 (X1=T), 2 (X1=I) and 3 (X1=I, X2=Y), respectively; and/or (ii) a light chain variable region that may comprise a VL CDR1 region, a VL CDR2 region and a VL CDR3 region, wherein the VL CDR1 region, the VL CDR2 region and the VL CDR3 region may comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 4 (X1=D, X2=S), 5 (X1=Q, X2=R, X3=S) and 6 (X1=V), respectively; (2) SEQ ID NOs: 4 (X1=Q, X2=N), 5 (X1=K, X2=Q, X3=R) and 6 (X1=V), respectively; (3) SEQ ID NOs: 4 (X1=K, X2=S), 5 (X1=N, X2=L, X3=H) and 6 (X1=A), respectively; or (4) SEQ ID NOs: 4 (X1=R, X2=N), 5 (X1=R, X2=L, X3=S) and 6 (X1=V), respectively.

The antibody or the antigen-binding portion thereof of the present disclosure may comprise a heavy chain variable region having a VH CDR1 region, a VH CDR2 region and a VH CDR3 region, and a light chain variable region having a VL CDR1 region, a VL CDR2 region and a VL CDR3 region, wherein the VH CDR1, VH CDR2, VH CDR3, VL CDR1, VL CDR2 and VL CDR3 may comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 1 (X1=S), 2 (X1=D), 3 (X1=L, X2=Y), 4 (X1=D, X2=S), 5 (X1=Q, X2=R, X3=S) and 6 (X1=V), respectively; (2) SEQ ID NOs: 1 (X1=T), 2(X1=I), 3 (X1=L, X2=Y), 4 (X1=Q, X2=N), 5 (X1=K, X2=Q, X3=R) and 6 (X1=V), respectively; (3) SEQ ID NOs: 1 (X1=T), 2 (X1=D), 3 (X1=I, X2=W), 4 (X1=K, X2=S), 5 (X1=N, X2=L, X3=H) and 6 (X1=A), respectively; or (4) SEQ ID NOs: 1 (X1=T), 2 (X1=I), 3 (X1=I, X2=Y), 4 (X1=R, X2=N), 5 (X1=R, X2=L, X3=S) and 6 (X1=V), respectively.

The heavy chain variable region may comprise an amino acid sequence having at least 85%, 86%, 87%, 88%, 89%, 90%, 91%, 92%, 93%, 94%, 95%, 96%, 97%, 98%, 99% or 100% identity to any one of SEQ ID NOs: 7-14.

The light chain variable region may comprise an amino acid sequence having at least 85%, 86%, 87%, 88%, 89%, 90%, 91%, 92%, 93%, 94%, 95%, 96%, 97%, 98%, 99% or 100% identity to any one of SEQ ID NOs: 15-21.

The antibody or the antigen-binding portion thereof of the present disclosure may comprise a heavy chain variable region and a light chain variable region, the heavy chain variable region and the light chain variable region may comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 7 and 15, respectively; (2) SEQ ID NOs: 8 and 16, respectively; (3) SEQ ID NOs: 9 and 17, respectively; (4) SEQ ID NOs: 9 and 18, respectively; (5) SEQ ID NOs: 10 and 17, respectively; (6) SEQ ID NOs: 10 and 18, respectively; (7) SEQ ID NOs: 11 and 19, respectively; (8) SEQ ID NOs: 12 and 20, respectively; (9) SEQ ID NOs: 13 and 20, respectively; or (10) SEQ ID NOs: 14 and 21, respectively.

The antibody or the antigen-binding portion thereof of the present disclosure may comprise a heavy chain constant region and/or a light chain constant region. In certain embodiments, the antibody or antigen-binding portion thereof contains a heavy chain constant region with reduced/weak FcR binding affinity, and/or a light chain constant region. In certain embodiments, the antibody or antigen-binding portion thereof contains a heavy chain constant region with no FcR binding affinity, and/or a light chain constant region. The heavy chain constant region with weak or no FcR binding affinity may be human IgG1 (N297A), human IgG1 (L234A+L235A) having the amino acid sequence of e.g., SEQ ID NO: 22 (X1=A, X2=A, X3=N, X4=P), human IgG1 (L234A+L235A+P329G) having the amino acid sequence of e.g., SEQ ID NO: 22 (X1=A, X2=A, X3=N, X4=G), human IgG1 (L234A+L235A+N297A) having the amino acid sequence of e.g., SEQ ID NO: 22 (X1=A, X2=A, X3=A, X4=P), human IgG1 (L234A+L235A+N297A+P329G) having the amino acid sequence of e.g., SEQ ID NO: 22 (X1=A, X2=A, X3=A, X4=G), human IgG2 (V234A+V237A), human IgG1 (L234A+V235E) heavy chain constant region, or a functional fragment thereof. The light chain constant region may be κ or λ light chain constant region, such as human κ or λ light chain constant region having the amino acid sequence of SEQ ID NOs: 23 or 32, or a functional fragment thereof.

The antibody or the antigen-binding portion thereof of the present disclosure may be a single chain variable fragment (scFv) antibody, or antibody fragments, such as Fab or F(ab')$_2$ fragments.

The disclosure also provides a bispecific molecule that may comprise the antibody, or the antigen-binding portion thereof, of the disclosure, linked to a second functional moiety (e.g., a second antibody) having a different binding specificity than said antibody, or antigen-binding portion thereof, e.g., a second functional moiety against a disease associated antigen.

The bispecific molecule may target CD3ε and a disease associated antigen. In certain embodiments, the disease associated antigen is a tumor associated antigen, such as CD20, CD19, CD22, CD4, CD24, CD38, CD123, CD228, CD138, BCMA, GPC3, CEA, CD276, gp100, 5T4, GD2, EGFR, MUC-1, PSMA, EpCAM, MCSP, SM5-1, MICA, MICB, ULBP and HER-2. In certain embodiments, the disease associated antigen is an infectious disease associated antigen such as CD4, BHsAg, LMP-1 and LMP2. In certain embodiments, the disease associated antigen is an inflammatory disease associated antigen such as IL17R and CD6. In certain embodiments, the disease associated antigen is CD20.

The bispecific molecule may be a recombinant protein containing two antigen binding domains linked via a linker. In certain embodiments, the two binding domains may be linked with or without a linker in e.g., scFv-scFv, Fab-Fab or scFv-Fab formats.

The bispecific molecule of the disclosure may be a bispecific antibody targeting CD3 and CD20, containing a CD3ε binding domain and a CD20 binding domain.

The bispecific antibody may contain one CD3ε binding domain, and one to five CD20 binding domains. In one embodiment, the bispecific antibody may contain one CD3ε binding domain, and two CD20 binding domains. In one embodiment, the CD20 binding domain is an antibody or an antigen-binding portion thereof, e.g., an Fv and/or a scFv, specific to CD20. In one embodiment, the CD3 binding domain may be the anti-CD3 antigen or antigen-binding portion thereof, e.g., an Fv, of the disclosure. The two CD20 binding domains may bind to the same or different antigen epitopes, may contain the same or different domain sequences, and/or may have the same or different antigen-binding domain formats.

In one embodiment, the CD3 binding domain may contain the CDR regions, the heavy chain variable region and the light chain variable region of the disclosure. In one embodiment, the CD20 binding domain contains 1) a heavy chain variable region having the amino acid sequence of SEQ ID NO: 26, and 2) a light chain variable region having the amino acid sequence of SEQ ID NO: 27.

The bispecific antibody of the disclosure targeting CD3 and CD20 may be an IgG like antibody.

In one embodiment, the bispecific antibody may comprise:
  i) a first polypeptide, containing an anti-CD20 heavy chain variable region and a heavy chain constant region,
  ii) a second polypeptide, containing an anti-CD20 light chain variable region,
  iii) a third polypeptide, containing an anti-CD20 heavy chain variable region, an anti-CD20 light chain variable region, an anti-CD3ε heavy chain variable region, and a heavy chain constant region, and
  iv) a fourth polypeptide, containing an anti-CD3ε light chain variable region,
  wherein the anti-CD20 heavy chain variable region in the first polypeptide and the anti-CD20 light chain variable region in the second polypeptide associate to form an antigen binding fragment against CD20, the anti-CD20 heavy chain variable region and the anti-CD20 light chain variable region in the third polypeptide associate to form an antigen binding fragment against CD20, the anti-CD3ε heavy chain variable region in the third polypeptide and the anti-CD3ε light chain variable region in the fourth polypeptide associate to form an antigen binding fragment against CD3ε, and the heavy chain constant region in the first polypeptide and the heavy chain constant region in the third polypeptide are associated together via e.g., the knob-into-hole approach, the covalent bond or the disulfide bond.

The heavy chain constant region in the first polypeptide may be a heavy chain constant region with a knob, such as human IgG1 heavy chain constant region or a functional fragment thereof with T366W mutation. The heavy chain constant region in the first polypeptide may be a heavy chain constant region with a knob and weak or no FcR binding affinity, such as human IgG1 heavy chain constant region having the amino acid sequence of SEQ ID NO: 34. The heavy chain constant region in the third polypeptide may be a heavy chain constant region with a hole, such as human IgG1 heavy chain constant region or a functional fragment thereof with T366S/L368A/Y407V mutations. The heavy chain constant region in the third polypeptide may be a heavy chain constant region with a hole and weak or no FcR binding affinity, such as human IgG1 heavy chain constant region having the amino acid sequence of SEQ ID NO: 33.

Alternatively, the heavy chain constant region in the first polypeptide may be a heavy chain constant region with a hole, such as human IgG1 heavy chain constant region or a functional fragment thereof with T366S/L368A/Y407V mutations. The heavy chain constant region in the first polypeptide may be a heavy chain constant region with a hole and weak or no FcR binding affinity, such as human IgG1 heavy chain constant region having the amino acid sequence of SEQ ID NO: 33. The heavy chain constant region in the third polypeptide may be a heavy chain constant region with a knob, such as human IgG1 heavy chain constant region or a functional fragment thereof with T366W mutation. The heavy chain constant region in the third polypeptide may be a heavy chain constant region with a knob and weak or no FcR binding affinity, such as human IgG1 heavy chain constant region having the amino acid sequence of SEQ ID NO: 34.

The anti-CD20 heavy chain variable region and the anti-CD20 light chain variable region in the third polypeptide may be linked with a linker. In one embodiment, the linker may be a peptide of about 5 to 30 amino acid residues. In one embodiment, the linker may be a peptide of about 10 to 30 amino acid residues. In one embodiment, the linker may be a peptide of about 10 to 15 amino acid residues. In one embodiment, the linker may be a GS linker having the amino acid sequence of e.g., SEQ ID NO: 28.

The anti-CD20 heavy chain variable region or the anti-CD20 light chain variable region in the third polypeptide may be linked via a linker to the anti-CD3ε heavy chain variable region. In one embodiment, the linker may be a peptide of about 5 to 30 amino acid residues. In one embodiment, the linker may be a peptide of about 10 to 30 amino acid residues. In one embodiment, the linker may be a peptide of about 10 to 15 amino acid residues. In one embodiment, the linker may be a GS linker having the amino acid sequence of e.g., SEQ ID NO: 28.

In one embodiment, the first polypeptide comprises, from N terminus to C terminus, the anti-CD20 heavy chain variable region and the heavy chain constant region. In one embodiment, the third polypeptide comprises, from N terminus to C terminus, the anti-CD20 heavy chain variable region, the anti-CD20 light chain variable region, the anti-CD3ε heavy chain variable region, and the heavy chain constant region; or alternatively the anti-CD20 light chain variable region, the anti-CD20 heavy chain variable region, the anti-CD3ε heavy chain variable region, and the heavy chain constant region. The heavy chain constant region in the first polypeptide may be with a knob, and the heavy chain constant region in the third polypeptide may be with a hole.

In one embodiment, the third polypeptide comprises, from N terminus to C terminus, the anti-CD20 heavy chain variable region, a linker, the anti-CD20 light chain variable region, a linker, the anti-CD3ε heavy chain variable region, and the heavy chain constant region. The third polypeptide may contain the amino acid sequence of SEQ ID NOs: 29 or 30.

The bispecific antibody may contain a light chain constant region at the C terminus of the anti-CD20 light chain variable region in the fourth polypeptide. The light chain constant region may be human λ light chain constant region such as one having the amino acid sequence of SEQ ID NO: 31.

In another embodiment, the bispecific antibody may contain:
i) a first polypeptide, containing an anti-CD20 heavy chain variable region and a heavy chain constant region,
ii) a second polypeptide, containing an anti-CD20 light chain variable region,
iii) a third polypeptide, containing an anti-CD3ε heavy chain variable region, and a heavy chain constant region, and
iv) a fourth polypeptide, containing an anti-CD20 heavy chain variable region, an anti-CD20 light chain variable region, and an anti-CD3ε light chain variable region, wherein the anti-CD20 heavy chain variable region in the first polypeptide and the anti-CD20 light chain variable region in the second polypeptide associate to form an antigen binding fragment against CD20, the anti-CD3ε heavy chain variable region in the third polypeptide and the anti-CD3ε light chain variable region in the fourth polypeptide associate to form an antigen binding fragment against CD3ε, the anti-CD20 heavy chain variable region and the anti-CD20 light chain variable region in the fourth polypeptide associate to form an antigen binding fragment against CD20, and the heavy chain constant region in the first polypeptide and the heavy chain constant region in the third polypeptide are associated together via e.g., the knob-into-hole approach, the covalent bond or the disulfide bond.

In one embodiment, the first polypeptide comprises, from N terminus to C terminus, the anti-CD20 heavy chain variable region and the heavy chain constant region. In one embodiment, the third polypeptide comprises, from N terminus to C terminus, the anti-CD3ε heavy chain variable region, and the heavy chain constant region. In one embodiment, the fourth polypeptide comprises, from N terminus to C terminus, the anti-CD20 heavy chain variable region, the anti-CD20 light chain variable region and the anti-CD3ε light chain variable region; the anti-CD20 light chain variable region, the anti-CD20 heavy chain variable region, and the anti-CD3ε light chain variable region; the anti-CD3ε light chain variable region, the anti-CD20 light chain variable region, and the anti-CD20 heavy chain variable region; or alternatively the anti-CD3ε light chain variable region, the anti-CD20 heavy chain variable region, and the anti-CD20 light chain variable region.

With respect to the heavy chain constant regions in the first and third polypeptides, one is a heavy chain constant region with a knob, such as human IgG1 heavy chain constant region or a functional fragment thereof with T366W mutation, e.g., human IgG1 heavy chain constant region with a knob and weak or no FcR binding affinity having the amino acid sequence of SEQ ID NO: 34, the other is a heavy chain constant region with a hole, such as human IgG1 heavy chain constant region or a functional fragment thereof with T366S/L368A/Y407V mutations, e.g., human IgG1 heavy chain constant region with a hole and weak or no FcR binding affinity having the amino acid sequence of SEQ ID NO: 33.

The anti-CD20 heavy chain variable region and the anti-CD20 light chain variable region in the fourth polypeptide may be linked via a linker. The anti-CD20 heavy chain variable region or the anti-CD20 light chain variable region in the fourth polypeptide may be linked via a linker to the anti-CD3ε light chain variable region. In one embodiment, the linker may be a peptide of about 5 to 30 amino acid residues. In one embodiment, the linker may be a peptide of about 10 to 30 amino acid residues. In one embodiment, the linker may be a peptide of about 10 to 15 amino acid residues. In one embodiment, the linker may be a GS linker having the amino acid sequence of e.g., SEQ ID NO: 28.

The bispecific antibody may contain a light chain constant region at the C terminus of the fourth polypeptide. For example, the bispecific antibody may contain a light chain constant region at the C terminus of the anti-CD3ε light chain variable region, the anti-CD20 heavy chain variable region, or the anti-CD20 light chain variable region. In one embodiment, the bispecific antibody contains a light chain constant region at the C terminus of anti-CD3ε light chain variable region, which may be human λ light chain constant region such as one having the amino acid sequence of SEQ ID NOs: 32 or 23.

The bispecific antibody of the disclosure targeting CD3 and CD20 has higher CD3 binding activity and comparable target cell killing activity, but causes cytokine release at a lower level, as compared to prior art antibodies such as CD20-TCB.

Nucleic acid molecules encoding the antibody or the antigen-binding portion thereof or the bispecific molecule of the disclosure are also encompassed by the disclosure, as well as expression vectors that may comprise such nucleic acids and host cells that may comprise such expression vectors. A method for preparing the anti-CD3 antibody (including the bispecific antibody) or the antigen-binding portion thereof of the disclosure using the host cell is also provided, that may comprise steps of (i) expressing the antibody or the antigen-binding portion thereof in the host cell and (ii) isolating the antibody or the antigen-binding portion thereof from the host cell or its cell culture.

Pharmaceutical compositions that may comprise the antibody or the antigen-binding portion thereof, the bispecific molecule, the nucleic acid molecule, the expression vector, or the host cell of the disclosure, and a pharmaceutically acceptable carrier, are also provided.

In a second aspect, the present disclosure provides the use of the anti-CD3 antibody or antigen-binding portion thereof in preparation of a bispecific molecule targeting both CD3 and a disease associated antigen.

The disease associated antigen may be a tumor associated antigen, such as CD20, CD19, CD22, CD4, CD24, CD38, CD123, CD228, CD138, BCMA, GPC3, CEA, CD276, gp100, 5T4, GD2, EGFR, MUC-1, PSMA, EpCAM, MCSP, SM5-1, MICA, MICB, ULBP and HER-2. The disease associated antigen may be an infectious disease associated antigen such as CD4, BHsAg, LMP-1 and LMP2. The disease associated antigen may be an inflammatory disease associated antigen such as IL17R and CD6. In certain embodiments, the disease associated antigen is CD20.

The bispecific molecule may be a recombinant protein containing two antigen binding domains linked via a linker. In certain embodiments, the two binding domains may be linked with or without a linker in e.g., scFv-scFv, Fab-Fab or scFv-Fab formats. In certain embodiments, the bispecific molecule is an IgG like antibody. In one embodiment, the bispecific antibody contains one CD3ε binding domain, and two CD20 binding domains. In one embodiment, the CD20 binding domain is an antibody or an antigen-binding portion thereof, e.g., an Fv and/or a scFv, specific to CD20. In one embodiment, the CD3 binding domain may be the anti-CD3 antigen or antigen-binding portion thereof, e.g., an Fv, of the disclosure.

Accordingly, the disclosure provides a method for preparing the bispecific molecule of the disclosure, comprising (i) expressing the bispecific molecule in a host cell containing a nucleic acid encoding the bispecific molecule or its functional moieties, and (ii) isolating the bispecific molecule or its functional moieties from the host cell or its cell culture.

In a third aspect, the present disclosure provides a method for treating or alleviating an inflammatory disease, or reducing or eliminating graft rejection in a subject in need thereof, comprising administering to the subject a pharmaceutically effective amount of the anti-CD3 antibody or antigen-binding portion thereof of the disclosure. In certain embodiments, the inflammatory disease is multiple sclerosis (MS) or inflammatory bowel disease (IBD, such as Crohn's disease). In certain embodiments, the auto-immune disease is type I diabetes. In certain embodiments, the anti-CD3 antibody or antigen-binding portion thereof of the disclosure is orally administered.

In a fourth aspect, the present disclosure provides a method for treating or alleviating a disease in a subject in need thereof, comprising administering to the subject a pharmaceutically effective amount of the bispecific molecule of the disclosure. In certain embodiments, the disease is a tumor. In certain embodiments, the disease is an infectious disease. In certain embodiments, the disease is an inflammatory disease or an auto-immune disease.

The disclosure provides a method for treating or alleviating a B cell associated disease in a subject in need thereof, comprising administering to the subject a pharmaceutically effective amount of the bispecific antibody of the disclosure against CD3 and CD20. The B cell associated disease may be B-cell lymphomas, B-cell leukemia, or a B-cell mediated auto-immune disease. The B-cell lymphomas and the B-cell leukemia include, but not limited to, non-Hodgkin's lymphoma (NHL), chronic lymphocytic leukemia (CLL), and diffuse large B-cell lymphoma (DLBCL). In certain embodiments, the subject is administered with an anti-CD20 antibody prior to the bispecific antibody treatment.

Other features and advantages of the instant disclosure will be apparent from the following detailed description and examples, which should not be construed as limiting. The contents of all references, Genbank entries, patents and published patent applications cited throughout this application are expressly incorporated herein by reference.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1:
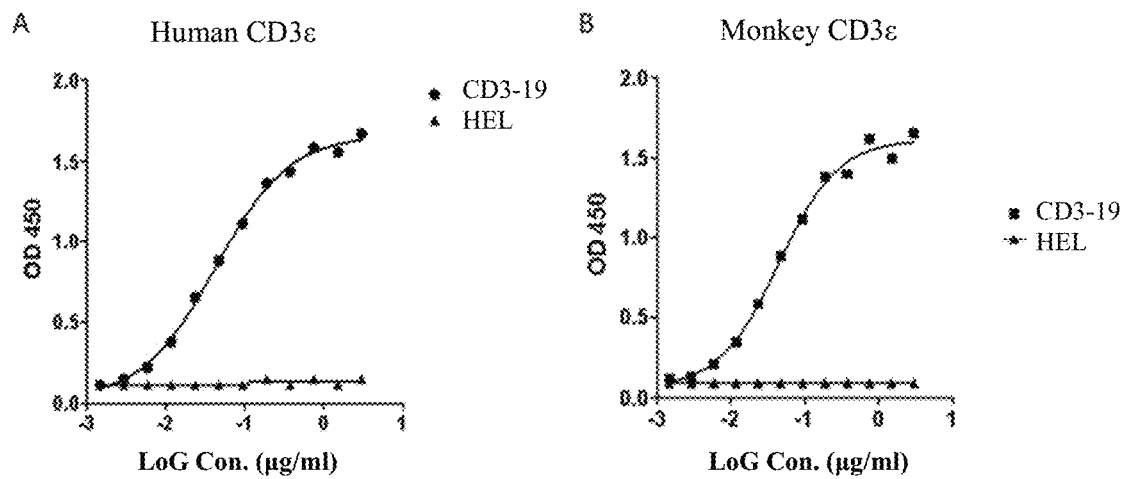
FIG. 1 shows the binding activity of the chimeric anti-CD3 antibody CD3-19 to human CD3ε (A) and monkey CD3ε (B).

To ensure that the present disclosure may be more readily understood, certain terms are first defined. Additional definitions are set forth throughout the detailed description.

The term "CD3" refers to cluster of differentiation 3, comprising γ, δ, ε and ζ chains. The term "CD3ε" refers to the E chain. The term "CD3" may comprise variants, isoforms, homologs, orthologs and paralogs. For example, an antibody specific for a human CD3 protein (such as CD3ε) may, in certain cases, cross-react with a CD3 protein from a species other than human, such as monkey. In other embodiments, an antibody specific for a human CD3 protein may be completely specific for the human CD3 protein and exhibit no cross-reactivity to other species or of other types, or may cross-react with CD3 from certain other species but not all other species.

The term "human CD3ε" refers to a CD3ε protein having an amino acid sequence from a human, such as the amino acid sequence having NCBI Accession No.: NP_000724.1 (Wipa P et al., (2020) Immunology 159(3): 298-308), or the amino acid sequence encoded by the nucleotide sequence set forth in SEQ ID NO: 24. The term "monkey CD3ε" refers to a CD3ε protein having an amino acid sequence from a monkey, such as the amino acid sequence having NCBI Accession No.: NP_001244149.1 (Maudhoo M D et al., (2014) Gigascience 3: 14).

The term "CD20" refers to the CD20 protein which is a marker molecule expressed on the surface of all B cells starting at the pro-B phase and progressively increasing in concentration until maturity, which is not expressed on hematopoietic stem cells, pro-B cells, or normal plasma cells. The term "human CD20" refers to a CD20 protein having an amino acid sequence from a human, such as the amino acid sequence of SEQ ID NO: 35. The term "monkey CD20" or "cynomolgus CD20" refers to a CD20 protein having an amino acid sequence from a monkey, such as the amino acid sequence of SEQ ID NO: 36.

The term "antibody" as referred to herein includes IgG, IgA, IgD, IgE and IgM whole antibodies and any antigen binding fragment (i.e., "antigen-binding portion") or single chains thereof. Whole antibodies are glycoproteins comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., a CD3 protein). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$ $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; (vi) an isolated complementarity determining region (CDR); and (viii) a nanobody, a heavy chain variable region containing a single variable domain and two constant domains. Furthermore, although the two domains of the Fv fragment, $V_L$ and $V_H$, are coded by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., (1988) *Science* 242:423-426; and Huston et al., (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

The term "FcR" or "Fc receptor" refers to a protein expressed on the surface of certain immune cells such as B lymphocytes, natural killer cells, and macrophages, which recognizes the Fc fragment of antibodies that are attached to cells or pathogens, and stimulates phagocytic or cytotoxic cells to destroy pathogens or target cells by e.g., antibody-mediated phagocytosis or antibody-dependent cell-mediated cytotoxicity. The FcR includes, FcαR, FcεR and FcγR, and the FcγR belongs to the immunoglobulin superfamily and is the most important Fc receptor for inducing phagocytosis of microbes, including FcγRI (CD64), FcγRIIA (CD32A), FcγRIIB (CD32B), and FcγRIIIA (CD16A).

An "isolated antibody", as used herein, is intended to refer to an antibody that is substantially free of other antibodies having different antigenic specificities (e.g., an isolated antibody that specifically binds a CD3 protein is substantially free of antibodies that specifically bind antigens other than CD3 proteins). An isolated antibody that specifically binds a human CD3 protein may, however, have cross-reactivity to other antigens, such as CD3 proteins from other species. Moreover, an isolated antibody can be substantially free of other cellular material and/or chemicals.

The term "monoclonal antibody" as used herein refers to a population of substantially homogeneous antibodies, i.e., the individual antibodies comprising the population are identical except for possible naturally occurring mutations and/or post-translation modifications (e.g., isomerization, amidation) that may be present in minor amounts. Monoclonal antibodies are highly specific, being directed against a single antigenic site. In contrast to polyclonal antibody preparations which typically include different antibodies directed against different determinants (epitopes), the monoclonal antibodies are directed against a single determinant on the antigen.

A "bispecific" molecule, as used herein, specifically binds two target molecules, or two different epitopes in a same target molecule. The bispecific antibody of the disclosure specifically binds CD3 and a disease associated antigen is a kind of bispecific molecule. In contrast, a "monospecific" molecule specifically binds a certain target molecule, especially a certain epitope in the target molecule.

The term "mouse antibody", as used herein, is intended to include antibodies having variable regions in which both the framework and CDR regions are derived from mouse germline immunoglobulin sequences. Furthermore, if the antibody contains a constant region, the constant region also is derived from mouse germline immunoglobulin sequences. The mouse antibodies of the disclosure can include amino acid residues not encoded by mouse germline immunoglobulin sequences (e.g., mutations introduced by random or site-specific mutagenesis in vitro or by somatic mutation in vivo). However, the term "mouse antibody", as used herein, is not intended to include antibodies in which CDR sequences derived from the germline of another mammalian species have been grafted onto mouse framework sequences.

The term "chimeric antibody" refers to an antibody made by combining genetic material from a nonhuman source with genetic material from a human being. Or more generally, a chimeric antibody is an antibody having genetic material from a certain species with genetic material from another species.

The term "humanized antibody", as used herein, refers to an antibody from non-human species whose protein sequences have been modified to increase similarity to antibody variants produced naturally in humans.

The phrases "an antibody recognizing an antigen" and "an antibody specific for an antigen" are used interchangeably herein with the term "an antibody which binds specifically to an antigen."

As used herein, an antibody that "specifically binds to human CD3" is intended to refer to an antibody that binds to human CD3 protein (and possibly a CD3 protein from one or more non-human species) but does not substantially bind to non-CD3 proteins. Preferably, the antibody binds to human CD3 protein with "high affinity", namely with a $K_D$ of $1.0 \times 10^{-8}$ M or less, more preferably $5.0 \times 10^{-9}$ M or less, and more preferably $1.0 \times 10^{-9}$ M or less.

The term "does not substantially bind" to a protein or cells, as used herein, means does not bind or does not bind with a high affinity to the protein or cells, i.e. binds to the protein or cells with a $K_D$ of $1.0 \times 10^{-6}$ M or more, more preferably $1.0 \times 10^{-10}$ M or more, more preferably $1.0 \times 10^{-4}$ M or more, more preferably $1.0 \times 10^{-3}$ M or more, even more preferably $1.0 \times 10^{-2}$ M or more.

The term "high affinity" for an IgG antibody refers to an antibody having a $K_D$ of $1.0 \times 10^{-6}$ M or less, more preferably $5.0 \times 10^{-8}$ M or less, even more preferably $1.0 \times 10^{-8}$ M or less, even more preferably $1.0 \times 10^{-9}$ M or less and even more preferably $5.0 \times 10^{-10}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably 10-8 M or less.

The term "$K_{assoc}$" or "$K_a$", as used herein, is intended to refer to the association rate of a particular antibody-antigen interaction, whereas the term "$K_{dis}$" or "$K_d$", as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacorem system.

The term "$EC_{50}$", also known as half maximal effective concentration, refers to the concentration of an antibody which induces a response halfway between the baseline and maximum after a specified exposure time.

The term "$IC_{50}$", also known as half maximal inhibitory concentration, refers to the concentration of an antibody which inhibits a specific biological or biochemical function by 50% relative to the absence of the antibody.

The term "cross-link" or "cross-linking" refers to aggregation of antibodies through binding of antibody Fc regions to FcRs on immune cells, or through binding of the antibodies (by e.g., the moiety in a bispecific molecule targeting the antigens) to the disease associated antigens on target cells. In in vitro tests, antibody cross-linking occurs when antibodies bind to the secondary antibodies coupled to e.g., ELISA plates. The anti-CD3 antibody or antigen-binding portion thereof of the disclosure can activate T cells when antibody cross-linking occurs. In contrast, "free" antibodies or antigen-binding portions thereof of the disclosure, that do not interact among each other or to other molecules to form antibody dimers or polymers, are not capable of activating T cells.

The term "subject" includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

The term "therapeutically effective amount" means an amount of the antibody or the antigen binding portion of the present disclosure sufficient to prevent or ameliorate the symptoms associated with a disease or condition (such as a chronic inflammation) and/or lessen the severity of the disease or condition. A therapeutically effective amount is understood to be in context to the condition being treated, where the actual effective amount is readily discerned by those of skill in the art.

Various aspects of the disclosure are described in further detail in the following subsections.

The antibody, or the antigen-binding portion thereof, of the disclosure specifically binds to human and monkey CD3 with comparable, if not higher, binding capability, as compared to prior art anti-CD3 antibodies.

The "free" antibody or antigen-binding portion thereof of the disclosure can bind CD3 but does not activate T cells, while when antibody cross-linking occurs, antibody or antigen-binding portion thereof of the disclosure can bind CD3 and activate T cells.

Thus, the antibody or antigen-binding portion thereof of the disclosure prepared with weak or no FcR binding affinity can be "free" or substantially "free" within bodies and can be used to treat inflammatory diseases and auto-immune diseases by inducing tolerance.

In another aspect, the antibody or antigen-binding portion thereof of the disclosure may be prepared as part of a non-FcR binding bispecific antibody against CD3 and another target such as a tumor associated antigen or an antigen associated with e.g., an infectious disease or an inflammatory disease, which, upon cross-linking through binding to the target other than CD3, activates T cells and kills target cells by e.g., releasing SMAPs. For example, the antibody or antigen-binding portion thereof may be prepared as part of a bispecific non-FcR binding antibody against CD3 and a tumor associated antigen, whose cross-linking occurs only when it binds to the tumor associated antigens at the lesion site. The bispecific antibody activates T cells to kill tumor cells when antibody cross-linking occurs. More importantly, compared to the prior art anti-CD3 antibodies, the bispecific antibody of the disclosure, upon cross-linking, causes less cytokine release, resulting in reduced toxicity.

The exemplary anti-CD3 antibody or antigen-binding portion thereof of the disclosure is structurally and chemically characterized as described below and in the following Examples. The heavy chain variable region CDRs and light chain variable region CDRs have been defined by the Kabat numbering system, whose sequence ID numbers are set forth in Table 1 below. However, as is well known in the art, CDRs can also be determined by other systems such as Chothia, and IMGT, AbM, or Contact numbering system/method, based on heavy chain/light chain variable region sequences. The sequence ID numbers of heavy/light chain variable regions are also set forth in Table 1, with some antibodies sharing the same VH and/or VL.

The antibody or antigen-binding portion thereof of the disclosure may contain a heavy chain constant region having e.g., weak or no FcR binding affinity, such as human IgG1 (N297A), human IgG1 (L234A+L235A) having the amino acid sequence of e.g., SEQ ID NO: 22 (X1=A, X2=A, X3=N, X4=P), human IgG1 (L234A+L235A+P329G) having the amino acid sequence of e.g., SEQ ID NO: 22 (X1=A, X2=A, X3=N, X4=G), human IgG1 (L234A+L235A+N297A) having the amino acid sequence of e.g., SEQ ID NO: 22 (X1=A, X2=A, X3=A, X4=P), human IgG1 (L234A+L235A+N297A+P329G) having the amino acid sequence of e.g., SEQ ID NO: 22 (X1=A, X2=A, X3=A, X4=G), human IgG2 (V234A+V237A), human IgG1 (L234A+V235E) heavy chain constant region, or a functional fragment thereof. The light chain constant region may be κ or λ light chain constant region, such as human κ or λ light chain constant region having the amino acid sequence of SEQ ID NOs: 23 or 32.

See, e.g., Kufer et al, cited supra; Cao and Suresh, *Bioconjugate Chemistry*, 9 (6), 635-644 (1998); and van Spriel et al., *Immunology Today*, 21 (8), 391-397 (2000), and the references cited therein.

The bispecific molecules of the disclosure pull T cells closer to the target cells. Cross-linking occurs to bispecific

TABLE 1

Amino acid sequence ID numbers of heavy/light chain variable regions and CDRs

| mAb ID | HV-CDR1 | HV-CDR2 | HV-CDR3 | HV | LV-CDR1 | LV-CDR2 | LV-CDR3 | LV |
|---|---|---|---|---|---|---|---|---|
| CD3-19 | 1, X1 = S | 2, X1 = D | 3, X1 = L, X2 = Y | 7 | 4, X1 = D, X2 = S | 5, X1 = Q, X2 = R, X3 = S | 6, X1 = V | 15 |
| 19-15 | 1, X1 = T | 2, X1 = I | 3, X1 = L, X2 = Y | 8 | 4, X1 = Q, X2 = N | 5, X1 = K, X2 = Q, X3 = R | 6, X1 = V | 16 |
| 15H2L2 | 1, X1 = T | 2, X1 = I | 3, X1 = L, X2 = Y | 9 | 4, X1 = Q, X2 = N | 5, X1 = K, X2 = Q, X3 = R | 6, X1 = V | 17 |
| 15H2L3 | 1, X1 = T | 2, X1 = I | 3, X1 = L, X2 = Y | 9 | 4, X1 = Q, X2 = N | 5, X1 = K, X2 = Q, X3 = R | 6, X1 = V | 18 |
| 15H3L2 | 1, X1 = T | 2, X1 = I | 3, X1 = L, X2 = Y | 10 | 4, X1 = Q, X2 = N | 5, X1 = K, X2 = Q, X3 = R | 6, X1 = V | 17 |
| 15H3L3 | 1, X1 = T | 2, X1 = I | 3, X1 = L, X2 = Y | 10 | 4, X1 = Q, X2 = N | 5, X1 = K, X2 = Q, X3 = R | 6, X1 = V | 18 |
| 19-26 | 1, X1 = T | 2, X1 = D | 3, X1 = I, X2 = W | 11 | 4, X1 = K, X2 = S | 5, X1 = N, X2 = L, X3 = H | 6, X1 = A | 19 |
| 26H2L3 | 1, X1 = T | 2, X1 = D | 3, X1 = I, X2 = W | 12 | 4, X1 = K, X2 = S | 5, X1 = N, X2 = L, X3 = H | 6, X1 = A | 20 |
| 26H3L3 | 1, X1 = T | 2, X1 = D | 3, X1 = I, X2 = W | 13 | 4, X1 = K, X2 = S | 5, X1 = N, X2 = L, X3 = H | 6, X1 = A | 20 |
| 19-37 | 1, X1 = T | 2, X1 = I | 3, X1 = I, X2 = Y | 14 | 4, X1 = R, X2 = N | 5, X1 = R, X2 = L, X3 = S | 6, X1 = V | 21 |

The disclosure relates to a bispecific molecule comprising one or more anti-CD3 antibodies or antigen-binding portions thereof of the disclosure linked to at least one other functional molecule, e.g., another peptide or protein (e.g., another antibody or ligand for a receptor), to generate a bispecific molecule that binds to at least two different binding sites or target molecules. Thus, as used herein, "bispecific molecule" includes molecules that have three or more binding specificities.

The bispecific molecule has, in addition to CD3 binding specificity, a second specificity to a disease associated antigen, preferably a disease associated antigen that is uniquely expressed on lesion cells, or alternatively expressed on lesion cells at high levels but at low levels on normal counterparts.

In certain embodiments, the disease associated antigen is a tumor associated antigen, such as CD20, CD19, CD22, CD4, CD24, CD38, CD123, CD228, CD138, BCMA, GPC3, CEA, CD276, gp100, 5T4, GD2, EGFR, MUC-1, PSMA, EpCAM, MCSP, SM5-1, MICA, MICB, ULBP and HER-2.

In certain embodiments, the disease associated antigen is an infectious disease associated antigen such as a marker protein on pathogens or infected cells. The infectious disease associated antigen may be CD4, BHsAg, LMP-1 and LMP2, wherein CD4 is the target for AIDS treatment.

In certain embodiments, the disease associated antigen is an inflammatory disease associated antigen such as a marker protein expressed on active immune cells causing inflammations, including, but not limited to, IL17R and CD6.

Bispecific molecules may be in many different formats and sizes. At one end of the size spectrum, a bispecific molecule retains the traditional antibody format, except that, instead of having two binding arms of identical specificity, it has two binding arms each having a different specificity. At the other extreme are bispecific molecules consisting of two single-chain antibody fragments (scFv's) linked by a peptide chain, a so-called Bs(scFv) 2 construct. Intermediate-sized bispecific molecules include two different F(ab) fragments linked by a peptidyl linker. Bispecific molecules of these and other formats can be prepared by genetic engineering, somatic hybridization, or chemical methods.

molecules when the bispecific molecules bind to the disease associated antigens, and T cells can be activated to kill target cells accordingly.

In certain embodiments, the disease associated antigen is CD20, a marker on pre- and mature B cells, but not on hematopoietic stem cells, pro-B cells or normal plasma cells, is a promising antigen for diagnosis and/or treatment of B cell lymphomas and B cell leukemia.

The bispecific antibody of the disclosure may contain one CD3ε binding domain, and one to five CD20 binding domains. In one embodiment, the bispecific antibody may contain one CD3ε binding domain and two CD20 binding domains. In one embodiment, the CD20 binding domain is an antibody or an antigen-binding portion thereof, e.g., an Fv and/or a scFv, specific to CD20. In one embodiment, the CD3 binding domain may be the anti-CD3 antigen or antigen-binding portion thereof, e.g., an Fv, of the disclosure. The two CD20 binding domains may bind to the same or different antigen epitopes, may contain the same or different antigen binding domain sequences, and/or have the same or different antigen-binding domain formats.

In one embodiment, the bispecific antibody contains one Fv specifically binding CD3, one Fv specifically binding CD20, and one scFv specifically binding CD20. In one embodiment, the Fv and the scFv binding CD20 have the same heavy chain variable region and light chain variable region.

The bispecific antibody against CD3 and CD20 may be an IgG like antibody. In one embodiment, the bispecific antibody contains a half-IgG specific to CD3, a half-IgG specific to CD20, and a scFv against CD20 linked to the N terminus of the heavy chain variable region or the light chain variable region of the anti-CD3 half-IgG.

In one embodiment, the bispecific antibody may contain:
i) a first polypeptide, containing an anti-CD20 heavy chain variable region and a heavy chain constant region,
ii) a second polypeptide, containing an anti-CD20 light chain variable region,
iii) a third polypeptide, containing an anti-CD20 heavy chain variable region, an anti-CD20 light chain variable region, an anti-CD3ε heavy chain variable region, and a heavy chain constant region, and iv) a fourth polypeptide, containing an anti-CD3ε light chain variable region, wherein the anti-CD20 heavy chain variable region in the first polypeptide and the anti-CD20 light chain variable region in the second polypeptide associate to form an antigen binding fragment against CD20, the anti-CD20 heavy chain variable region and the anti-CD20 light chain variable region in the third polypeptide associate to form an antigen binding fragment against CD20, the anti-CD3ε heavy chain variable region in the third polypeptide and the anti-CD3ε light chain variable region in the fourth polypeptide associate to form an antigen binding fragment against CD3ε, and the heavy chain constant region in the first polypeptide and the heavy chain constant region in the third polypeptide are associated together via e.g., the knob-into-hole approach, the covalent bond or the disulfide bond.

In one embodiment, the first polypeptide comprises, from N terminus to C terminus, the anti-CD20 heavy chain variable region and the heavy chain constant region. In one embodiment, the third polypeptide comprises, from N terminus to C terminus, the anti-CD20 heavy chain variable region, the anti-CD20 light chain variable region, the anti-CD3ε heavy chain variable region, and the heavy chain constant region; or alternatively the anti-CD20 light chain variable region, the anti-CD20 heavy chain variable region, the anti-CD3ε heavy chain variable region, and the heavy chain constant region. In one embodiment, the heavy chain constant region in the first polypeptide is with a knob, and the heavy chain constant region in the third polypeptide is with a hole.

In another embodiment, the bispecific antibody may contain:

i) a first polypeptide, containing an anti-CD20 heavy chain variable region and a heavy chain constant region, ii) a second polypeptide, containing an anti-CD20 light chain variable region, iii) a third polypeptide, containing an anti-CD3ε heavy chain variable region, and a heavy chain constant region, and iv) a fourth polypeptide, containing an anti-CD20 heavy chain variable region, an anti-CD20 light chain variable region, and an anti-CD3ε light chain variable region, wherein the anti-CD20 heavy chain variable region in the first polypeptide and the anti-CD20 light chain variable region in the second polypeptide associate to form an antigen binding fragment against CD20, the anti-CD3ε heavy chain variable region in the third polypeptide and the anti-CD3ε light chain variable region in the fourth polypeptide associate to form an antigen binding fragment against CD3ε, the anti-CD20 heavy chain variable region and the anti-CD20 light chain variable region in the fourth polypeptide associate to form an antigen binding fragment against CD20, and the heavy chain constant region in the first polypeptide and the heavy chain constant region in the third polypeptide are associated together via e.g., the knob-into-hole approach, the covalent bond or the disulfide bond.

In one embodiment, the first polypeptide comprises, from N terminus to C terminus, the anti-CD20 heavy chain variable region and the heavy chain constant region. In one embodiment, the third polypeptide comprises, from N terminus to C terminus, the anti-CD3ε heavy chain variable region, and the heavy chain constant region. In one embodiment, the fourth polypeptide comprises, from N terminus to C terminus, the anti-CD20 heavy chain variable region, the anti-CD20 light chain variable region and the anti-CD3ε light chain variable region; the anti-CD20 light chain variable region, the anti-CD20 heavy chain variable region, and the anti-CD3ε light chain variable region; the anti-CD3ε light chain variable region, the anti-CD20 light chain variable region, and the anti-CD20 heavy chain variable region; or alternatively the anti-CD3ε light chain variable region, the anti-CD20 heavy chain variable region, and the anti-CD20 light chain variable region.

In the bispecific antibody, the anti-CD20 heavy chain variable region may be linked via a linker to the anti-CD20 light chain variable region, to form a scFv. The anti-CD20 heavy chain variable region or the anti-CD20 light chain variable region may be linked via a linker to the anti-CD3 antibody or antigen-binding portion thereof.

The linker may be made up of amino acids linked together by peptide bonds, preferably from 5 to 30 amino acids linked by peptide bonds, wherein the amino acids are selected from the 20 naturally occurring amino acids. One or more of these amino acids may be glycosylated, as is understood by those of skill in the art. In one embodiment, the 5 to 30 amino acids may be selected from glycine, alanine, proline, asparagine, glutamine, serine and lysine. In one embodiment, a linker is made up of a majority of amino acids that are sterically unhindered, such as glycine and alanine. Exemplary linkers are polyglycines, particularly poly(Gly-Ala), and polyalanines. One exemplary linker in the disclosure is one with the amino acid sequence of SEQ ID NO: 28.

The linker may also be a non-peptide linker. For example, alkyl linkers such as —NH—, —(CH$_2$)s-C(O)—, wherein s=2-20 can be used. These alkyl linkers may further be substituted by any non-sterically hindering group such as lower alkyl (e.g., C$_{1-4}$) lower acyl, halogen (e.g., Cl, Br), CN, NH$_2$, phenyl, etc.

In another embodiment, the antibody of the disclosure, including the anti-CD3 antibody and the bispecific antibody against e.g., CD3 and CD20, may comprise a heavy and/or light chain variable region sequences or CDR1, CDR2 and CDR3 sequences with one or more conservative modifications. It is understood in the art that certain conservative sequence modification can be made which do not remove antigen binding. See, e.g., Brummell et al., (1993) *Biochem* 32:1180-8; de Wildt et al., (1997) *Prot. Eng.* 10:835-41; Komissarov et al., (1997) *J. Biol. Chem.* 272:26864-26870; Hall et al., (1992) *J. Immunol.* 149:1605-12; Kelley and O'Connell (1993) *Biochem.* 32:6862-35; Adib-Conquy et al., (1998) *Int. Immunol.* 10:341-6 and Beers et al., (2000) *Clin. Can. Res.* 6:2835-43.

As used herein, the term "conservative sequence modification" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the disclosure by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the disclosure can be replaced with other amino acid residues from the same side chain family and the altered antibody can be tested for retained function (i.e., the functions set forth above) using the functional assays described herein.

Antibodies of the disclosure, including the anti-CD3 antibodies and the bispecific antibodies against e.g., CD3 and CD20, can be prepared using an antibody having one or more of the $V_H/V_L$ sequences of the antibody of the present disclosure, as starting material to engineer a modified antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al., (1998) *Nature* 332:323-327; Jones et al., (1986) *Nature* 321:522-525; Queen et al., (1989) *Proc. Natl. Acad.* See also U.S.A. 86:10029-10033; U.S. Pat. Nos. 5,225,539; 5,530,101; 5,585,089; 5,693,762 and 6,180,370).

Accordingly, another embodiment of the disclosure pertains to an isolated monoclonal antibody, or antigen binding portion thereof, and/or an bispecific antibody, which may comprise a heavy chain variable region that may comprise CDR1, CDR2, and CDR3 sequences which may comprise the sequences of the present disclosure, as described above, and/or a light chain variable region which may comprise CDR1, CDR2, and CDR3 sequences which may comprise the sequences of the present disclosure, as described above. While these antibodies contain the $V_H$ and $V_L$ CDR sequences of the monoclonal antibody of the present disclosure, they can contain different framework sequences.

Such framework sequences can be obtained from public DNA databases or published references that include germline antibody gene sequences. For example, germline DNA sequences for human heavy and light chain variable region genes can be found in the "VBase" human germline sequence database (available on the Internet at mrc-cpe.cam.ac.uk), as well as in Kabat et al., (1991), cited supra; Tomlinson et al., (1992) *J. Mol. Biol.* 227:776-798; and Cox et al., (1994) *Eur. J. Immunol.* 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank Accession Nos.: 1-69 (NG—0010109, NT—024637 & BC070333), 3-33 (NG—0010109 & NT—024637) and 3-7 (NG—0010109 & NT—024637). As another example, the following heavy chain germline sequences found in the HCo12 HuMAb mouse are available in the accompanying Genbank Accession Nos.: 1-69 (NG—0010109, NT—024637 & BC070333), 5-51 (NG—0010109 & NT—024637), 4-34 (NG—0010109 & NT—024637), 3-30.3 (CAJ556644) & 3-23 (AJ406678).

Antibody protein sequences are compared against a compiled protein sequence database using one of the sequence similarity searching methods called the Gapped BLAST (Altschul et al., (1997), supra), which is well known to those skilled in the art.

Preferred framework sequences for use in the antibodies of the disclosure are those that are structurally similar to the framework sequences used by antibodies of the disclosure. The $V_H$ CDR1, CDR2, and CDR3 sequences can be grafted onto framework regions that have the identical sequence as that found in the germline immunoglobulin gene from which the framework sequence derives, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as known in the art. Preferably conservative modifications (as known in the art) are introduced. The mutations can be amino acid substitutions, additions or deletions, but are preferably substitutions. Moreover, typically no more than one, two, three, four or five residues within a CDR region are altered.

Engineered antibodies of the disclosure include those in which modifications have been made to framework residues within $V_H$ and/or $V_L$, e.g. to improve the properties of the antibody. Typically, such framework modifications are made to decrease the immunogenicity of the antibody. For example, one approach is to "backmutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043.

In addition, or as an alternative to modifications made within the framework or CDR regions, antibodies of the disclosure can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the disclosure can be chemically modified (e.g., one or more chemical moieties can be attached to the antibody) or be modified to alter its glycosylation, again to alter one or more functional properties of the antibody.

In one embodiment, the hinge region of $C_{H1}$ is modified in such that the number of cysteine residues in the hinge region is altered, e.g., increased or decreased. This approach is described further in U.S. Pat. No. 5,677,425. The number of cysteine residues in the hinge region of $CH_1$ is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the $C_{H2}$-$C_{H3}$ domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745.

In certain embodiments, the heavy chain constant region may be mutated to have reduced FcR or complement system protein binding affinity. The amino acid residue mutation may be e.g., N297A, L234A+L235A, L234A+V235E, L234A+L235A+P329G, L234A+L235A+N297A, and L234A+L235A+N297A+P329G in human IgG1 heavy chain constant region, and V234A+V237A in human IgG2 heavy chain constant region.

In still another embodiment, the glycosylation of an antibody is modified. For example, a glycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase or reduce the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the disclosure to thereby produce an antibody with altered glycosylation. For example, the cell lines Ms704, Ms705, and Ms709 lack the fucosyltransferase gene, FUT8 (α (1, 6)-fucosyltransferase), such that antibodies expressed in the Ms704, Ms705, and Ms709 cell lines lack fucose on their carbohydrates. The Ms704, Ms705, and Ms709 FUT8−/− cell lines were created by the targeted disruption of the FUT8 gene in CHO/DG44 cells using two replacement vectors (see U.S. Patent Publication No. 20040110704 and Yamane-Ohnuki et al., (2004) Biotechnol Bioeng 87:614-22). As another example, EP 1,176,195 describes a cell line with a functionally disrupted FUT8 gene, which encodes a fucosyl transferase, such that antibodies expressed in such a cell line exhibit hypofucosylation by reducing or eliminating the α-1, 6 bond-related enzyme. EP 1,176,195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell (see also Shields et al., (2002) J. Biol. Chem. 277:26733-26740). Antibodies with a modified glycosylation profile can also be produced in chicken eggs, as described in PCT Publication WO 06/089231. Alternatively, antibodies with a modified glycosylation profile can be produced in plant cells, such as Lemna. The fucose residues of the antibody can be cleaved off using a fucosidase enzyme; e.g., the fucosidase α-L-fucosidase removes fucosyl residues from antibodies (Tarentino et al., (1975) Biochem. 14:5516-23).

Another modification of the antibodies herein that is contemplated by this disclosure is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the disclosure. See, e.g., EP 0 154 316 and EP 0 401 384.

Antibodies of the disclosure, including the anti-CD3 antibodies and the bispecific antibodies against e.g., CD3 and CD20, can be characterized by their various physical properties, to detect and/or differentiate different classes thereof.

For example, antibodies can contain one or more glycosylation sites in either the light or heavy chain variable region. Such glycosylation sites may result in increased immunogenicity of the antibody or an alteration of the pK of the antibody due to altered antigen binding (Marshall et al (1972) Annu Rev Biochem 41:673-702; Gala and Morrison (2004) J Immunol 172:5489-94; Wallick et al (1988) J Exp Med 168:1099-109; Spiro (2002) Glycobiology 12:43R-56R; Parekh et al (1985) Nature 316:452-7; Mimura et al., (2000) Mol Immunol 37:697-706). Glycosylation has been known to occur at motifs containing an N-X-S/T sequence. In some instances, it is preferred to have an anti-CD3 antibody that does not contain variable region glycosylation. This can be achieved either by selecting antibodies that do not contain the glycosylation motif in the variable region or by mutating residues within the glycosylation region.

In a preferred embodiment, the antibodies do not contain asparagine isomerism sites. The deamidation of asparagine may occur on N-G or D-G sequences and result in the creation of an isoaspartic acid residue that introduces a link into the polypeptide chain and decreases its stability (isoaspartic acid effect).

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an anti-CD3 antibody that contains a pI value that falls in the normal range. This can be achieved either by selecting antibodies with a pI in the normal range or by mutating charged surface residues.

In another aspect, the disclosure provides nucleic acid molecules that encode the heavy and/or light chain variable regions, or CDRs of the anti-CD3 antibody or antigen-binding portion thereof, or the bispecific antibody, such as the nucleic acid molecule encoding anti-CD20 heavy chain variable region-linker-anti-CD20 light chain variable region-linker-anti-CD3 heavy chain variable region, anti-CD20 light chain variable region-linker-anti-CD20 heavy chain variable region-linker-anti-CD3 heavy chain variable region. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques. A nucleic acid of the disclosure can be, e.g., DNA or RNA and may or may not contain intronic sequences. In a preferred embodiment, the nucleic acid is a cDNA molecule.

Nucleic acids of the disclosure can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

Preferred nucleic acids molecules of the disclosure include those encoding the $V_H$ and/or $V_L$ sequences of the CD3 monoclonal antibody or the CDRs. Once DNA fragments encoding $V_H$ and/or $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($C_{H1}$, $C_{H2}$ and CH3). The sequences of human heavy chain constant region genes are known in the art and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain $C_{H1}$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, e.g., encoding the amino acid sequence (Gly4-Ser)3, such that the $V_H$ and $V_L$ sequences can be expressed as a contiguous single-chain protein, with the $V_L$ and $V_H$ regions joined by the flexible linker (see e.g., Bird et al., (1988) Science 242:423-426; Huston et al., (1988) Proc. Natl. Acad. Sci. USA 85:5879-5883; McCafferty et al., (1990) Nature 348:552-554).

For the bispecific antibody of the disclosure, nucleotide sequences encoding the anti-CD3 antibodies' CDRs, VH and VL, and the anti-CD20 antibodies' VH and VL, and linkers are firstly synthesized, and then combined according to the structures of required bispecific antibodies. For example, the nucleotide sequences encoding the anti-CD20 heavy chain variable region, the linker, the anti-CD20 light chain variable region, the linker, and the anti-CD3 heavy chain variable region may be operatively linked as required.

The anti-CD3 antibodies of the disclosure can be produced using the well-known somatic cell hybridization (hybridoma) technique of Kohler and Milstein (1975) Nature 256: 495. Other embodiments for producing monoclonal antibodies include viral or oncogenic transformation of B lymphocytes and phage display techniques. Chimeric or humanized antibodies are also well known in the art. See e.g., U.S. Pat. Nos. 4,816,567; 5,225,539; 5,530,101; 5,585,089; 5,693,762 and 6,180,370, the contents of which are specifically incorporated herein by reference in their entirety. Antibodies of the disclosure also can be produced in a host cell transfectoma using, for example, a combination of recombinant DNA techniques and gene transfection methods as is well known in the art (e.g., Morrison, S. (1985) Science 229:1202). In one embodiment, DNA encoding partial or full-length light and heavy chains obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The bispecific antibodies of the disclosure, especially those against CD3 and CD20, may be produced by i) inserting the nucleotide sequences encoding polypeptide chains of the bispecific antibodies into one or more expression vectors which are operatively linked to regulatory sequences transcription and translation that control transcription or translation; (ii) transducing or transfecting host cells with expression vectors; and (iii) expressing polypeptide chains to form the bispecific antibodies of the disclosure.

The term "regulatory sequence" is intended to include promoters, enhancers and other expression control elements (e.g., polyadenylation signals) that control the transcription or translation of the antibody genes. Such regulatory sequences are described, e.g., in Goeddel (Gene Expression Technology. Methods in Enzymology 185, Academic Press, San Diego, Calif. (1990)). Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, e.g., the adenovirus major late promoter (AdMLP) and polyomavirus enhancer. Alternatively, non-viral regulatory sequences can be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe et al., (1988) *Mol. Cell. Biol.* 8:466-472). The expression vector and expression control sequences are chosen to be compatible with the expression host cell used.

The expression vector can encode a signal peptide that facilitates secretion of the polypeptide chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the polypeptide chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the heavy and/or light chains of the anti-CD3 antibodies, or the polypeptide chains of the bispecific antibodies of the disclosure, the expression vector(s) is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the disclosure in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

The expression vectors that can be used in the present application include but are not limited to plasmids, viral vectors, yeast artificial chromosomes (YACs), bacterial artificial chromosomes (BACs), transformation-competent artificial chromosomes (TACs), mammalian artificial chromosomes (MACs) and human artificial episomal chromosomes (HAECs).

Preferred mammalian host cells for expressing the recombinant antibodies of the disclosure include Chinese Hamster Ovary (CHO cells) (including dhfr-CHO cells, described in Urlaub and Chasm, (1980) *Proc. Natl. Acad. Sci. USA* 77:4216-4220, used with a DHFR selectable marker, e.g., as described in R. J. Kaufman and P. A. Sharp (1982) *J. Mol. Biol.* 159:601-621), NSO myeloma cells, COS cells and SP2 cells. In particular for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

In another aspect, the present disclosure provides a pharmaceutical composition which may comprise one or more antibodies or antigen-binding portions thereof, the bispecific antibodies, or alternatively nucleic acid molecules of the disclosure capable of expressing the same, formulated together with a pharmaceutically acceptable carrier. The pharmaceutical composition may optionally contain one or more additional pharmaceutically active ingredients, such as an anti-tumor antibody, an anti-infection antibody, an antibody for immune enhancement, or an antibody for an autoimmune disease, or alternatively a non-antibody anti-tumor agent, a non-antibody anti-infection agent, a non-antibody immune enhancement agent, or a non-antibody anti-inflammation agent. The pharmaceutical composition of the disclosure may be used in combination with an additional anti-tumor agent, an additional anti-infection agent, an additional immune enhancement agent, or an additional autoimmune disease-treating agent.

The pharmaceutical composition may comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients are taught in Gennaro, ed., Remington: *The Science and Practice of Pharmacy*, 20th Ed. (Lippincott Williams & Wilkins 2003), the disclosure of which is incorporated herein by reference.

Preferably, the pharmaceutical composition is suitable for intravenous, intramuscular, subcutaneous, parenteral, spinal or epidermal administration (e.g., by injection or infusion). Depending on the route of administration, the active ingredient can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion. Alternatively, an antibody of the disclosure can be administered via a non-parenteral route, such as a topical, epidermal or mucosal route of administration, e.g., intranasally, orally, vaginally, rectally, sublingually or topically.

Pharmaceutical compositions can be in the form of sterile aqueous solutions or dispersions. They can also be formulated in a micro-emulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about 99% of active ingredient, preferably from about 0.1% to about 70%, most preferably from about 1% to about 30% of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active ingredient calculated to produce the desired therapeutic effect in association with the required pharmaceutical carrier. Alternatively, antibody can be administered as a sustained release formulation, in which case less frequent administration is required.

The anti-CD3 antibodies of the disclosure may be administered with reference to OKT3 dose approved by FDA, and should be finally determined by physicians depending on a subject's e.g., sex, age, medical history and etc. The dose of the bispecific antibodies of the disclosure against CD20 and CD3 may be determined by physicians depending on a subject's e.g., sex, age, medical history and etc.

A "therapeutically effective dosage" of the anti-CD3 antibody or antigen-binding portion thereof, or the bispecific antibody against CD3 and CD20 of the disclosure, may result in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably reduce tumor size by at least about 20%, more preferably by at least about 40%, even more preferably by at least about 60%, and still more preferably by at least about 80%, or even eliminate tumors, relative to untreated subjects. For subjects receiving allogeneic transplant, a "therapeutically effective dosage" preferably reduce graft rejection by at least about 20%, more preferably by at least about 40%, even more preferably by at least about 60%, and still more preferably by at least about 80%, or even eliminate graft rejections, relative to untreated subjects. For the subjects with inflammatory diseases or autoimmune diseases, a "therapeutically effective dosage" preferably reduce inappropriate inflammations by at least about 20%, more preferably by at least about 40%, even more preferably by at least about 60%, and still more preferably by at least about 80%, or even eliminate inflammations, relative to untreated subjects.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Pharmaceutical compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparatuses (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the antibodies of the disclosure can be formulated to ensure proper distribution in vivo. For example, to ensure that the therapeutic antibody or antigen-binding portion thereof of the disclosure cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; V. V. Ranade (1989) *J. Clin. Pharmacol.* 29:685; Umezawa et al., (1988) *Biochem. Biophys. Res. Commun.* 153:1038; Bloeman et al., (1995) *FEBS Lett.* 357:140; M. Owais et al., (1995) *Antimicrob. Agents Chemother.* 39:180; Briscoe et al., (1995) *Am. J. Physiol.* 1233:134; Schreier et al., (1994) *J. Biol. Chem.* 269:9090; Keinanen and Laukkanen (1994) *FEBS Lett.* 346:123; and Killion and Fidler (1994) *Immunomethods* 4:273.

The pharmaceutical composition of the disclosure has multiple in vitro and in vivo applications. For example, the composition may be used in treatment and alleviation of inflammatory diseases, or in reducing or eliminating graft rejection.

In one aspect, the pharmaceutical composition comprising a therapeutically effective amount of the anti-CD3 antibody or antigen-binding portion thereof of the disclosure may be used to treat and/or alleviate inflammatory diseases and auto-immune diseases, or to reduce or eliminate graft rejection. In one embodiment, the antibody or antigen-binding portion thereof of the disclosure may contain a heavy chain constant region with weak or no FcR binding affinity. In certain embodiments, the inflammatory disease is multiple sclerosis (MS) or inflammatory bowel disease (IBD, such as Crohn's disease). In certain embodiments, the auto-immune disease is type I diabetes.

In another aspect, the pharmaceutical composition comprising a therapeutically effective amount of the bispecific antibody of the disclosure may be used to treat certain diseases, wherein the bispecific antibody is specific to CD3 and a disease associated antigen, does not contain Fc region, or contains Fc regions with weak or no FcR binding affinity. Depending on the disease associated antigen, the pharmaceutical composition may be used to treat various tumors such as colon adenocarcinoma, breast cancer, renal cell cancer, melanoma, pancreatic cancer, non-small-cell lung cancer, glioblastoma, and gastric cancer, original or metastatic; infectious diseases such as AIDS; and inflammatory diseases or autoimmune diseases.

In certain embodiments, the pharmaceutical composition comprising the bispecific antibody of the disclosure against CD20 and CD3, and/or the nucleotide molecule encoding the same, may be used to treat or alleviate B cell associated diseases such as B-cell lymphomas, B-cell leukemia, or a B-cell mediated auto-immune disease. The B-cell lymphomas and the B-cell leukemia include, but not limited to, non-Hodgkin's lymphoma (NHL), chronic lymphocytic leukemia (CLL), and diffuse large B-cell lymphoma (DLBCL).

In another aspect, the disclosure provides methods of combination therapy in which the pharmaceutical composition of the present disclosure is co-administered with one or more additional antibodies or non-antibody agents. In one embodiment, prior to or along with administration the pharmaceutical composition comprising the bispecific antibody of the disclosure against CD20 and CD3, and/or the nucleotide molecule encoding the same, additional anti-CD20 antibodies can be administered to a subject in need thereof. The anti-CD20 antibodies may kill most CD20+ B cells, so as to decrease the amount of the bispecific antibody against CD20 and CD3 to be administered, such that the adverse effects caused by the bispecific antibody may be further reduced.

The combination of therapeutic agents discussed herein can be administered concurrently as a single composition in a pharmaceutically acceptable carrier, or concurrently as separate compositions with each agent in a pharmaceutically acceptable carrier. In another embodiment, the combination of therapeutic agents can be administered sequentially.

Furthermore, if more than one dose of the combination therapy is administered sequentially, the order of the sequential administration can be reversed or kept in the same order at each time point of administration, sequential administrations can be combined with concurrent administrations, or any combination thereof.

Although the present invention and its advantages have been described in detail, it should be understood that various changes, substitutions and alterations can be made herein without departing from the spirit and scope of the invention as defined in the appended claims.

The present disclosure is further illustrated by the following examples, which should not be construed as further limiting. The contents of all figures and all references, Genbank sequences, patents and published patent applications cited throughout this application are expressly incorporated herein by reference.

EXAMPLES

Example 1 Generation of Mouse Anti-CD3 Monoclonal Antibodies

CD3ε (NCBI reference no.: NP_000724.1)-coding cDNAs (SEQ ID NO: 24) were synthesized and cloned into pcDNA3.1 plasmids between EcoRI and BamHI sites, to obtain hCD3ε-pcDNA3.1. Similarly, an expression vector hCD3δ-pcDNA3.1 was constructed with the cDNA encoding hCD36 (NCBI reference no.: NP_000723.1) as set forth in SEQ ID NO: 25. To obtain these vectors in large quantities, plasmids were extracted using Endofree Plasmid Giga kit (QIAGEN) according to manufacturer's instruction.

To generate monoclonal antibodies binding human CD3, 6-week old BALB/c mice were inoculated with the plasmids prepared above. Briefly, mice were intramuscularly injected with 25 μl 1 mg/ml hCD3ε-pcDNA3.1 and 25 μl 1 mg/ml hCD3δ-pcDNA3.1. Electric current was applied to the injection sites with a BTX ECM830 pulse generator with two electrodes. Three boosts were performed in a three-week-interval with the injection and electroporation. Four days post the final immunization boost, spleens were harvested for phage display library construction.

To construct a scFv phage display library, the total spleen RNAs were extracted using Trizol kit (Invitrogen), and cDNAs were synthesized using Reverse Transcriptase Kit (Invitrogen), according to manufacturer's instruction. Gene amplification was done by PCR using the cDNA synthesized above as templates, and the scFv phage library was constructed using a proprietary phagemid, pTGS. Briefly, the light chain variable regions were amplified by PCR, purified using Qiagen PCR/purification kit, digested with restriction enzymes NheI and NotI (NEB), and then ligated into the phagemid pTGS (digested with the same restriction enzymes and purified by agarose gel) at 16° C. Following ligation, the recombinant DNAs were precipitated, washed and dissolved in distilled water. The recombinant DNAs were then transformed into E. coli TG1 cells by electroporation. Then, the cells were suspended in 10 ml of SOC medium, and cultured for 1 h at 37° C. with gentle shaking. The cell cultures were plated on 2YT agar/ampicillin and the ampicillin resistant colonies were counted. For cloning of the heavy chain variable fragments, PCR products were digested with NcoI and XhoI and ligated into the light chain variable region library and transformed into E. coli TG1. The library was scraped from the large plate, and inoculated to 2YTAG liquid culture media. Approximately $10^{12}$ pfu helper phages were added to TG1 samples containing scFv gene libraries and incubated for 1 h at 37° C. with shaking. Seventy g/ml of Kanamycin was added and the cultures were shaken overnight at 30° C. The cells were centrifuged at 4000 rpm for 15 min at 4° C. The resultant supernatants were mixed with 5 ml 20% PEG 8000/2.5 M NaCl and incubated on ice for 30 min, and then the phages were precipitated by centrifugation at 8000 rpm for 20 min at 4° C. The phages were re-suspended in 1.5 ml PBS containing 1% BSA, vortexed and centrifuged at 13000 rpm for 5 min to remove residual bacteria. The supernatants were stored at 4° C. or used directly for the biopinning (see below).

Human CD3ε-his (Cat #:10977-H08s, SinoBiological, China) and monkey CD3ε-his (Cat #: 90047-C08H, Sino-Biological, China) were used to screen antibodies against both human and monkey CD3 proteins. Briefly, the phages were incubated with beads coupled with human CD3ε-his proteins in a shaker at room temperature for 2 h. The unbound phages were washed away using PBS and then 0.1M Glycine-HCl (pH2.2) was used to elute antigen bound phages. Eluted phages were neutralized to pH 7.0 using 1.5M Tris-HCl (pH8.8). The above neutralized phages were used to infect 10 ml of TG1 bacteria, which were cultured at 37° C. until $OD_{600}$ reached 0.6. The bacteria cultures were pelleted by centrifugation, and the pellets were re-suspended in culture media and then plated on a 2YTAG plate for the next round of screening. The selected phages positive for human CD3 binding were incubated with beads coupled with monkey CD3ε-his proteins in a shaker at room temperature for 2 h. The unbound phages were washed away using PBS and then 0.1M Glycine-HCl (pH2.2) was used to elute antigen bound phages. Eluted phages were neutralized to pH 7.0 using 1.5M Tris-HCl (pH8.8). The above neutralized phages were used to infect 10 ml of TG1 bacteria, which were cultured at 37° C. until $OD_{600}$ reached 0.6. The bacteria cultures were pelleted by centrifugation, and the pellets were re-suspended in culture media and then plated on a 2YTAG plate for the next round of screening. Three rounds of such enrichment and screening were carried out in total.

After three rounds of biopanning, phages with high binding capabilities were collected and used to infect bacterial cells. Single bacterial colonies were picked up and grown in 96-well plates. Phage-based ELISA was then used to identify high binders against both human CD3ε-his (Cat #:10977-H08s, SinoBiological, China) and monkey CD3ε-his (Cat #: 90047-C08H, SinoBiological, China), which were then subject to DNA sequencing. One readable scFv sequence was identified from high binding clones, and designated as CD3-19, whose heavy chain and light chain variable region sequence ID numbers were set forth in Table 1.

Example 2 Expression and Purification of Full Length Anti-CD3 Antibody

The CD3-19 scFv antibody as screened was expressed in HEK293F (Cobioer, China) cells as a full length antibody for further characterization. Briefly, the expression vectors were constructed by cloning heavy/light chain variable region plus human IgG1/kappa constant region (amino acid sequences set forth in SEQ ID Nos.: 22 (X1=L, X2=L, X3=N, X4=P) and 23, respectively) into pCDNA3.1 between EcoRI and BamHI sites (Invitrogen, Carlsbad, USA).

The anti-CD3 antibody was transiently expressed in HEK-293F cells using PEI transfection according to the manufacturer's manual. Briefly, HEK-293F cells were transfected with the vectors using polyethyleneinimine (PEI) at a DNA:PEI ratio of 1:3. The plasmid concentration used for transfection was 1.5 µg/ml. Transfected HEK-293F cells were cultured in an incubator in 5% $CO_2$ at 37° C. with shaking at 120 RPM. After 10-12 days, cell culture supernatants were harvested, and subject to centrifugation at 3500 rpm for 5 minutes and then to filtration using 0.22 µm capsules to remove cell debris. The antibodies were then purified using a pre-equilibrated Protein-A affinity column (Cat #: 17040501, Lot #: 10252250, GE, USA) and eluted with the elution buffer (20 mM citric acid, pH3.0-3.5). After buffer exchange, antibodies were kept in PBS buffer (pH 7.0) and the concentration was determined using a Nano-Drop instrument. The purified monoclonal antibodies were then subject to further characterizations.

Example 3 Binding Capability of Chimeric Antibody

The purified chimeric CD3-19 antibody was tested for its binding capability to recombinant human and monkey CD3ε proteins by ELISA.

Briefly, an ELISA plate was coated with 100 µl 500 ng/ml human CD3ε-his (Cat #:10977-H08s, SinoBiological, China) for each well overnight at 4° C. Then, each well was blocked with 200 µl blocking buffer (PBS+1% BSA+1% goat serum+0.05% Tween 20) at room temperature for 2 h, and then added and incubated with 100 µl serially diluted anti-CD3 antibodies (starting at 40 µg/ml) at room temperature for 1 h. After rinsed with PBST (PBS+0.05% Tween 20) for three times, the ELISA plate was added and incubated with HRP conjugated goat anti-human IgG (1:5000, Cat #: A0170-1ML, Sigma, USA) at room temperature for 1 h. The ELISA plate was added with freshly prepared Ultra-TMB (Cat #: 555214, BD, USA) for 5-min color development, and the absorbance of each well was read on a microplate reader (SpectraMaxR i3X, Molecular Devies, USA) at 450 nm.

The chimeric CD3-19 antibody's cross reaction to monkey CD3ε was tested by direct ELISA. Briefly, a 96-well ELISA plate was coated with 100 µl 500 ng/ml monkey CD3ε-his (Cat #: 90047-C08H, SinoBiological, China) for each well overnight at 4° C. Then, each well was blocked with 200 l blocking buffer (PBS+1% BSA+1% goat serum+ 0.05% Tween 20) at room temperature for 2 h, and then added and incubated with 100 µl serially diluted anti-CD3 antibodies (starting at 40 µg/ml) at room temperature for 1 h. The ELISA plate was then added and incubated with HRP conjugated goat anti-human IgG (1:5000, Cat #: A0170-1ML, Sigma, USA) at room temperature for 1 h. The ELISA plate was added with freshly prepared Ultra-TMB (Cat #: 555214, BD, USA) for 5-min color development, and the absorbance of each well was read on a microplate reader (SpectraMaxR i3X, Molecular Devies, USA) at 450 nm. An anti-HEL isotype control antibody (Cat #: LT12031, LifeTein, USA) was used a negative control. The results were shown in FIG. 1.

The chimeric CD3-19 antibody's binding capability to TCR/CD3 complexes on T cell surfaces was tested by FACS using $CD4^+$ T cells. Briefly, PBMCs from a healthy human donor's blood sample were collected by density gradient centrifugation and then re-suspended in RPMI1640 medium. $CD4^+$ T cells were isolated from the PBMCs using Invitrogen Dynabeads Untouched Human $CD4^+$ T cells isolation kit (Cat #: 11346D, Thermal Fisher Scientific, USA). Then, T cells were seeded at $1\times10^5$ cells/well on a 96 well plate, to which 100 µl serially diluted anti-CD3 antibodies were added then. After 1-h incubation at 4° C., the 96 well plate was rinsed by PBS for three times, and added with PE-Goat anti-Human IgG (H+L) (1:500, Cat #: PA1-86078, Thermo, USA). After 1-h incubation at 4° C., the 96 well plate was rinsed by PBS for three times, and then measured for cell fluorescence using a FACS machine (BD). An anti-HEL isotype control antibody (Cat #: LT12031, LifeTein, USA) was used a negative control. The results were shown in FIG. 2.

As shown in FIG. 1, the chimeric CD3-19 antibody was able to specifically bind human and monkey CD3ε proteins.

Figure 2:
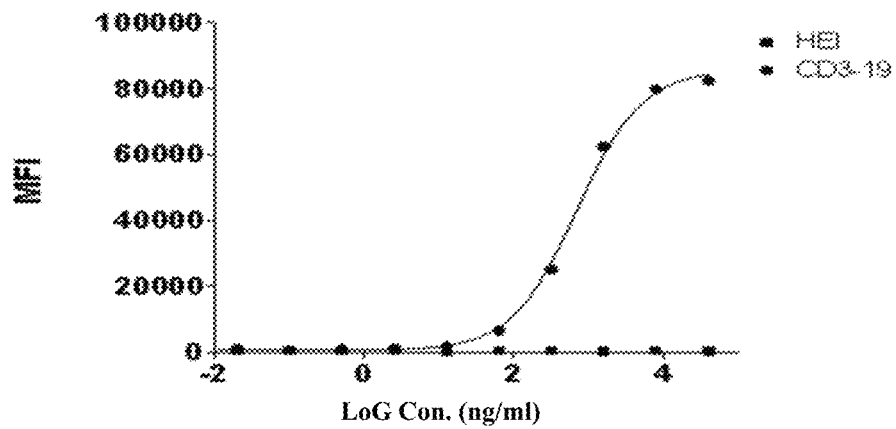
FIG. 2 shows the binding activity of CD3-19 to human CD3$^+$ T cells.

According to FIG. 2, the antibody CD3-19 was capable of binding human $CD4^+$ T cells with high binding specificity and activity.

Example 4 Affinity Maturation of CD3-19 by Phage Display

To further improve the binding affinity, CD3-19 was subject to affinity maturation by phage display techniques. Briefly, three-dimensional structural modeling simulation was performed to identify amino acid residues in the heavy and light chain CDRs of CD3-19 that might be important for binding affinity. The CDR residues as identified were subject to mutagenesis by PCRs using specially designed primers and standard protocol for site-directed mutagenesis. A phage display library was then constructed and subject to biopanning using beads coupled with human CD3ε-his proteins, following the protocol of Example 1.

After 3 rounds of biopanning, high binders were selected, harvested and then used to infect bacterial cells. Bacterial colonies were picked up and grown onto 96-well plates, and ELISA was then used to identify the high binders which were sequenced later. The beneficial mutations in the heavy and light chain CDRs were identified and then combined into a new phage display library, which were subject to another 3 rounds of biopanning and enrichments followed by sequencing confirmation as described above.

Three scFv antibodies were identified with higher binding capabilities than the parent antibody CD3-19, and designated as 19-15, 19-26 and 19-37, whose variable region sequence ID numbers were listed in Table 1.

Example 5 Expression, Purification and Binding Capability Characterization of Antibodies Obtained in Affinity Maturation The three scFv antibodies as screened above were expressed in HEK293F cells as full length, human IgG1/ kappa antibodies, the IgG1 constant region and the kappa constant region sequences were set forth in SEQ ID NOs: 22 (X1=L, X2=L, X3=N, X4=P) and 23, respectively. The expression and purification were performed using the protocol of Example 2.

The binding capabilities of CD3-19, 19-15, 19-26 and 19-37 to human CD3ε-his and monkey CD3ε-his were tested by ELISA following the protocol of Example 3. The results were shown in FIG. 3. These antibodies' binding capabilities to the human TCR/CD3 complexes on primary T cell surfaces were tested by FACS following the protocol of Example 3. The results were shown in FIG. 4.

Figure 3:
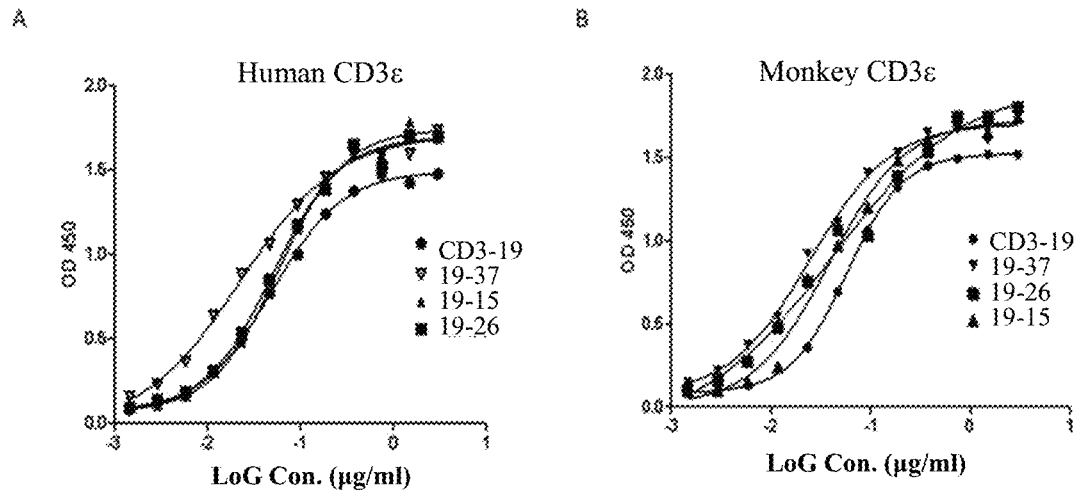
FIG. 3 shows the binding activities of affinity-maturated antibodies to human CD3ε (A) and monkey CD3ε (B).

As shown in FIG. 3, all three antibodies obtained in affinity maturation showed higher binding capabilities to human and monkey CD3ε than the parent antibody CD3-19.

Figure 4:
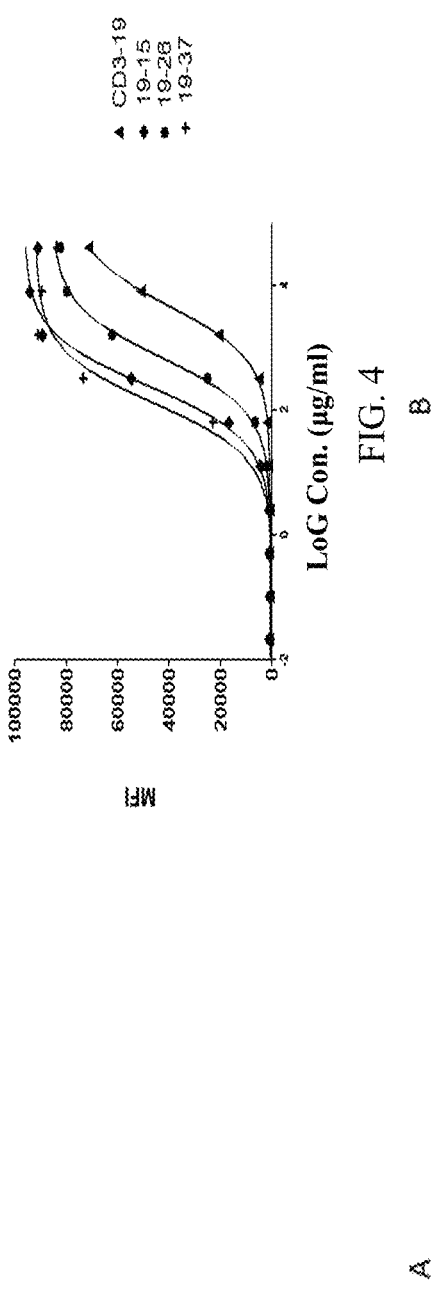
FIG. 4 shows the binding activities of affinity-maturated antibodies to human CD3$^+$ T cells.

Further, as shown in FIG. 4, the affinity maturated antibodies 19-15, 19-26 and 19-37 showed higher binding capabilities to the primary T cells than the parent antibody.

Example 6 Binding Affinity Determination of Anti-CD3 Antibodies by SPR

The binding affinities of the chimeric anti-CD3 antibodies to human and monkey CD3ε were measured by BIAcorem 8K (GE Life Sciences, USA).

Briefly, 100-200 response units (RU) of human CD3ε-his (Cat #: 10977-H08s, Sino Biological, China) or monkey CD3ε-his (Cat #: 90047-C08H, Sino Biological, China) were coupled to CM5 biosensor chips (Cat #: BR-1005-30, GE Life Sciences), followed by blocking of un-reacted groups with 1M ethanolamine. Serially diluted antibodies at concentrations ranging from 0.3 μM to 10 μM were injected into the SPR running buffer (HBS-EP buffer, pH7.4, Cat #:BR-1006-69, GE Life Sciences, USA) at 30 μL/minute. The binding affinities were calculated with the RUs of blank controls deducted. The association rate ($k_a$) and dissociation rate ($k_d$) were calculated using the one-to-one Langmuir binding model (BIA Evaluation Software, GE Life Sciences). The equilibrium dissociation constant $K_D$ was calculated as the $k_d/k_a$ ratio. The antibody of Macrogenics, mAB2, used as the positive control, was prepared using the variable regions disclosed in CN107827985A plus human IgG1/kappa constant regions (SEQ ID NOs: 22 (X1=L, X2=L, X3=N, X4=P) and 23).

The binding affinities of the anti-CD3 antibodies to human CD3ε and monkey CD3ε were determined and summarized in Table 2 and 3.

As shown in Table 2 and 3, the antibodies obtained in affinity maturation had higher binding affinities than the parent antibody, which were comparable to or higher than that of mAB2. Among the antibodies, 19-37 showed the highest binding affinity.

TABLE 2

Binding affinities of anti-CD3 antibodies to human CD3ε

|  | mAB2 | CD3-19 | 19-15 | 19-26 | 19-37 |
|---|---|---|---|---|---|
| $k_a$ | 5.24E+05 | 1.19+05 | 2.29+05 | 2.74E+05 | 1.92E+06 |
| $k_d$ | 8.10E-05 | 2.63E-05 | 3.27E-05 | 5.05E-05 | 1.21E-05 |
| $K_D$ | 1.54E-10 | 2.22E-10 | 1.43E-10 | 1.84E-10 | 6.28E-12 |

TABLE 3

Binding affinities of anti-CD3 antibodies to monkey CD3ε

|  | mAB2 | CD3-19 | 19-15 | 19-26 | 19-37 |
|---|---|---|---|---|---|
| $k_a$ | 7.67E+05 | 1.08E+05 | 3.16E+05 | 2.69E+05 | 1.23E+06 |
| $k_d$ | 9.80E-05 | 3.76E-05 | 7.32E-05 | 6.38E-05 | 4.68E-06 |
| $K_D$ | 1.28E-10 | 3.47E-10 | 2.32E-10 | 2.37E-10 | 3.79E-12 |

Example 7 Anti-CD3 Antibodies' Regulatory Effects on T Cell Activity

The chimeric anti-CD3 antibodies of the disclosure were tested for their effects on CD3/TCR signaling when antibody cross-linking occurred, using primary human T cells.

Briefly, a 96-well cell culture plate was coated with 100 μl 5 μg/ml F(ab')$_2$-Goat anti-Human IgG Fc gamma Secondary Antibody (Cat #: 31163, Invitrogen, USA) for each well at 4° C. overnight. Each well was rinsed with PBS twice, and added and incubated with 100 μl anti-CD3 antibodies at different concentrations at 37° C. for 2 h. Meanwhile, PBMCs from a healthy human donor's blood sample were collected by density gradient centrifugation, and CD4$^+$ T cells were isolated from the PBMCs using Invitrogen Dynabeads Untouched Human CD4$^+$ T cell isolation kit (Cat #: 11346D, Thermal Fisher Scientific, USA) according to the manufacturer's instruction. The CD4$^+$ T cells were re-suspended in RPMI complete media at a cell density of 1.0×10$^6$/ml, and labeled with 2.5 μM carboxyfluorescein succinimidyl ester (CFSE, Cat #: C34554I, Invitrogen, USA) by incubation at 37° C. for 10 min. The cells were re-suspended in RPMI complete media (RPMI+10% FBS) at a viable cell density of 2.5×10$^5$/ml. Then, 200 μl of the T cell suspensions were added to the anti-CD3 coated plate, and incubated at 37° C. with 5% CO$_2$ for 72 h. The CSFE staining was measured by FACS, to determine cell proliferation rates. The antibody mAB2 was used as the positive control. The results were shown in FIG. 5 (A).

In addition, the free chimeric anti-CD3 antibodies were tested for their effects on T cell activation, where no antibody cross-linking occurred. Briefly, PBMCs from a healthy human donor's blood sample were collected by density gradient centrifugation, and CD4$^+$ T cells were isolated from the PBMCs using Invitrogen Dynabeads Untouched Human CD4+ T cell isolation kit (Cat #: 11346D, Thermal Fisher Scientific, USA) according to the manufacturer's instruction. The CD4$^+$ T cells were re-suspended in RPMI complete media at a cell density of 1.0×10$^6$/ml, and labeled with 2.5 μM carboxyfluorescein succinimidyl ester (CFSE, Cat #: C34554I, Invitrogen, USA) by incubation at 37° C. for 10 min. The labeled cells were re-suspended in RPMI complete media (RPMI+10% FBS) at a viable cell density of 5×10$^5$/ml. Then, 100 μl of the T cell suspensions were added to a 96 well cell culture plate with 100 μl anti-CD3 antibodies at different concentrations, and the plate was incubated at 37° C. with 5% CO$_2$ for 72 h. The CSFE staining was measured by FACS, to determine cell proliferation rates. The antibody mAB2 was used as the positive control. The results were shown in FIG. 5 (B).

Figure 5:
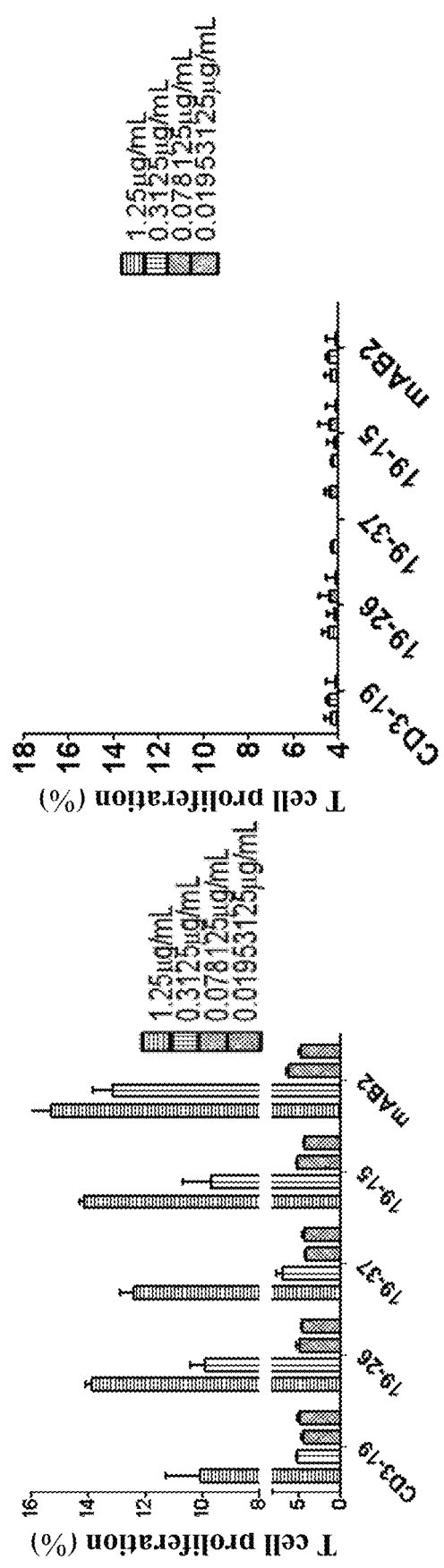
FIG. 5 shows the effects of CD3-19 and the affinity-maturated antibodies, when bound to secondary antibodies (to enable antibody cross-linking) (A) or not (B), on T cell proliferation.

As shown in FIG. 5 (A), the anti-CD3 antibodies, when bound to the secondary antibodies coated on the plate to render antibody cross-linking, were able to increase T cell proliferation in a dose dependent manner, and the antibodies obtained by affinity maturation showed higher such effects than the parent antibody. However, the effects of the anti-CD3 antibodies of the disclosure on T cell activation were all lower than that of mAB2, meaning that the anti-CD3 antibodies of the disclosure had comparable or higher binding capabilities/affinities but lower activities on T signaling activation compared to the positive antibody mAB2. In other words, despite of the high binding capabilities to T cells, the anti-CD3 antibodies of the disclosure would not cause excess CD3 signaling, thus reducing potential toxicities such as excess cytokine release induced by T cell activation.

Further, as shown in FIG. 5 (B), the free anti-CD3 antibodies, as lack of antibody cross-linking, showed no effect on T cell proliferation.

Example 8 Humanization of Exemplary Anti-CD3 Antibodies

On the basis of the functional assays above, 19-15 and 19-26 were selected for humanization and further characterization. Humanization was conducted using the well-established CDR-grafting method as described in e.g., U.S. Pat. No. 5,225,539 and specified in detail as follows.

To screen acceptor frameworks for humanization of 19-15, the light and heavy chain variable chain sequences of this antibody were blasted against the human immunoglobulin gene database in NCBI website (ncbi.nlm.nih.gov) to identify the most homologous human germline IGVH and JGVX as the acceptor for humanizations, respectively. The human heavy chain acceptor as selected was IGHV3-23*05, and the human light chain acceptor as selected was IGLV7-43*01.

To screen acceptor frameworks for humanization of 19-26, the light and heavy chain variable chain sequences of this antibody were blasted against the human immunoglobulin gene database in NCBI website (ncbi.nlm.nih.gov) to identify the most homologous human germline IGVH and JGVX as the acceptor for humanizations, respectively. The human heavy chain acceptor as selected was IGHV3-23*05, and the human light chain acceptor as selected was IGLV7-43*01.

Three dimensional structures of the variable domains of the 2 antibodies were modeled in order to identify key framework residues that might play important roles in supporting CDR loop structures, thus designing back mutations in the humanized antibodies. Selected structure templates had the same classes of canonical loop structures in L-CDR1, L-CDR2, L-CDR3, H-CDR1, H-CDR2 and H-CDR3 to 19-15 and 19-26, respectively. Using the structural templates selected, structural models were built by replacing the murine frameworks with human acceptor's frameworks for heavy and light chains. Three-dimensional structural modeling simulation was then performed to identify key framework residues that might be important in supporting the CDR-loop structures or the heavy and light chain interface. When both the murine antibody framework and the human acceptor framework share the same residue at a certain site, the human germline residue was kept. On the other hand, when the murine antibody framework and human germline acceptor framework have different residues at a certain site, the importance of this residue was evaluated by structural modeling. If a residue in the murine antibody's framework was found to interact with and influence the CDR residues, then this residue was back-mutated to murine residue. Table 4 below listed structural templates used in antibody structure simulation.

TABLE 4

Structural templates used in antibody structure simulations

| Antibody chain | PDB code of template structure | Sequence identity | Sequence similarity |
|---|---|---|---|
| 19-15 heavy chain | 5FCS | 89% | 97% |
| 19-15 light chain | 1A6V | 94% | 95% |
| 19-26 heavy chain | 5FCS | 90% | 98% |
| 19-26 light chain | 1A6V | 95% | 97% |

Based on the structural modeling as described above, 5 potential back-mutations (S49A, A99V, N76D, V95M, and K100R) were identified for heavy chain of 19-15 and 7 potential back-mutations (F38V, Y51G, T2A, Q44H, P46F, A48G, and T60V) were identified for the light chain; 5 potential back-mutations (S49A, A99V, N76D, V95M, and K100R) were identified for heavy chain of 19-26 and 7 potential back-mutations (F38V, Y51G, T2A, Q44H, P46F, A48G, and T60V) were identified for the light chain.

As summarized in Table 1, 2 humanized heavy chain variable regions and 2 humanized light chain variable regions were designed for 19-15, and a total of 4 exemplary humanized antibodies were obtained. For 19-26, 2 humanized heavy chain variable regions and 1 humanized light chain variable region were designed, and a total of 2 exemplary humanized antibodies were obtained.

Sequences encoding the humanized heavy/light chain variable region plus human IgG1/kappa constant regions (SEQ ID NOs: 22 (X1=L, X2=L, X3=N, X4=P) and 23) were synthesized and then subcloned into the expression vector pCDNA3.1(+) (Invitrogen, USA) using the BamHI and XhoI restriction sites, respectively. All expression constructs were confirmed by sequencing. The 6 humanized anti-CD3 antibodies were transiently expressed according to the protocol as described in Example 2. And the humanized antibodies were purified according to Example 2.

Example 9 Exemplary Humanized Anti-CD3 Antibodies' Binding Capabilities/Affinities to Human and Monkey CD3

The humanized anti-CD3 antibodies' binding capabilities to human and monkey CD3ε proteins were measured by ELISA according to the protocol in Example 3. The results were shown in FIG. 6.

The humanized antibodies were further tested for their binding capabilities to human T cells by FACS, using the protocol of Example 3. The results were shown in FIG. 7.

The humanized anti-CD3 antibodies' binding affinities to human and monkey CD3ε proteins were measured by SPR according to the protocol in Example 6. The results were summarized in Table 5 and Table 6.

Figure 6:
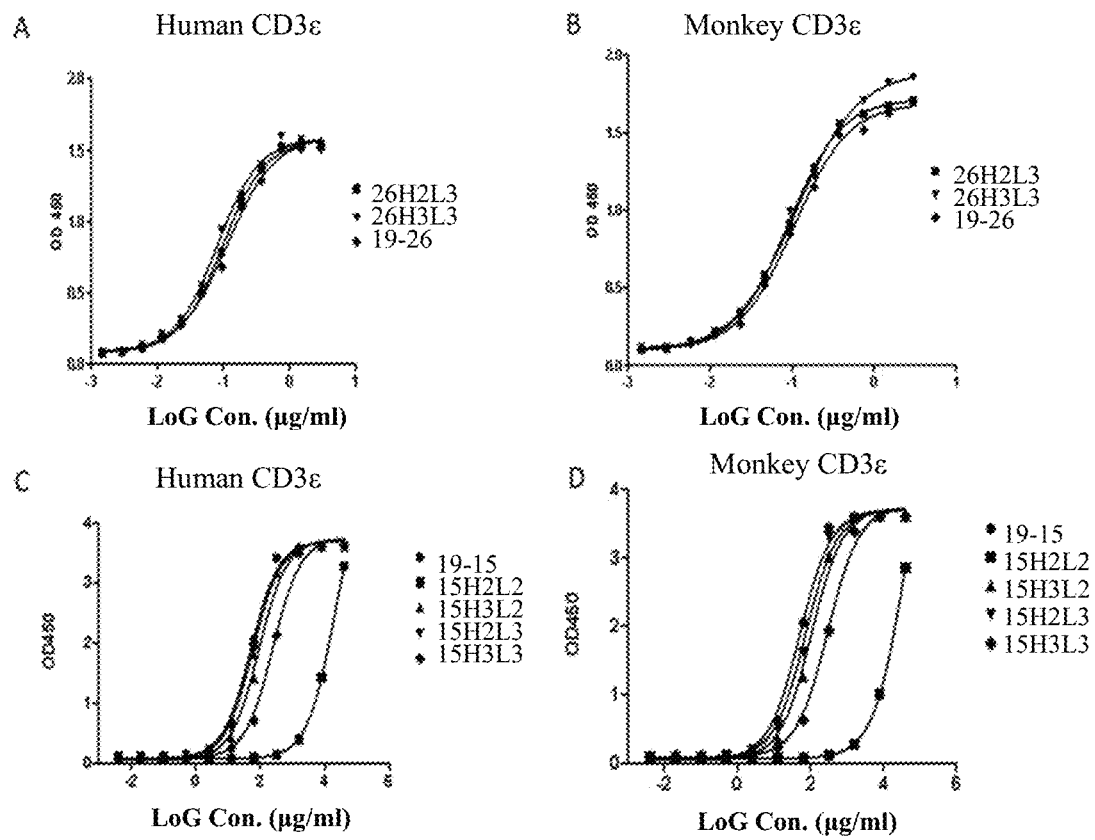
FIG. 6 shows the binding activities of humanized 19-26 antibodies to human CD3ε (A) and monkey CD3ε (B), and binding activities of humanized 19-15 antibodies to human CD3ε (C) and monkey CD3ε (D).

As shown in FIG. 6, all the exemplary humanized antibodies retained binding capabilities to human CD3ε protein (FIGS. 6 (A) and 6 (C)), and to monkey CD3ε protein (FIGS. 6 (B) and 6 (D)).

Figure 7:
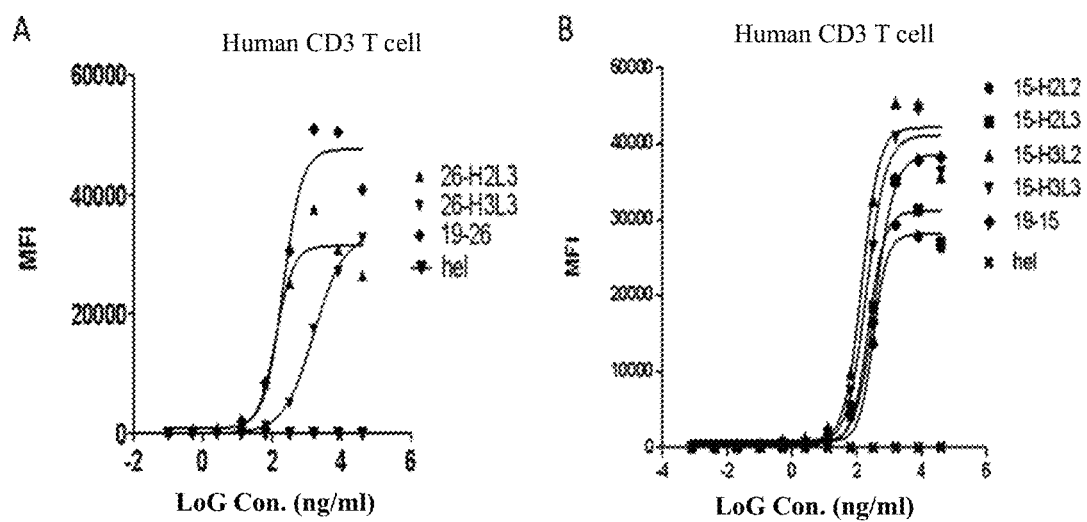
FIG. 7 shows the binding activities of humanized 19-26 antibodies (A) and humanized 19-15 antibodies (B) to human CD3$^+$ T cells.

As shown in FIG. 7, all the exemplary humanized antibodies retained binding capabilities to human T cells.

TABLE 5

Binding affinities of humanized anti-CD3 antibodies to human CD3ε

|  | mAb | $k_a$ | $k_d$ | $K_D$ |
|---|---|---|---|---|
| 1 | 15-H2L2 | 1.25E+06 | 6.64E−04 | 5.16E−10 |
| 2 | 15-H2L3 | 3.43E+06 | 3.58E−04 | 1.04E−10 |

TABLE 5-continued

Binding affinities of humanized anti-CD3 antibodies to human CD3ε

| | mAb | $k_a$ | $k_d$ | $K_D$ |
|---|---|---|---|---|
| 3 | 15-H3L2 | 8.03E+05 | 1.65E−04 | 2.05E−10 |
| 4 | 15-H3L3 | 1.39E+06 | 1.34E−04 | 9.67E−11 |
| 5 | 26-H2L3 | 9.44E+05 | 3.77E−03 | 3.95E−09 |
| 6 | 26-H3L3 | 1.94E+05 | 1.68E−04 | 8.64E−10 |

TABLE 6

Binding affinities of humanized anti-CD3 antibodies to monkey CD3ε

| | mAb | $k_a$ | $k_d$ | $K_D$ |
|---|---|---|---|---|
| 1 | 26-H3L3 | 1.18E+06 | 2.26E−04 | 1.92E−10 |
| 2 | 26-H2L3 | 1.26E+06 | 2.86E−03 | 2.27E−09 |
| 3 | 15-H2L3 | 7.98E+06 | 6.20E−03 | 7.77E−10 |
| 4 | 15-H3L2 | 2.02E+05 | 1.20E−04 | 5.91E−10 |
| 5 | 15-H3L3 | 2.38E+05 | 1.47E−04 | 6.16E−10 |
| 6 | 15-H2L2 | 3.59E+04 | 2.10E−04 | 5.84E−09 |

According to Table 5, all the exemplary humanized antibodies retained high binding affinities to human CD3 proteins. It can be seen from Table 6 that all the exemplary humanized antibodies retained cross-reactions to monkey CD3 proteins.

Example 10 Exemplary Humanized Anti-CD3 Antibodies Induced T Cell Activity

The effects of exemplary humanized antibodies on CD3/TCR signaling were tested when antibody cross-linking occurred, using primary human T cells, according to the protocol of Example 7 with minor modifications. Briefly, a 96-well cell culture plate was coated with 100 μl 5 μg/ml F(ab')2-Goat anti-Human IgG Fc gamma Secondary Antibody (Cat #: 31163, Invitrogen, USA) for each well at 4° C. overnight. Each well was rinsed with PBS twice, and added and incubated with 100 μl anti-CD3 antibodies at different concentrations at 37° C. for 2 h. Meanwhile, PBMCs from a healthy human donor's blood sample were collected by density gradient centrifugation, and CD4+ T cells were isolated from the PBMCs using Invitrogen Dynabeads Untouched Human CD4+ T cell isolation kit (Cat #: 11346D, Thermal Fisher Scientific, USA) according to the manufacturer's instruction. The CD4+ T cells were re-suspended at a viable cell density of 2.5×10$^5$/ml. Two hundred μl of the T cell suspensions were added to the anti-CD3 coated plate, and incubated at 37° C. with 5% $CO_2$ for 24 h. Fifty μl of cell culture supernatants were used for IFN-γ level measurement using an ELISA kit (Cat #: SIF50, R&D, USA), according to the manufacturer's instruction. The cells were further cultured for 48 h, collected, rinsed by PBS for three times, and incubated with 2 μl PE Mouse anti-Human CD69 antibody (Cat #: 555531, BD, USA) and 2 μl FITC Mouse anti-Human CD4 antibody (Cat #: 561842, BD, USA) at room temperature for 30 min. The cells were collected with centrifugation, rinsed by PBS for three times, and measured by FACS for the ratio of CD69+CD4+ T cells to CD4+ T cells by flow cytometry, so as to determine the effect of the antibodies on T cell activation when antibody cross-linking occurred. The assay was done in triplicate, and mAB2 was used as the positive control. The results were shown in FIG. 8.

The free antibodies' effects on T cell activation were also assayed. Briefly, PBMCs from a healthy human donor's blood sample were collected by density gradient centrifugation, and CD4+ T cells were isolated from the PBMCs using Invitrogen Dynabeads Untouched Human CD4+ T cell isolation kit (Cat #: 11346D, Thermal Fisher Scientific, USA) according to the manufacturer's instruction. The CD4+ T cells were re-suspended in RPMI complete media at a cell density of 5×10$^5$/ml. One hundred μl of the T cell suspensions were added to the cell culture plate, to which added 100 μl of the anti-CD3 antibodies at different concentrations. After incubation at 37° C. with 5% $CO_2$ for 24 h, 50 μl of cell culture supernatants were used for IFN-γ level measurement using an ELISA kit (Cat #: SIF50, R&D, USA), according to the manufacturer's instruction. The cells were further cultured for 48 h, collected, rinsed by PBS for three times, and incubated with 2 μl PE Mouse anti-Human CD69 antibody (Cat #: 555531, BD, USA) and 2 μl FITC Mouse anti-Human CD4 antibody (Cat #: 561842, BD, USA) at room temperature for 30 min. The cells were collected with centrifugation, rinsed by PBS for three times, and measured by FACS for the ratio of CD69+CD4+ T cells to CD4+ T cells, so as to determine the effect of the free antibodies on T cell activation. The assay was done in triplicate, and mAB2 was used as the positive control. The results were shown in FIG. 9.

Figures 8, 9:
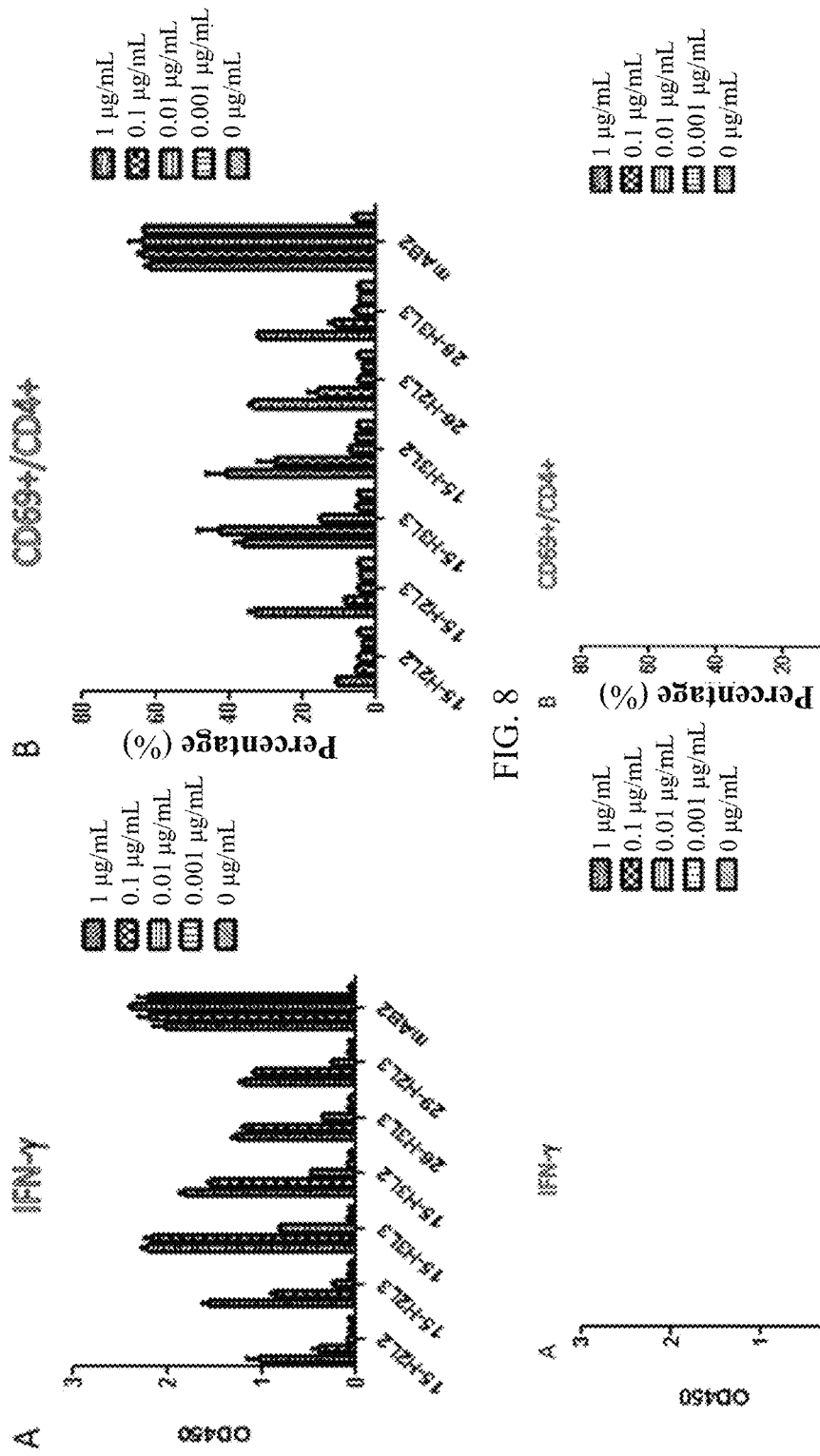
FIG. 8 shows the capabilities of the humanized antibodies, when bound to secondary antibodies (to enable antibody cross-linking), to activate T cells as measured by interferon-γ (IFN-γ) release (A) and CD69 expression (B).
FIG. 9 shows the capabilities of the humanized antibodies, when unbound to secondary antibodies, to activate T cells as measured by IFN-γ release (A) and CD69 expression (B).

As shown in FIG. 8, when antibody cross-linking occurred, all the exemplary humanized antibodies were able to activate T cells, inducing interferon γ release, and up-regulating CD69 expression on T cell surfaces. While free antibodies, as shown in FIG. 9, had no effects on T cell activities, i.e., they did not affect interferon γ release or CD69 expression. These results suggested that, the humanized antibodies' effects on T cell activation depended on antibody cross-linking, and all the exemplary humanized antibodies induced significantly less T cell activation and cytokine release than the positive control.

Example 11 Construction of HEK293A Cell Lines Stably Expressing Human or Monkey Proteins Cell lines stably expressing human CD20, monkey CD20, human CD16A, human CD32A, human CD32B or human CD64, were constructed using HEK293A cells. Briefly, sequences encoding human CD20, monkey CD20, human CD16A, human CD32A, human CD32B, and human CD64 (SEQ ID NOs: 35, 36, 37, 38, 39 and 40, respectively) were synthesized, and then subcloned into pLV-EGFP(2A)-Puro vectors (Beijing Inovogen, China) between the restriction sites EcoRI and BamHI. Lentiviruses were generated in HEK293T cells (Cobioer, NJ, China) by cotransfection of the resultant expression vectors, psPAX and pMD2.G plasmids, according to the instruction in Lipofectamine 3000 kit (Thermo Fisher Scientific, USA). Three days post cotransfection, the lentiviruses were harvested from the HEK293T cell culture supernatants, and then used to infect HEK293A cells to generate HEK293A cell lines stably expressing human CD20, monkey CD20, human CD16A, human CD32A, human CD32B or human CD64, namely HEK293A/human CD20, HEK293A/monkey CD20, HEK293A/human CD16A, HEK293A/human CD32A, HEK293A/human CD32B, and HEK293A/human CD64, respectively. Transfected HEK293A cells were cultured in DMEM (Cat #: SH30022.01, Gibco, USA) containing 10% FBS (Cat #: FND500, Excell, China) and 0.2 μg/ml puromycin (Cat #: A11138-03, Gibco) for 7 days. The expressions of human CD20, monkey CD20, human CD16A, human CD32A, human CD32B and human CD64 were confirmed by FACS using commercially available anti-human/monkey CD20 antibody (PE anti-Human CD20 Antibody, Cat #: E-AB-F1045D, Elabscience, China), anti-human CD16A antibody (PE anti-Human CD16 Antibody, Cat #: E-AB-F1005D, Elabscience, China), anti-human CD32A antibody (PE Anti-CD32B+CD32A antibody, Cat #: ab30357, abeam, USA), anti-human CD32B antibody (PE Anti-CD32B+CD32A antibody, Cat #: ab30357, abeam, USA), and anti-human CD64 antibody (PE/Cy5 Anti-CD64 antibody, Cat #: ab192338, abeam, USA).

Example 12 Functional Modifications at Anti-CD3 Antibodies' Fc Regions

To reduce CD3 signaling activation and T cell activation caused by anti-CD3 antibodies when they bound to FcRs via their Fc regions, the Fc regions were modified to decrease their binding affinities to each FcR isotype.

The anti-CD3 antibody 15H3L3 was engineered to have wild-typed heavy chain IgG1 constant region (SEQ ID No: 22, X1=L, X2=L, X3=N, X4=P), IgG1 constant region with L234A/L235A mutations (SEQ ID NO:22, X1=A, X2=A, X3=N, X4=P), IgG1 constant region with L234A/L235A/P329G mutations (SEQ ID NO:22, X1=A, X2=A, X3=N, X4=G), IgG1 constant region with L234A/L235A/N297A mutations (SEQ ID NO:22, X1=A, X2=A, X3=A, X4=P), or IgG1 constant region with L234A/L235A/N297A/P329G mutations (SEQ ID NO:22, X1=A, X2=A, X3=A, X4=G), and human λ light chain constant region of SEQ ID: 32. The resultant full-length antibodies were designated as 15H3L3-WT, 15H3L3-LL, 15H3L3-LLP, 15H3L3-LLN, and 15H3L3-LLNP, respectively.

The sequences encoding the variable regions and constant regions were inserted into pCDNA3.1 plasmids (Invitrogen, USA) between XhoI and BamHI sites to construct expression vectors. HEK-293F cells were transfected with the resulting vectors using PEI. Briefly, HEK-293F cells were cultured in Free Style™ 293 Expression Medium (Cat #: 12338-018, Gibco), and transfected with the expression vectors using polyethyleneinimine (PEI) at a DNA:PEI ratio of 1:3. The concentration of DNAs used for transfection was 1.5 µg per milliliter cell culture. Transfected HEK-293F cells were cultured in an incubator in 5% $CO_2$ at 37° C. with shaking at 120 RPM. After 10-12 days, cell culture supernatants were harvested, and subject to centrifugation at 3500 rpm for 5 minutes and then to filtration using 0.22 µm films to remove cell debris. Monoclonal antibodies were then purified and enriched using a pre-equilibrated Protein-A affinity column (Cat #:17040501, GE, USA) and eluted with the elution buffer (20 mM citric acid, pH3.0-3.5). The purified antibodies were kept in PBS buffer (pH 7.0) and the concentration was determined using a NanoDrop instrument.

The purified monoclonal antibodies' binding capabilities to CD16A, CD32A, CD32B and CD64 were tested using the HEK293 cells constructed in Example 11 stably expressing human CD16A, CD32A, CD32B and CD64 respectively by FACS. Briefly, 105 HEK293A cells in 50 µl culture media were seeded on a 96-well plate, to which 50 µl serially diluted 15H3L3 antibodies were added. After 1 h incubation at 4° C., the 96 well plate was rinsed by PBST for three times, added with PE-F(ab')2-Goat anti-Human IgG Fc Secondary Antibody (1:500, Cat #: H10104, Life Technologies, USA). After 1 h incubation at 4° C., the 96-well plate was rinsed by PBS for three times, and measured for cell fluorescence using a FACS machine (BD). The results were shown in FIG. 10.

The purified monoclonal antibodies were tested for their binding capabilities to the CD3 complex using Jurkat cells (Cat #: CBP60520, Nanjing Co-Bioer, China) by FACS. Briefly, 105 Jurkat cells in 50 µl culture media were seeded on a 96-well plate, to which 50 µl serially diluted 15H3L3 antibodies were added then. After 1 h incubation at 4° C., the 96 well plate was rinsed by PBS for three times, added with PE-Goat anti-Human IgG (H+L) (1:500, Cat #: PA1-86078, Thermo, USA). After 1 h incubation at 4° C., the 96-well plate was rinsed by PBS for three times, and measured for cell fluorescence using a FACS machine (BD). The results were shown in FIG. 11.

The effects of free 15H3L3 antibodies on T cell activation were tested by measuring cytokine release and activation marker expression by T cells. PBMCs from a healthy human donor's blood sample were collected by density gradient centrifugation and then re-suspended in RPMI complete media (RPMI1640+10% FBS) at a cell density of $2.5 \times 10^5$/ml. The cell suspensions were plated onto a 96-well plate, 200 µl per well, to which 50 µl 15H3L3 antibodies at different concentrations were added. After 48 h incubation at 37° C. with 5% $CO_2$, cell culture supernatants were collected and measured for IFN-γ levels using an ELISA kit (Cat #: SIF50, R&D, USA). PBMCs were harvested, rinsed by PBS for three times, added with 2 µl PE Mouse Anti-Human CD69 antibody (Cat #:555531, BD, USA), 2 µl BV605 Mouse Anti-Human CD25 antibody (Cat #: 562660, BD, USA), and 2 µl FITC Mouse Anti-Human CD4 antibody (Cat #: 561842, BD, USA), incubated at room temperature for 30 min, centrifuged, rinsed by PBS for three times, and measured by FACS for the ratio of $CD69^+CD4^+$ T cells, $CD25^+CD4^+$ T cells, or the $CD69^+CD25^+CD4^+$ T cells to $CD4^+$ T cells. The results were shown in FIG. 12.

The effects of 15H3L3 antibodies with cross-linking on $CD4^+$ T cell activation were also tested by measuring cytokine release and activation marker expression by T cells. Briefly, a 96-well cell culture plate was coated with 100 µl 5 µg/ml F(ab')2-Goat anti-Human IgG Fc gamma Secondary Antibody (Cat #: 31163, Invitrogen, USA) for each well at 4° C. overnight. Each well was rinsed with PBS twice, and added and incubated with 100 µl 15H3L3 antibodies at different concentrations at 37° C. for 2 h. Meanwhile, PBMCs from a healthy human donor's blood sample were collected by density gradient centrifugation, and $CD4^+$ T cells were isolated from the PBMCs using Invitrogen Dynabeads Untouched Human CD4+ T cell isolation kit (Cat #: 11346D, Thermal Fisher Scientific, USA) according to the manufacturer's instruction. The $CD4^+$ T cells were re-suspended in RPMI complete media (RPMI1640+10% FBS) at a viable cell density of $2.5 \times 10^5$/ml. The cell suspensions were added to the anti-CD3 coated plate, 200 µl per well, and incubated for 48 h at 37° C. with 5% $CO_2$. Fifty µl of cell culture supernatants was collected per well and measured for IFN-γ levels using an ELISA kit (Cat #: SIF50, R&D, USA). Cells were harvested, rinsed by PBS for three times, added with 2 µl PE Mouse Anti-Human CD69 antibody (Cat #:555531, BD, USA), 2 µl BV605 Mouse Anti-Human CD25 antibody (Cat #: 562660, BD, USA), and 2 µl FITC Mouse Anti-Human CD4 antibody (Cat #: 561842, BD, USA), incubated at room temperature for 30 min, centrifuged, rinsed by PBS for three times, and measured by FACS for the ratio of $CD69^+CD4^+$ T cells, $CD25^+CD4^+$ T cells or $CD69^+CD25^+CD4^+$ T cells to $CD4^+$ T cells. The assay was done in triplicate, and the results were shown in FIG. 13.

Figure 10:
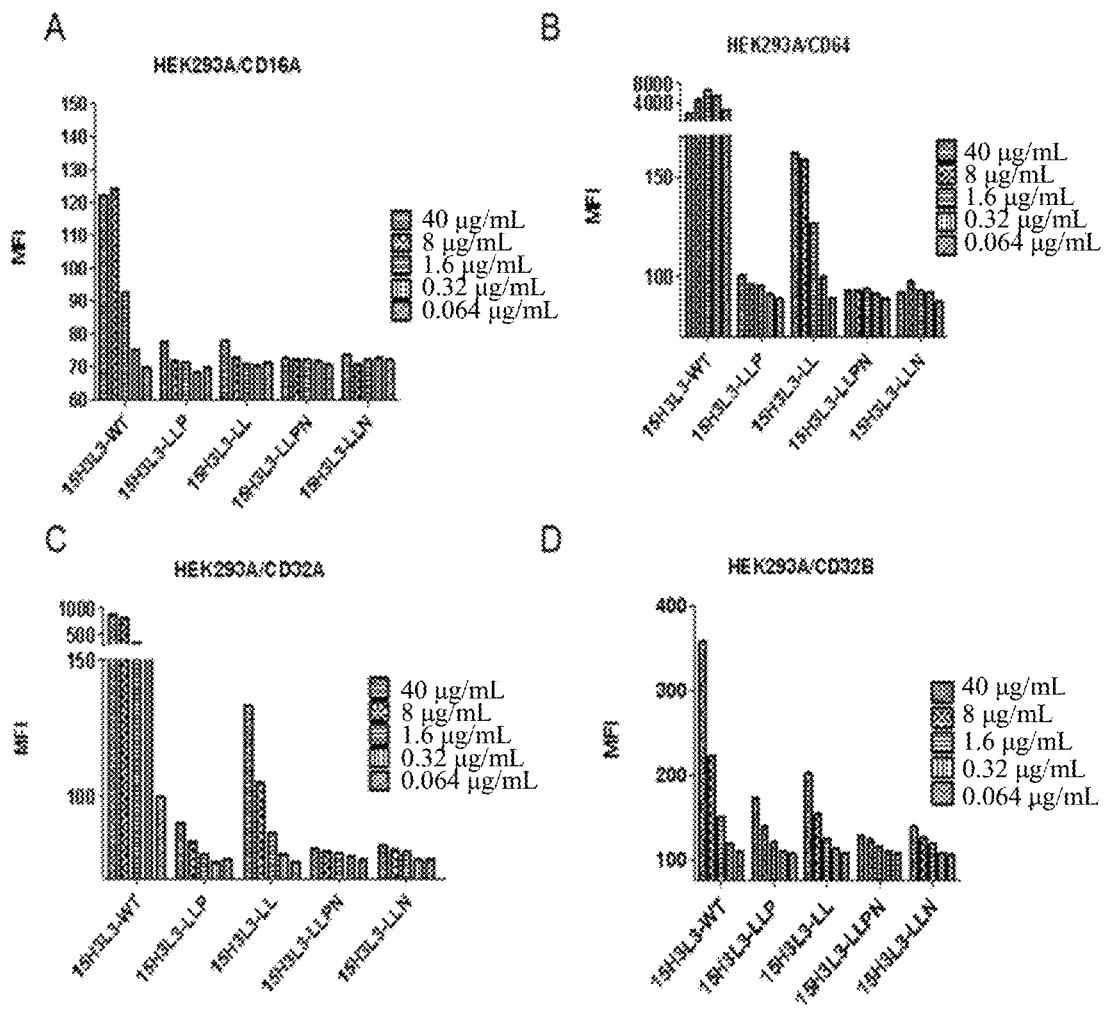
FIG. 10 shows the binding activities of humanized antibodies with mutated Fc regions to HEK293A/human CD16A (A), HEK293A/human CD64 (B), HEK293A/human CD32A (C) and HEK293A/human CD32B (D).

As shown in FIG. 10, all antibodies having mutations at Fc regions showed significantly lower binding capabilities to 4 FcRs than those with wild-typed Fc regions. Among these, 15H3L3-LLPN and 15H3L3-LLN' binding capabilities to CD16A, CD32A, CD32B and CD64 were almost below detection limits, 15H3L3-LLP retained weak binding capability to CD32A and CD32B, while 15H3L3-LL showed relatively high binding capability to CD64, CD32A and CD32B compared to other variants.

Figure 11:
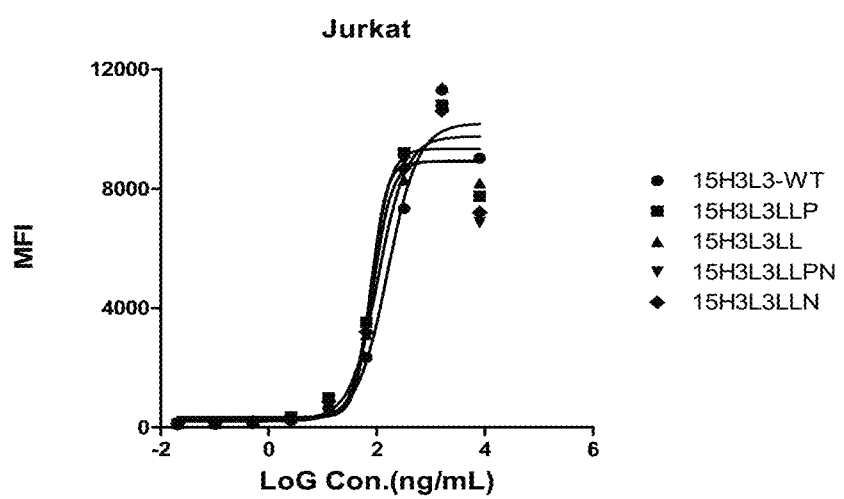
FIG. 11 shows the binding activities of humanized antibodies with mutated Fc regions to Jurkat cells.

According to FIG. 11, the mutations at the Fc regions had no effect on anti-CD3 antibodies' binding capabilities to CD3.

Figure 12:
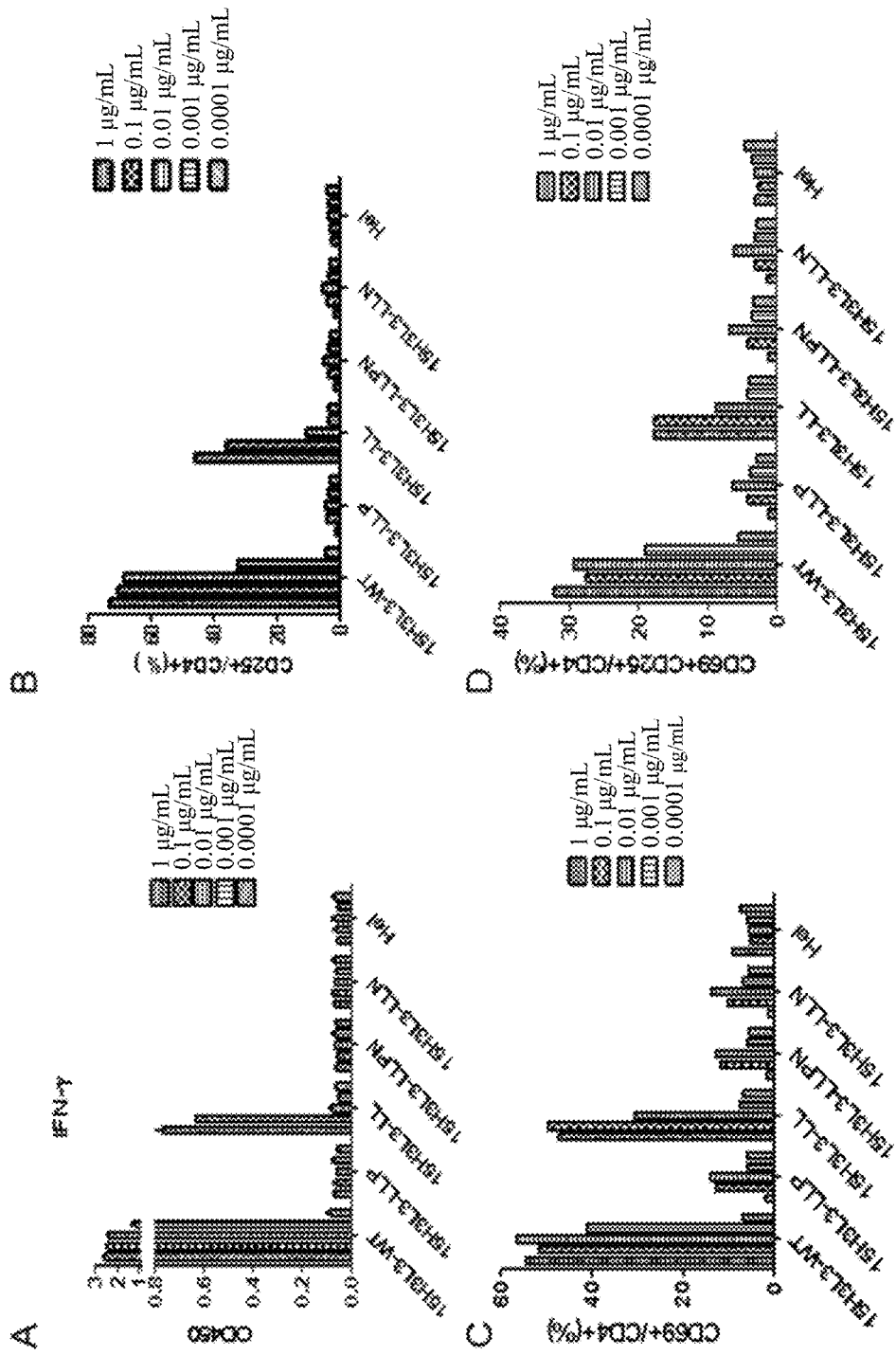
FIG. 12 shows the capabilities of the humanized antibodies with mutated Fc regions, when unbound to secondary antibodies, to induce IFN-γ release (A), CD25 expression (B), CD69 expression (C) and CD69+CD25 co-expression (D) by human PBMCs.

It can be seen in FIG. 12 that all antibodies with mutations at the Fc regions significantly decreased IFN-γ release and expressions of T cell maturation markers such as CD69 and CD25, compared to those with wild-typed Fc regions. Specifically, the cytokine (e.g., IFN-γ) release and T cell maturation marker (such as CD69 and CD25) expression were almost not detectable in PBMCs treated with 15H3L3-LLP, 15H3L3-LLPN, or 15H3L3-LLN, while 15H3L3-LL was able to induce cytokine (e.g., IFN-γ) release and T cell maturation marker (such as CD69 and CD25) expression to some extent.

Figure 13:
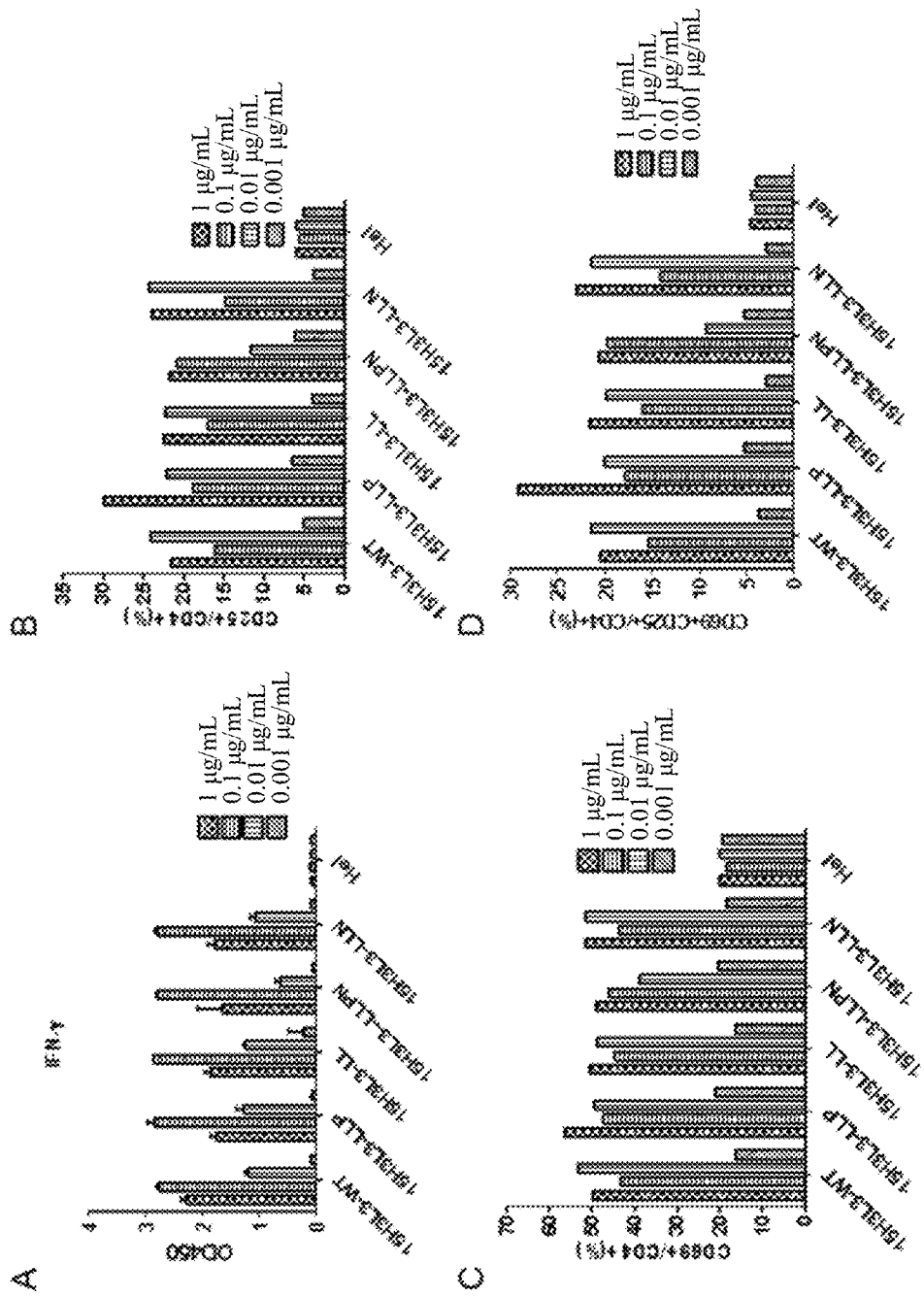
FIG. 13 shows the capabilities of the humanized antibodies with mutated Fc regions, when bound to secondary antibodies (to enable antibody cross-linking), to induce IFN-γ release (A), CD25 expression (B), CD69 expression (C) and CD69+CD25 co-expression (D) by human PBMCs.

Further, as shown in FIG. 13, the Fc region mutations did not change anti-CD3 antibodies' effects on T cell activation when antibody cross-linking occurred. In other words, when antibody cross-linking occurred via Fc regions bound to anti-Fc secondary antibodies, the anti-CD3 antibodies having mutant Fc regions were able to induce cytokine (e.g., IFN-γ) release and T cell maturation marker (such as CD69 and CD25) expression at comparable levels to those with wild-typed Fc regions.

Example 13 Construction and Expression of Bispecific Antibodies Against CD3 and CD20

Figure 14:
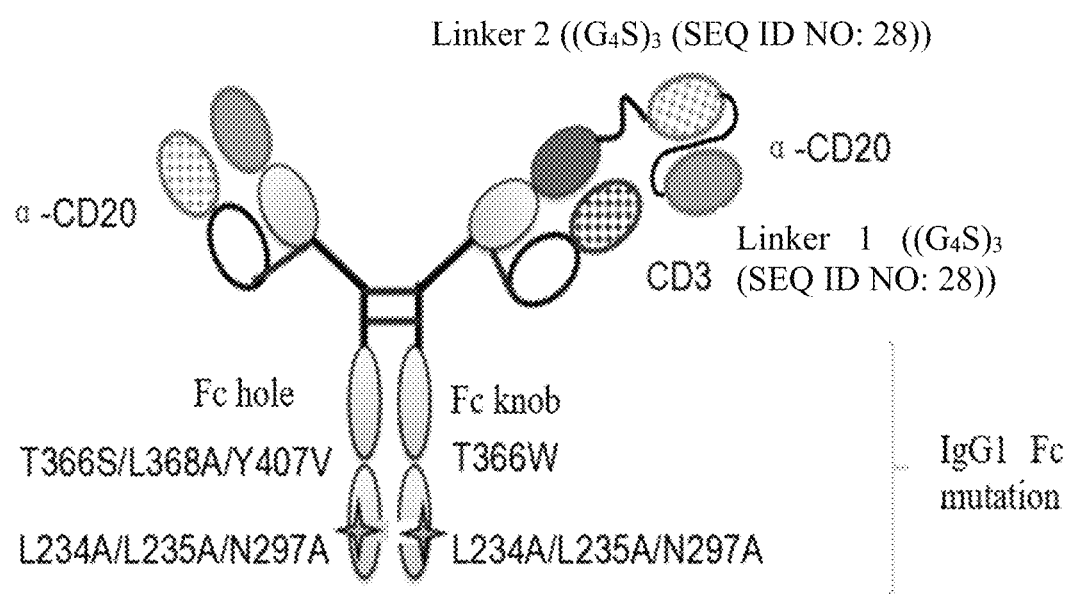
FIG. 14 is schematic diagram showing the structure of a bispecific antibody of the disclosure against CD3 and CD20.

A bispecific antibody was constructed in an asymmetrical format (CD20: CD3=2:1), with the structure shown in FIG. 14. The CD20 binding portion employed the heavy and light chain variable regions having amino acid sequences of SEQ ID NOs: 26 and 27, respectively (anti-CD20 antibody MIL62, see details in CN108138186B), and the CD3 binding portion used the heavy and light chain variable regions of 15H2L3 or 15H3L3. Three half-antibody fragments, i.e., MIL220 (containing the anti-CD20 heavy chain variable region of SEQ ID NO: 26, the heavy chain constant region with a hole of SEQ ID NO: 33, the anti-CD20 light chain variable region of SEQ ID NO: 27, and the light chain constant region of SEQ ID NO: 31), MIL221-1 (containing anti-CD20 VH-linker-anti-CD20 VL-linker-15H2L3 VH having the amino acid sequence of SEQ ID NO: 29, the heavy chain constant region with a knob of SEQ ID NO: 34, 15H2L3's light chain variable region of SEQ ID NO: 18, and the light chain constant region of SEQ ID NO: 32) and MIL221-2 (containing anti-CD20 VH-linker-anti-CD20 VL-linker-15H3L3 VH having the amino acid sequence of SEQ ID NO: 30, the heavy chain constant region with a knob of SEQ ID NO: 34, 15H3L3's light chain variable region of SEQ ID NO: 18, and the light chain constant region of SEQ ID NO: 32), were produced using GS-vectors as described in ZL200510064335.0.

Sequences encoding MIL220's VH, and MIL221-1 and MIL221-2's anti-CD20 scFv-linker-anti-CD3 VH were synthesized. The DNA fragments were digested with EcoRI and NheI, and then cloned to the vectors containing the heavy chain constant regions, respectively. The DNA sequences encoding the MIL220's VL, MIL221-1's VL and MIL221-2's VL were synthesized, digested with ClaI and BsiWI, and ligated to the vectors containing the light chain constant regions. The DNA sequences encoding the light chain regions were digested with ClaI and HindIII, and sequences encoding the heavy chain regions were digested with EcoRI and XhoI. The pCMV-cofragment plasmids were digested with HindIII and EcoRI, and the GS-vectors were digested with ClaI and XhoI. The four DNA fragments were purified, ligated, and transformed into bacteria. Single bacterial colonies were picked up and sequenced, and expression vectors containing the correct sequences to encode the half-antibody fragments were obtained and designated as GS-MIL220, GS-MIL221-1 and GS-MIL221-2. HEK-293F cells (Cobioer, China) were transfected with the expression vectors obtained above using PEI, following the protocol of Example 12. The transfected HEK-293F cells were cultured in an incubator in 5% $CO_2$ at 37° C. with shaking at 120 RPM. After 10-12 days, cell culture supernatants were harvested, and subject to centrifugation at 3500 rpm for 5 minutes and then to filtration using 0.22 μm film filters to remove cell debris. The half-antibody fragments were then purified using a pre-equilibrated Protein-A affinity column (Cat #:17040501, GE, USA) and eluted with the elution buffer (20 mM citric acid, pH 3.0-3.5). After buffer exchange, fragments were kept in PBS buffer (pH 7.0) and the concentration was determined using a NanoDrop instrument.

Example 14 Preparation of Bispecific Antibodies Against CD3 and CD20

The purified half-antibody fragments were assembled in vitro. Briefly, MIL220 and MIL221-1 were mixed, and MIL220 and MIL221-2 were also mixed, respectively at a 1:1 molar ratio. The mixtures were added with Tris base buffer till pH 8.0 followed by reducing agent glutathione (GSH), and allowed to react overnight at 25° C. with low-speed stirring. Then, the mixtures were added with 2 M acetic acid solution to adjust pH to 5.5. The reducing agent was removed by ultrafiltration, to terminate the reaction. The antibodies as assembled were purified using anions exchange chromatography and cation exchange chromatography. Anion exchange columns were balanced with low-salt Tris buffer (pH8.0), and loaded with the antibody samples. The components that had passed through the columns were collected, and rinsed by low-salt Tris buffer (pH8.0) until UV280 trended to the baseline. The collected samples were adjusted to pH5.5 using an acetic acid solution, concentrated to 1 ml using a 30 kDa ultrafilter tube, and filtered using 0.2 μm membrane. Cation exchange columns were balanced with a low-concentration acetate buffer (pH5.5), and loaded with the antibody samples. The low-concentration acetate buffer (pH5.5) was used to balance the columns again, and elution was done using 20 CV acetate solutions (concentration at 0-100%, pH5.5).

The bispecific antibody consisting of MIL220 and MIL221-1 was designated as MBS303-1, and the bispecific antibody composed of MIL220 and MIL221-2 was referred to as MBS303-2. The purified antibodies, with a purity higher than 90% as measured by mass spectrum, were further characterized below.

Example 15 Bispecific Antibodies Bound Human CD3, Monkey CD3 and CD20

The purified bispecific antibodies were tested for their binding capabilities to recombinant human and monkey CD3ε proteins by ELISA, following the protocol in Example 3. REGN1979 against CD3 and CD20 (prepared using the amino acids disclosed in US 2014/0088295A1, or alternatively INN 11035_H, INN 11035_L and INN 11035_M published on imgt.org), and CD20-TCB (prepared using the amino acids disclosed in WO2018220099A1, or alternatively INN 11145_H, INN 11145_L, INN 11145_M and INN 11145_N published on imgt.org) were used as reference antibodies, and an anti-HEL antibody (Cat #: LT12031, LifeTein, USA) was used as an negative control. The results were shown in FIG. 15 (FIGS. 15, A and B).

The bispecific antibodies' binding capabilities to human and monkey CD20 proteins expressed on HEK293A cells were further tested by FACS using the HEK293 cells constructed in Example 11 stably expressing human or monkey CD20, following the protocol of Example 12. The results were shown in FIG. 16 (FIGS. 16, A and B).

The bispecific antibodies' binding capabilities to human and monkey CD3 were further tested using Jurkat cells and monkey PBMCs by FACS, following the protocol of Example 12, except that PBMCs were collected from a healthy monkey's blood sample by density gradient centrifugation. The results were shown in FIG. 16 (FIGS. 16, C and D).

Figure 15:
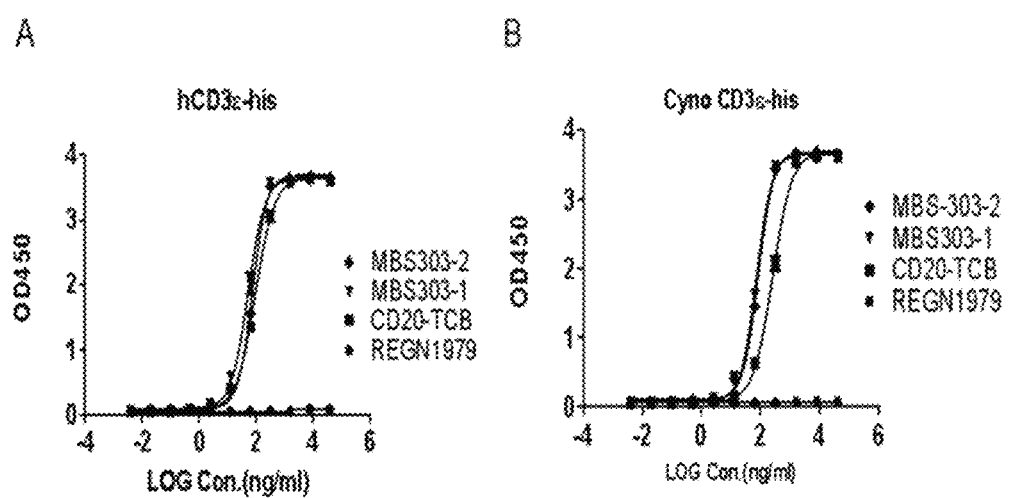
FIG. 15 shows the binding activity of the bispecific antibody to human CD3ε (A) and monkey CD3ε (B).

As shown in FIG. 15, MBS303-1, MBS303-2 and CD20-TCB specifically bound human and monkey CD3ε, but REGN1979 did not bind human or monkey CD3ε.

Figure 16:
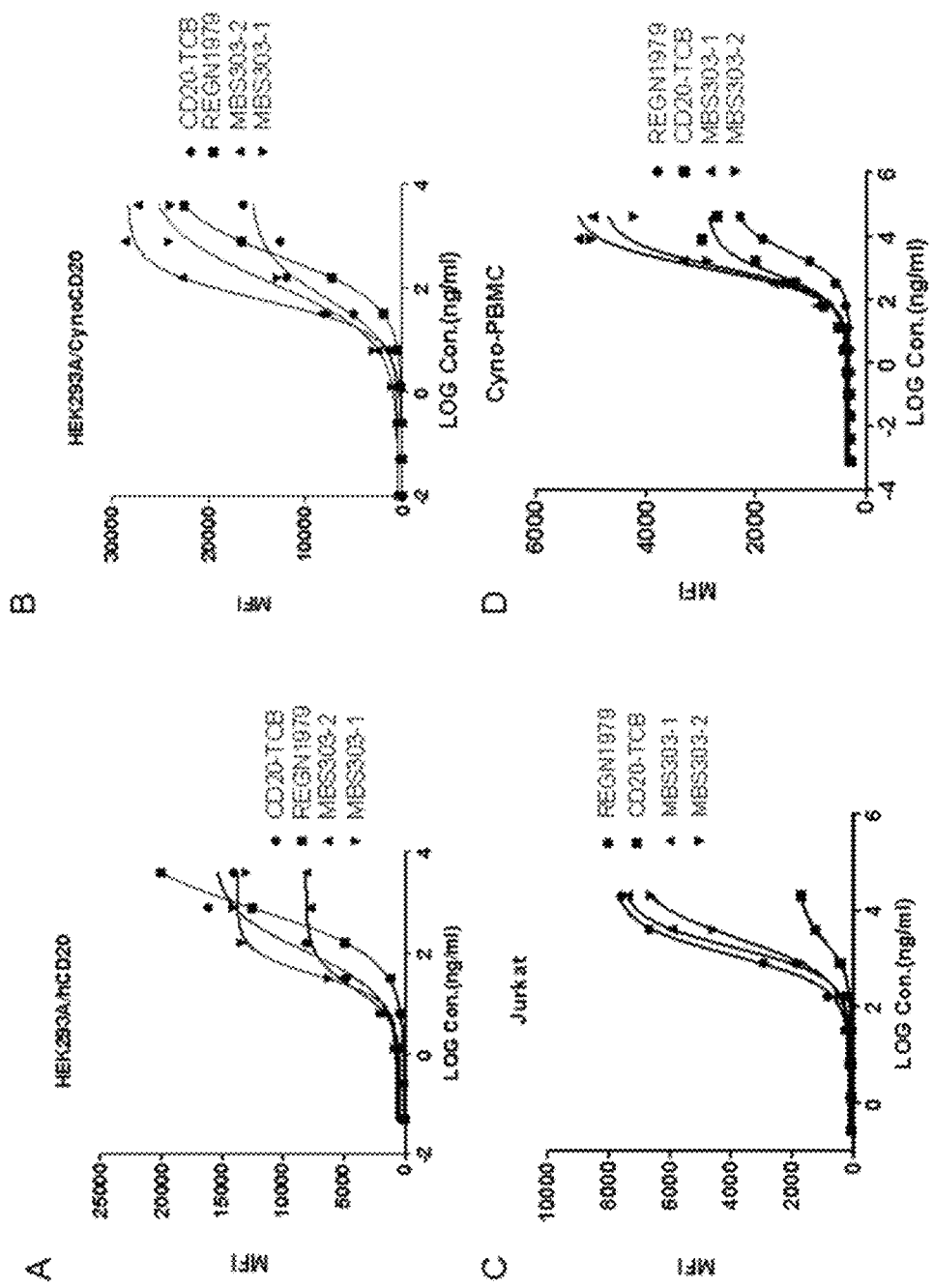
FIG. 16 shows the binding activity of the bispecific antibody to HEK293A/human CD20 (A), HEK293A/monkey CD20 (B), Jurkat cells (C) and monkey PBMCs (D).

According to FIGS. 16 (A and B), all the bispecific antibodies as tested bound to human and monkey CD20 expressed on cell surfaces, and the binding capabilities of MBS303-1, MBS303-2 and CD20-TCB to human CD20 were significantly higher than that of REGN1979. As shown in FIGS. 16 (C and D), all the bispecific antibodies bound human and monkey CD3 complexes on cell surfaces, and the binding capabilities of MBS303-1, MBS303-2 and REGN1979 to human CD3 complexes were significantly higher than that of CD20-TCB.

Example 16 Binding Affinity Determination of Bispecific Antibodies by SPR

The binding affinities of the bispecific antibodies of the disclosure to human and monkey CD3ε were tested using BIAcore™ 8K (GE Life Sciences, USA), following the protocol of Example 6.

The binding affinities measured by BIAcore™ were summarized in Table 7. REGN1979's binding affinities to human or monkey CD3ε were not detectable, and other bispecific antibodies' binding affinities were in the order of nM. Consistent with the FACS test results, MBS303-1 and MBS303-2 showed higher binding affinities to human and monkey CD3ε subunits than CD20-TCB.

Example 17 Bispecific Antibodies' Effects on T Cell Activation

The free bispecific antibodies' effects on activating CD3/TCR signaling were tested using primary human PBMCs, following the protocol of Example 12 with the following modifications. In specific, cell culture supernatants were collected after 48 h incubation and measured for both IFN-γ and TNF-α levels by ELISA kits (Cat #: 430107, Biolegend, USA; Cat #: 430207, Biolegend, USA), according to the manufacturer's instructions.

Figure 17:
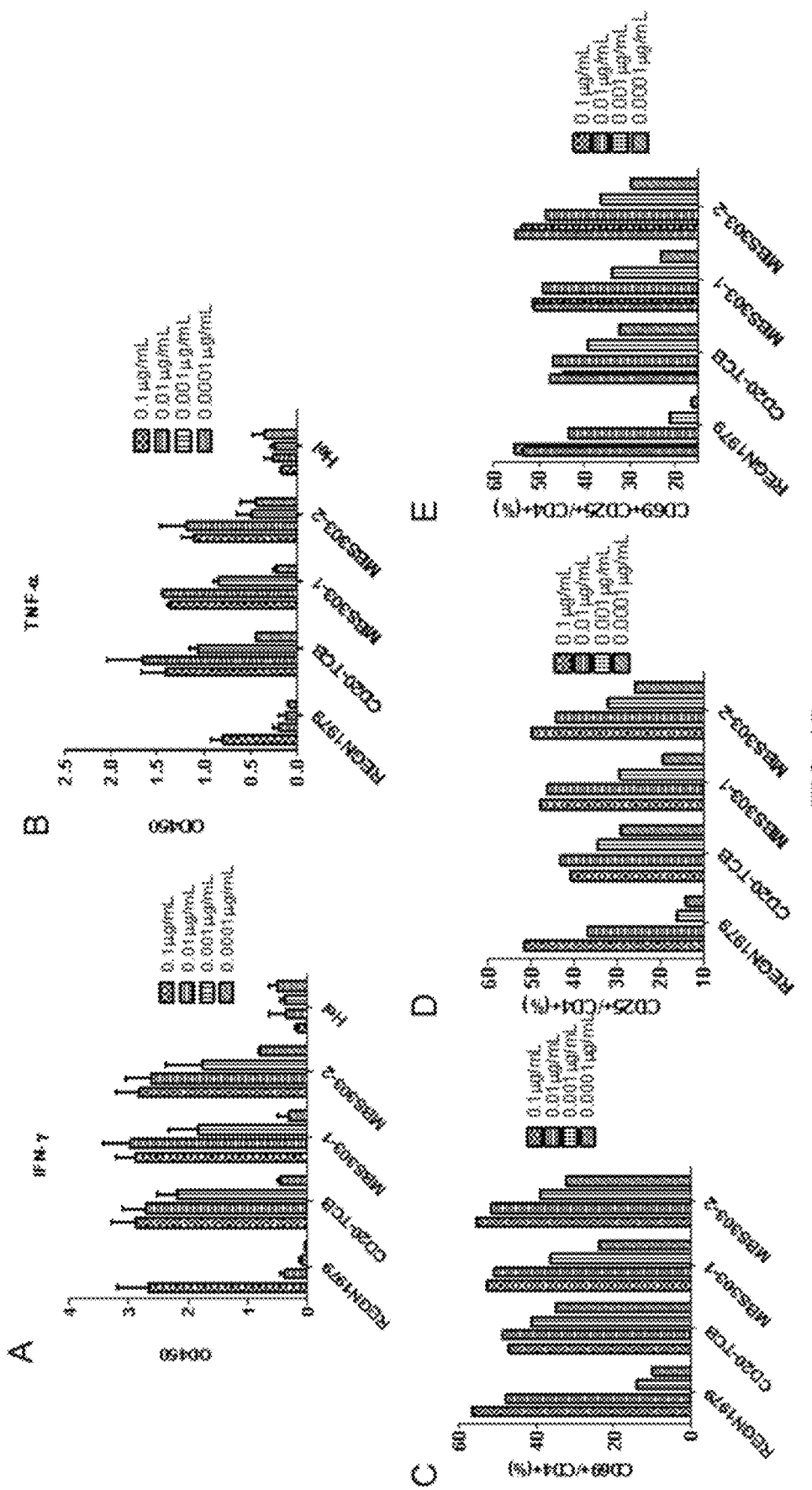
FIG. 17 shows the capability of the bispecific antibody, when unbound to secondary antibodies, to induce IFN-γ release (A), tumor necrosis factor-α (TNF-α) release (B), CD69 expression (C), CD25 expression (D), and CD69+CD25 co-expression (E) by human PBMCs.

The results were shown in FIGS. 17 (A and B). The IFN-γ and TNF-α levels induced by REGN1979 were significantly lower than those induced by CD20-TCB, MBS303-1 or MBS303-2, and CD20-TCB induced highest cytokine release. FIGS. 17 (C, D and E) showed the expression levels of T cell activation markers, which were consistent with cytokine level test results. In specific, REGN1979 induced T cell activation at a significantly lower activity than CD20-TCB, MBS303-1 and MBS303-2, and CD20-TCB's activity was highest in inducing T cell activation.

Example 18 Bispecific Antibodies Induced T Cell Activation and Killing of CD20$^+$ Tumor Cells by PBMCs The bispecific antibodies were further tested for their capabilities of inducing killing of CD20$^+$ Raji cells by PBMCs. The Raji cells were labeled with carboxyfluorescein succinimidyl ester with green fluorescence. Specifically, Raji cells were re-suspended in RPMI complete media at cell density of $1.0 \times 10^6$/ml and labeled with carboxyfluorescein succinimidyl ester (CFSE, Cat #: C34554I, Invitrogen, USA) according to the manufacturer's instructions, except that the cells were incubated with 2.5 μM CFSE at 37° C. for 10 min. The labeled cells were re-suspended in RPMI complete media (RPMI+10% FBS) at a viable cell density of $2.5 \times 10^5$/ml. PBMCs from a healthy human donor's blood sample were collected by density gradient centrifugation, and re-suspended in RPMI complete media (RPMI1640+10% FBS) at a viable cell density of $5 \times 10^5$/ml. The Raji cells (100 μl) and the PBMCs (100 μl) were seeded on a 96-well plate, with an effector-target ratio at 2:1, and then added with 100 μl bispecific antibodies at different concentrations. The cell/antibody mixtures were incubated in an incubator at 37° C. and 5% $CO_2$ for 48 h.

Fifty μl cell culture supernatants were collected from each well and measured for IFN-γ, IL-2, and TNF-α levels using 3 kits (Cat #: 430107, Biolegend, USA; Cat #: S2050, R&D, USA; Cat #: 430207, Biolegend, USA). The results were shown in FIG. 19.

The viability of Raji cells was measured by LIVE/DEAD™ Fixable Violet Dead Cell Stain Kit (Cat #: L34964,

TABLE 7

Binding affinities of bispecific antibodies to human/monkey CD3ε

| Antibody | Human CD3ε | | | Monkey CD3ε | | |
| --- | --- | --- | --- | --- | --- | --- |
| | Ka | Kd | KD | Ka | Kd | KD |
| REGN1979 | / | / | / | / | / | / |
| CD20-TCB | 5.43E+5 | 3.04E−3 | 5.60E−9 | 5.50E+05 | 2.21E−03 | 4.01E−09 |
| MBS303-1 | 2.23E+5 | 4.43E−4 | 1.99E−9 | 3.47E+05 | 5.37E−04 | 1.55E−09 |
| MBS303-2 | 2.07E+5 | 3.7E−4 | 1.79E−9 | 2.79E+05 | 5.04E−04 | 1.81E−09 |

Thermo Fisher, USA). The cell/antibody mixtures above were rinsed by PBS for three times, and incubated with the stains at 37° C. for 30 min. The cells were rinsed by PBS for another three times, and subject to FACS measurement. The death rates of cells with green fluorescence (Raji cells) were determined, and the results were shown in FIG. 18.

Figure 18:
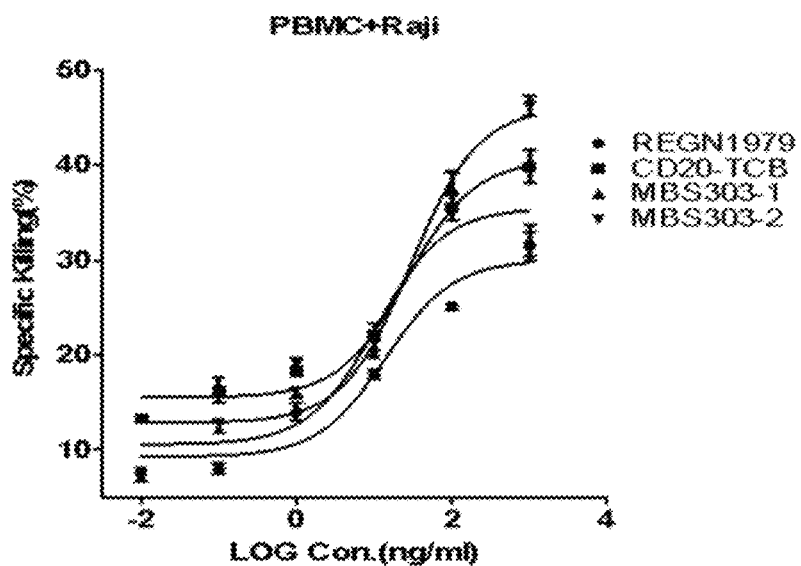
FIG. 18 shows bispecific antibody mediated killing of CD20+ Raji cells by human PBMCs.

According to FIG. 18, all the bispecific antibodies were able to induce T cell mediated Raji cell death. Among the antibodies, REGN1979 had the weakest activity in inducing Raji cell death, and MBS303-1 and MBS303-2's activities were higher than that of REGN1979 and comparable to or a bit weaker than that of CD20-TCB.

Figure 19:
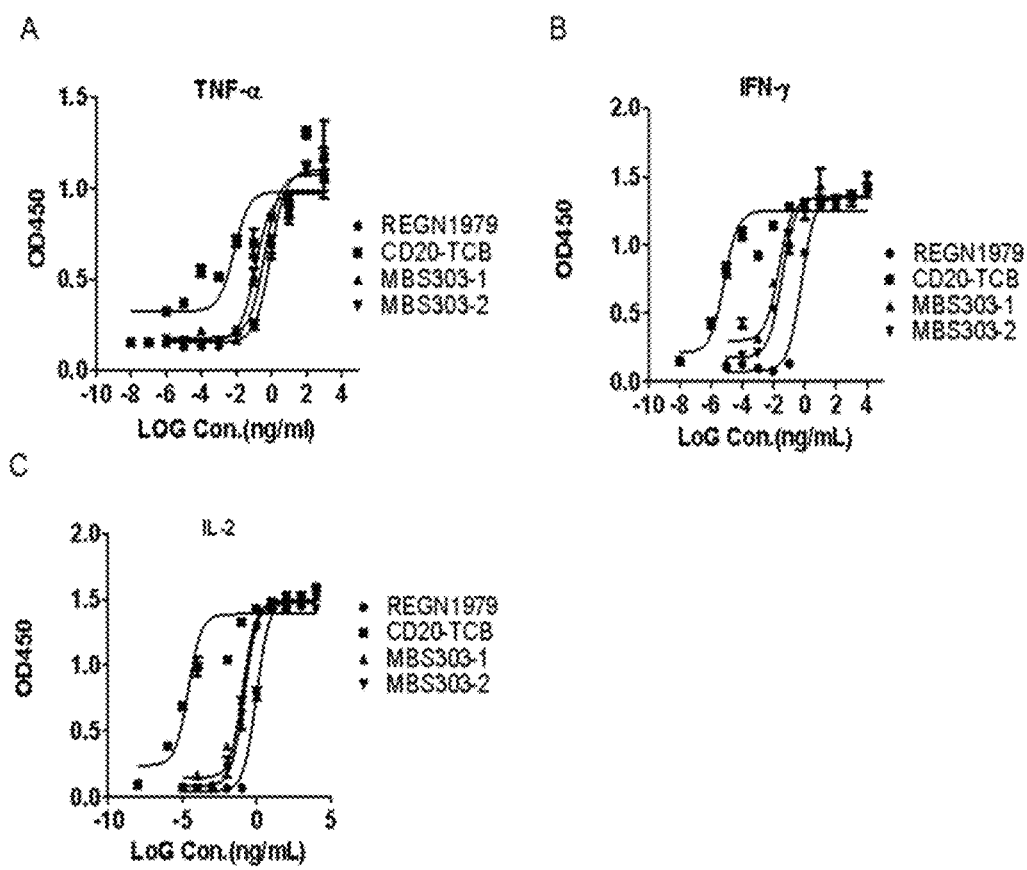
FIG. 19 shows the capability of the bispecific antibody to induce TNF-α release (A), IFN-γ release (B), and interleukin-2 (IL-2) release (C) by PMBCs when incubated with CD20$^+$ Raji cells.

As shown in FIG. 19, all the bispecific antibodies induced IFN-γ, IL-2 and TNF-α release by T cells. Among the antibodies, CD20-TCB induced most cytokine release, while the cytokine levels induced by MBS303-1 and MBS303-2 were much lower than that induced by CD20-TCB and comparable or a bit higher than that induced by REGN1979.

Example 19 Bispecific Antibodies Specifically Induced $CD3^+$ T Cell Activation and Killing of $CD20^+$ Tumor Cells by $CD3^+$ T Cells The bispecific antibodies were further tested for their capabilities of inducing targeted killing of $CD20^+$ tumor cells by T cells. The HEK293A/hCD20 cells constructed in Example 11 were used as the $CD20^+$ tumor cells, and the parent HEK293A cells were used as $CD20^-$ tumor cells. The HEK293A/hCD20 cells were prepared by using pLV-EGFP (2A)-Puro plasmids and thus over-expressed GFP with green fluorescence, while HEK293A cells were labeled with CFSE with green fluorescence following the protocol of Example 18.

Briefly, PBMCs from a healthy human donor's blood sample were collected by density gradient centrifugation, and $CD4^+$ T cells were isolated from the PBMCs using Invitrogen Dynabeads Untouched Human CD4+ T cell isolation kit (Cat #: 11346D, Thermal Fisher Scientific, USA), following the manufacturer's instruction. The target cells (HEK293A/hCD20 cells/HEK293A cells) and the effector cells (T cells) were subject to centrifugation at 1200 rpm for 5 min, and then re-suspended in RIPM1640 complete media (RIPM1640+10% FBS) with viable cells accounting for about 95%. The target cells and T cells were adjusted to cell densities of $2.5 \times 10^5$/ml and $5 \times 10^5$/ml, respectively, and 100 μl target cells and 100 μl T cells with effector-target ratio at 2:1 were added to each well of a 96 well plate. Then, 50 μl diluted antibodies (1:10 dilution, starting at 10 μg/ml) were added to each well. The cell/antibody mixtures were incubated in an incubator at 37° C. and 5% $CO_2$ for 48 h. An anti-CD20 monospecific antibody MIL62, which was afucosylated with enhanced ADCC activity (prepared using the amino acid sequences and preparation method disclosed in CN108138186B), REGN1979 and CD20-TCB were used as positive controls.

After 48 h incubation, 50 μl cell culture supernatants were collected from each well and measured for IFN-γ and TNF-α levels using 2 kits (Cat #: SIF50, R&D, USA; Cat #: 430207, Biolegend, USA). The results were shown in FIG. 21.

The viability of tumor cells was measured by LIVE/DEAD™ Fixable Violet Dead Cell Stain Kit (Cat #: L34964, Thermo Fisher, USA). In specific, the cell/antibody mixtures above were rinsed by PBS for three times, and incubated with the stains at 37° C. for 30 min. The cells were rinsed by PBS for another three times, and subject to FACS test. The death rates of cells with green fluorescence (HEK293/hCD20 cells or HEK293 cells) were determined, and the results were shown in FIG. 20.

Figure 20:
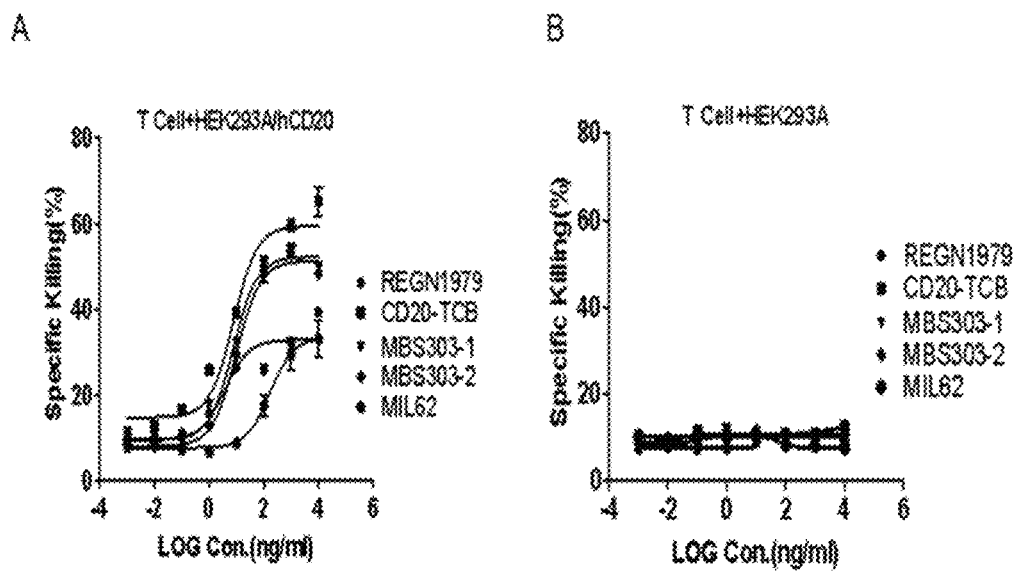
FIG. 20 shows the bispecific antibody mediated killing of HEK293A/human CD20 cells (A) and CD20$^-$ HEK293A cells (B) by human T cells.

According to FIG. 20, all the bispecific antibodies were able to induce targeted killing of $CD20^+$ tumor cells by T cells, but had not such effects on $CD20^-$ cells. And the bispecific antibodies killed significantly more $CD20^+$ tumor cells than the monospecific anti-CD20 antibody MIL62. Among the bispecific antibodies, REGN1979 had the weakest activity in inducing targeted killing, and MBS303-1 and MBS303-2's activities were higher than that of REGN1979 and comparable to or a bit weaker than that of CD20-TCB.

Figure 21:
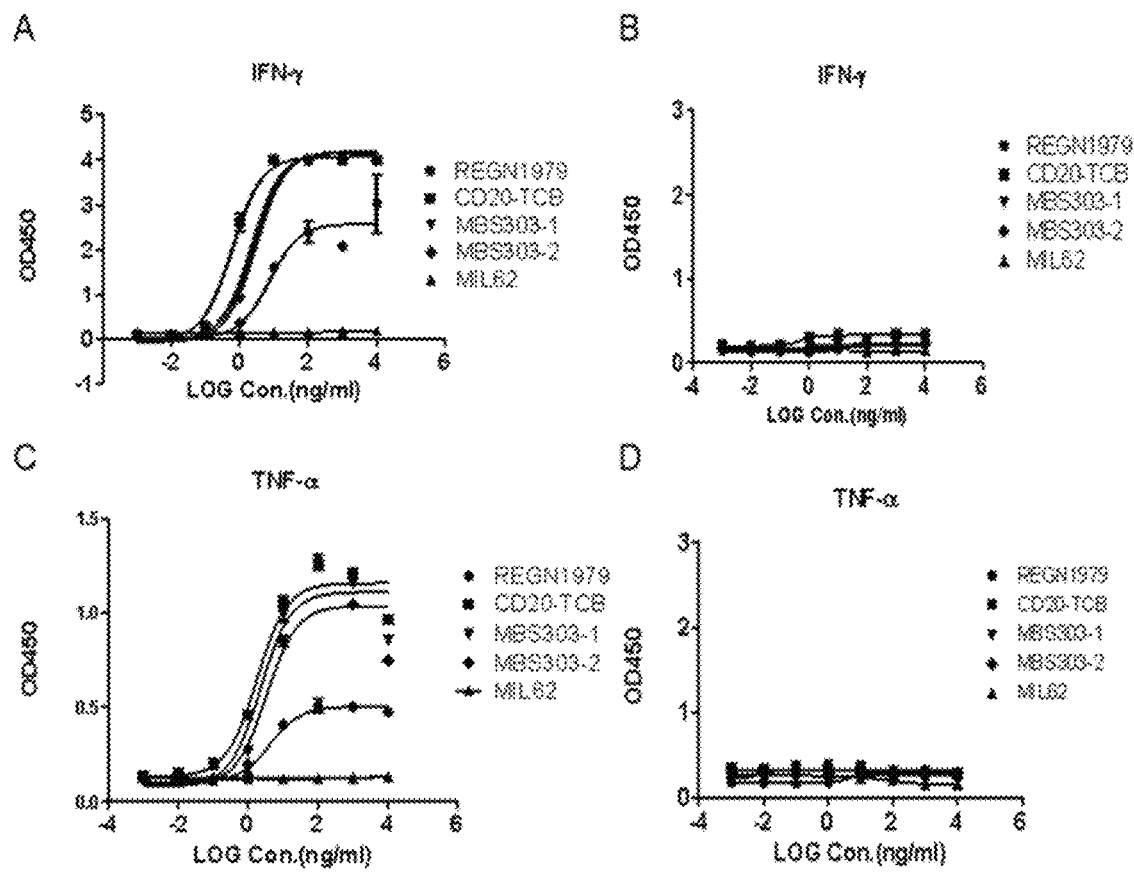
FIG. 21 shows the capability of the bispecific antibody to induce IFN-γ release (A) and TNF-α release (C) by T cells when incubated with HEK293A/human CD20 cells, and to induce IFN-γ release (B) and TNF-α release (D) by T cells when incubated with CD20$^-$ HEK293A cells.

As shown in FIG. 21, IFN-γ and TNF-α release by T cells as induced by the bispecific antibodies were mediated by $CD20^+$ cell, and the specific antibodies were not able to induce cytokine release by T cells with $CD20^-$ cells. Among the bispecific antibodies, CD20-TCB induced most cytokine release, while the cytokine levels induced by MBS303-1 and MBS303-2 were much lower than that induced by CD20-TCB.

Example 20 MIL62 Pretreatment Decreased Bispecific Antibody Induced Cytokine Release by PBMCs The effects of the bispecific antibodies of the disclosure when used in combination with MIL62 on cytokine release by PBMCs were tested. Briefly, PBMCs from a healthy human donor's blood sample were collected by density gradient centrifugation, re-suspended in RPMI complete media (RPMI 1640+10% FBS), and divided into two aliquots. One aliquot was added with MIL62 at the final concentration of 1 μg/ml and incubated in an incubator at 37° C. and 5% $CO_2$ for 48 h, the other was directly incubated in an incubator at 37° C. and 5% $CO_2$ for 48 h. The PBMCs were rinsed by PBS for three times, and re-suspended in RPMI complete media (RPMI 1640+10% FBS) at a cell density of $5 \times 10^5$/ml. To each well was added 200 μl of the PBMC suspensions. For PMBCs pretreated with MIL62, each well was added with MIL62 at a final concentration of 1 μg/ml and MBS303-2 or MBS303-1 at different concentrations. For PBMCs without pretreatment with MIL62, each well was added with MBS303-2 at different concentrations. The PBMC/antibody mixtures were incubated in an incubator at 37° C. and 5% $CO_2$ for 48 h, and 50 μl cell culture supernatants were collected for measurement of IFN-γ and TNF-α levels, using 2 ELISA kits (Cat #: SIF50, R&D, USA; Cat #: 430207, Biolegend, USA), according to the manufacturers' instructions. The cells were collected, rinsed by PBS for three times, added with 2 μl PE Mouse anti-Human CD69 antibody (Cat #: 555531, BD, USA), 2 μl BV605 Mouse Anti-Human CD25 antibody (Cat #: 562660, BD, USA), and 2 μl FITC Mouse anti-Human CD4 antibody (Cat #: 561842, BD, USA), and incubated at room temperature for 30 min. The cells were collected with centrifugation, rinsed by PBS for three times, and measured by FACS for the ratio of $CD69^+CD4^+$ T cells, $CD25^+CD4^+$ T cells, or the $CD69^+CD25^+CD4+$ T cells to $CD4^+$ T cells.

Figure 22:
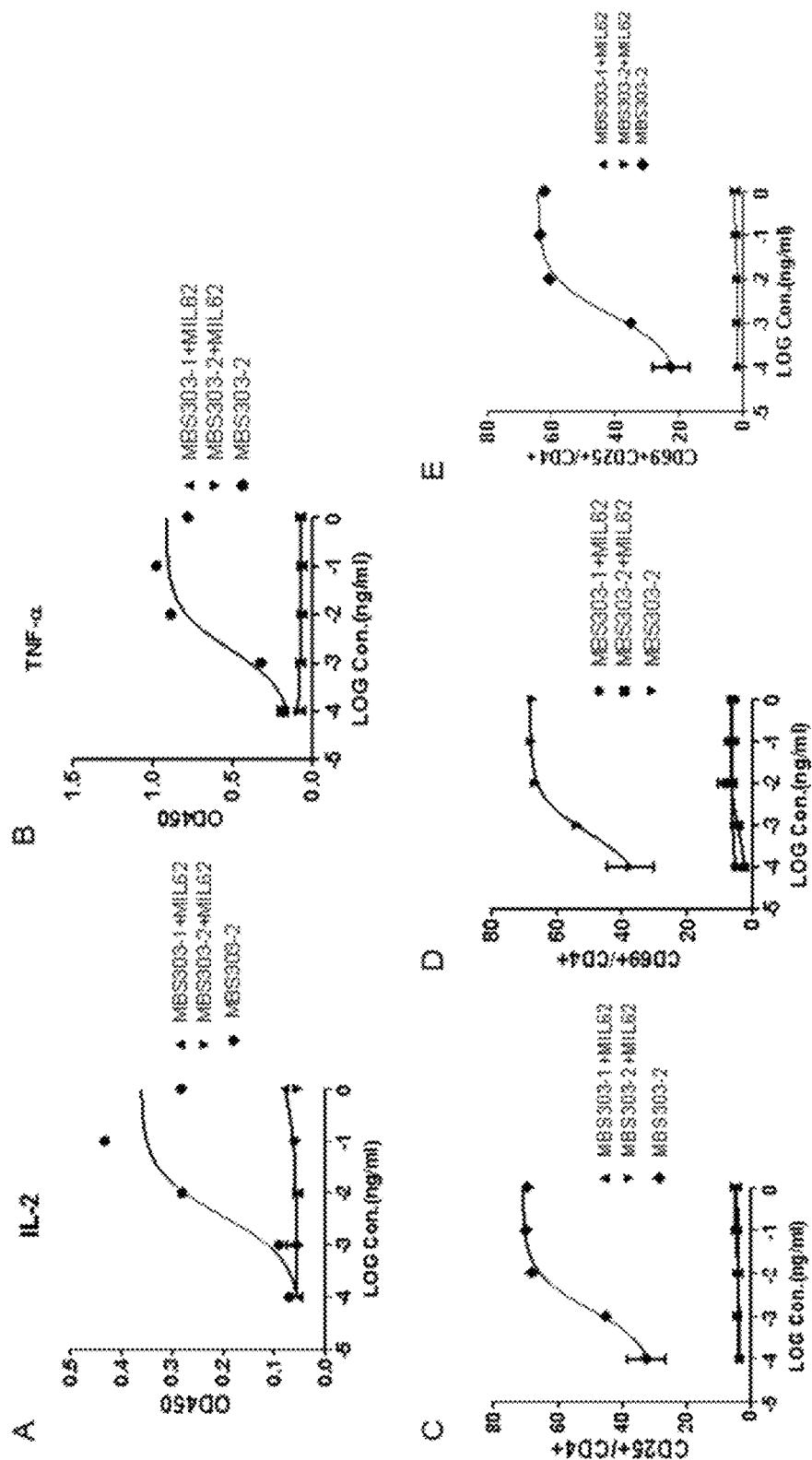
FIG. 22 shows the effect of the bispecific antibody, when administered with or without 1 μg/ml MIL62, on IL-2 release (A), TNF-α release (B), CD25 expression (C), CD69 expression (D), and CD69+CD25 co-expression (E) by human PBMCs pretreated with 1 μg/ml MIL62 or not.

As shown in FIG. 22, when treated with the bispecific antibodies alone, PBMCs released relatively high levels of cytokines such as IFN-γ and TNF-α and expressed relatively high levels of T cell activation markers such as CD69 and CD25. However, when PBMCs were pretreated with MIL62 followed by the combined use of MIL62 and a bispecific antibody of the disclosure, almost no cytokine release or T cell activation marker expression was observed.

Example 21 Anti-Tumor Effects of Exemplary Bispecific Antibodies in Combination with MIL62

The anti-tumor effects of MIL62 in combination with the bispecific antibodies of the disclosure were tested by killing of CD20$^+$ cells (i.e., HEK293A/hCD20 cells) by T cells. Briefly, PBMCs from a healthy human donor's blood sample were collected by density gradient centrifugation, and CD4$^+$ T cells were isolated from the PBMCs using Invitrogen Dynabeads Untouched Human CD4$^+$ T cell isolation kit (Cat #: 11346D, Thermal Fisher Scientific, USA), following the manufacturer's instruction. HEK293A/hCD20 cells were prepared by using pLV-EGFP(2A)-Puro plasmids and thus over-expressed GFP with green fluorescence. The target cells and the effector cells (i.e., T cells) were subject to centrifugation at 1200 rpm for 5 min, and then re-suspended in RIPM1640 complete media (RIPM1640+10% FBS) with about 95% viable cells. The target cells and T cells were adjusted to cell densities of $2.5 \times 10^5$/ml and $5 \times 10^5$/ml, respectively, and 100 μl target cells and 100 μl T cells with effector-target ratio at 2:1 were added to each well of a 96 well plate. The resultant mixed suspensions were divided into two aliquotes, one added with 50 μl diluted bispecific antibodies (10-fold dilution, starting at 10 μg/ml), the other added with MIL62 at the final concentration of 1 μg/ml and 50 μl diluted bispecific antibodies (10-fold dilution, starting at 10 μg/ml). The cell/antibody mixtures were incubated in an incubator at 37° C. and 5% $CO_2$ for 48 h. The viability of HEK293A/hCD20 cells was measured by LIVE/DEAD™ Fixable Violet Dead Cell Stain Kit (Cat #: L34964, Thermo Fisher, USA). Specifically, the cell/antibody mixtures above were rinsed by PBS for three times, and incubated with the stains at 37° C. for 30 min. The cells were rinsed by PBS for three times, and subject to FACS measurement. The death rates of cells with green fluorescence (HEK293A/hCD20 cells) were determined.

Figures 23, 24:
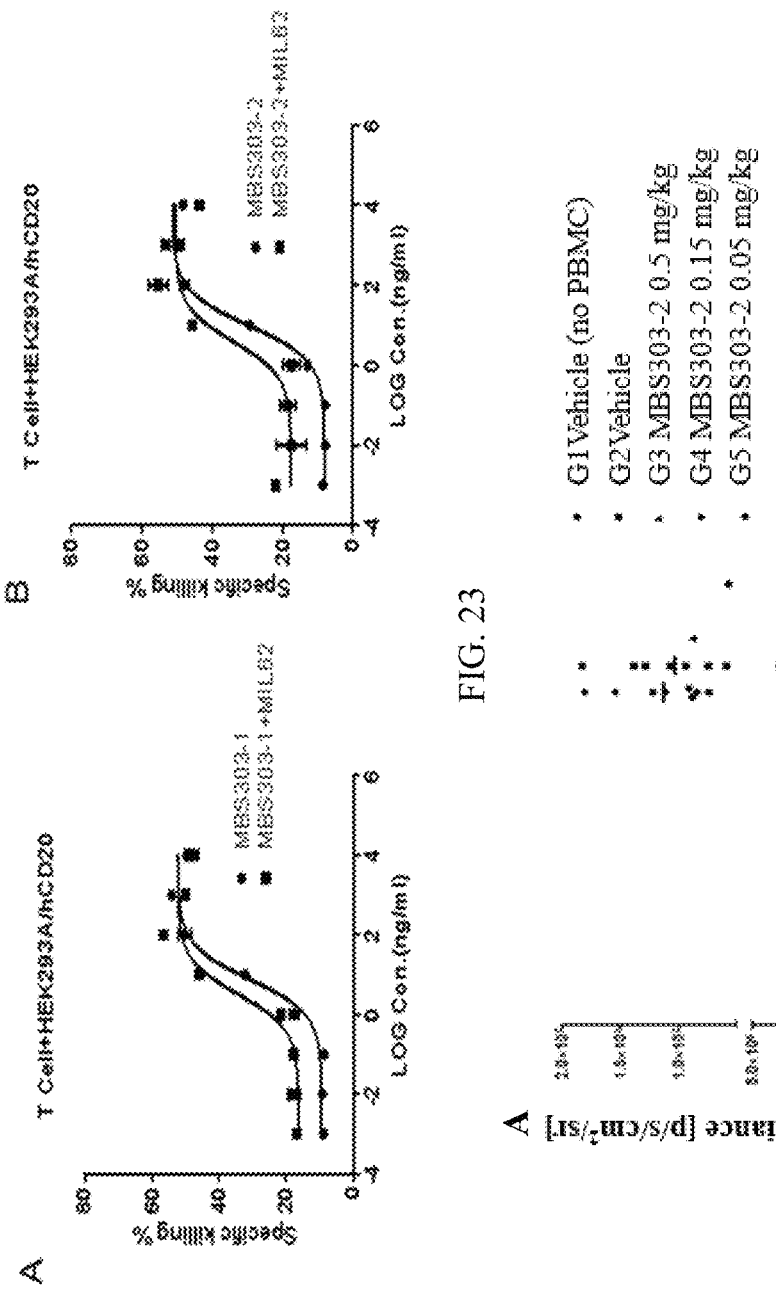
FIG. 23 shows the killing of HEK293A/human CD20 cells by T cells mediated by MBS303-1 (A) and MBS303-2 (B) co-administered with 1 μg/ml MIL62 or not.
FIG. 24 shows the in vivo anti-tumor effect of the bispecific antibody on tumor-bearing mice with humanized PBMCs. (A) Average fluorescence intensities of tumor cells 3, 10 and 17 days post MBS303-2 or vehicle administration; (B) Tumor imaging on Day 10 and Day 17 post drug administration; and (C) Survival curves of tumor-bearing mice.
Figure 24:
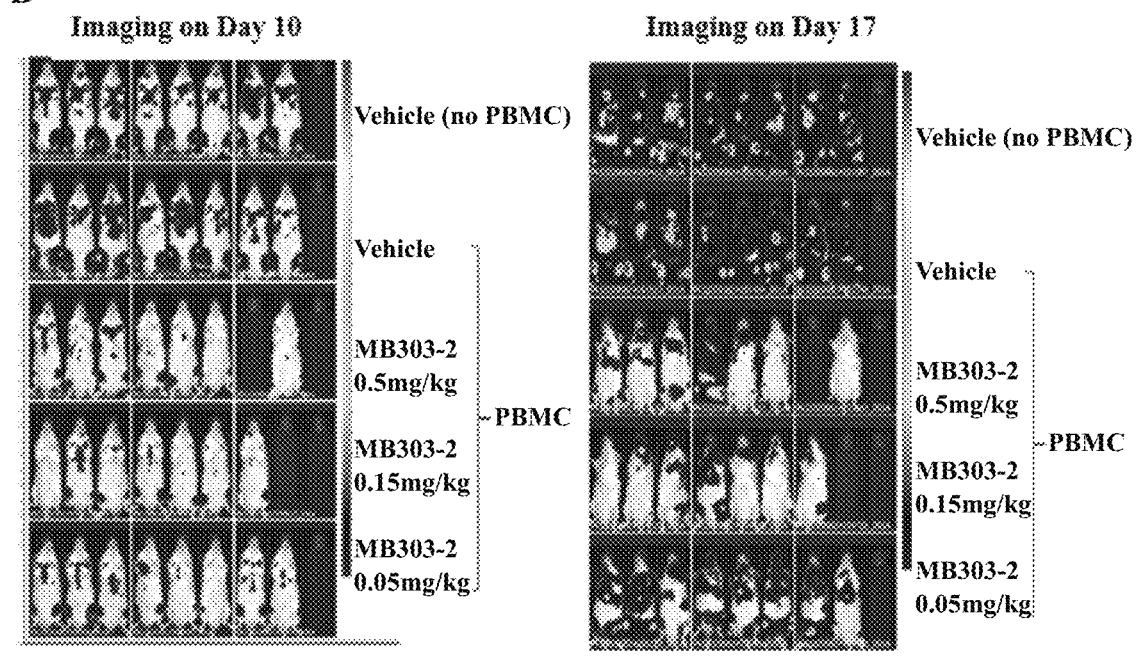
Figure 24:
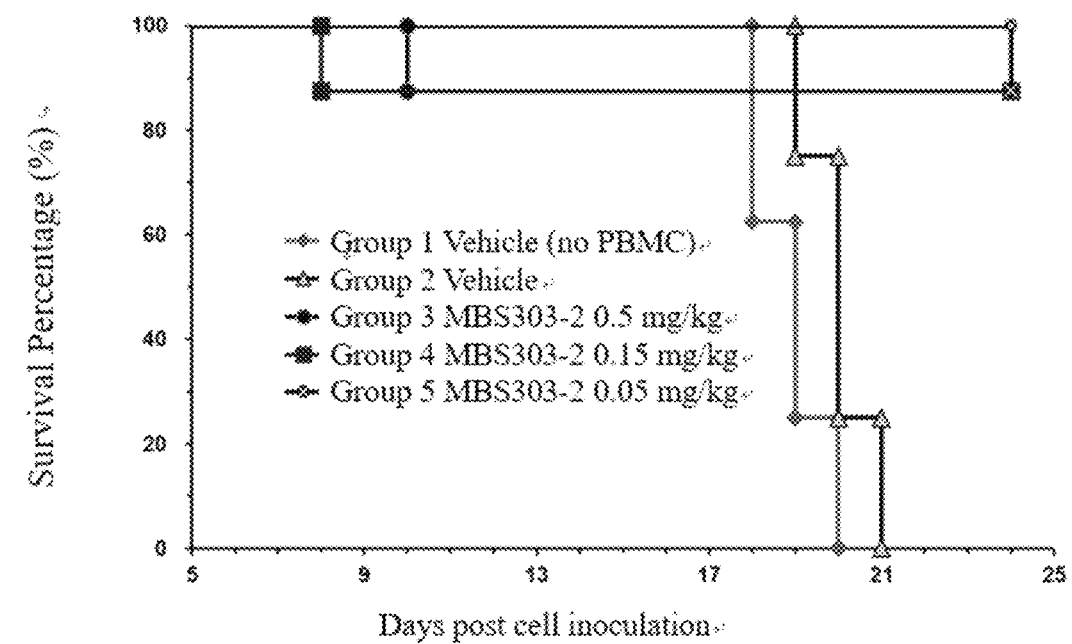

The results were shown in FIG. 23, MIL62 and the bispecific antibodies provided synergic anti-tumor effects. The $EC_{50}$ was 7.6 ng/ml for MBS303-1 treatment alone, and decreased to 3.2 ng/ml when MBS303-1 was used in combination with MIL62. MBS303-2 had $EC_{50}$ at 9.8 ng/ml when used alone, and had $EC_{50}$ at 3.9 ng/ml when used with MIL62.

Example 22 In Vivo Anti-Tumor Effects of Bispecific Antibodies

MBS303-2's anti-tumor effect in vivo was investigated using an animal model built by grafting Raji cells expressing luciferase (designated as Raji-luc cells, Yicon (Beijing) Medical Science And Technology Co., Ltd.) into PBMC humanized immunodeficiency mice (GemPharmatech Co. Ltd, China). Part of the mice were injected with 100 μl PBMCs collected from a healthy human donor at a cell density of $5 \times 10^7$/ml, by tail vein injection. Three days later, Raji-luc cells were re-suspended in PBS with a density of $5 \times 10^6$/ml, and 100 μl of the Raji-luc cell suspension was injected by tail vein into animals having or having not received PBMCs, this day designated as Day 0. The animals were randomly allocated into 5 groups, 8 per group, and administered with PBS or MBS303-2 at Day 3, Day 10 and Day 17 at 0.05 mg/kg, 0.15 mg/kg and 0.5 mg/kg, respectively.

Tumor sizes, mice' conditions and mouse weights were monitored over time. The mice were observed every day for health status, and their survival times starting from Raji-luc injection to death or euthanasia were recorded. Euthanasia would be done when 1) a mouse's body weight decreased by more than 20%, 2) a mouse can no longer actively drink water, 3) a mouse's tumor load reached $5 \times 10^7$ according to average radiation (p/sec/cm$^2$/sr), and/or 4) something unusual happened that adversely affected animal welfare and/or the experiment, as determined by veterinarians. The tumor-bearing mice' median survival time (MST) in each group and the increase in life span (ILS %) in the treatment groups were determined. ILS % was calculated as (median survival days in treatment group/median survival days in control group-1)×100%. A treatment was deemed as effective when statistic significance was found relative to the control group. The mice, after allocated to different groups, were, once a week, intraperitoneally injected with the substrates for luciferase, 15 mg/ml, 10 μl/g body weight, and subject to anesthesia with isoflurane followed by fluorescent signal collection using a small animal imaging instrument (IVIS Lumina Series III, PerkinElmer) for characterizing tumor growth in mice. One-way ANOVA was used to analyze signal differences among groups, and Kaplan-Meier and Log Rank were to analyze the group differences in survival times of tumor-bearing mice. Statistic significance was found when $P<0.05$.

As shown in FIGS. 24 (A and B), either the imaging or fluorescent intensity analysis showed that MBS303-2 significantly inhibited tumor growth in a dose-dependent manner. According to FIG. 24 (C), MBS303-2 significantly prolonged the survival of tumor-bearing mice, suggesting its evident anti-tumor activity in vivo.

Sequences in the present application are summarized below.

```
Description/Sequence/SEQ ID NO.
```

VH-CDR1 of mouse and chimeric CD3-19 antibodies, mouse, chimeric and humanized 19-15 and 19-26 antibodies, mouse and chimeric 19-37 antibodies
X1YAMN (SEQ ID NO: 1)

VH-CDR1 of mouse and chimeric CD3-19 antibodies
SYAMN (SEQ ID NO: 1, X1 = S)

VH-CDR1 of mouse, chimeric and humanized 19-15 and 19-26 antibodies, mouse and chimeric 19-37 antibodies
TYAMN (SEQ ID NO: 1, X1 = T)

VH-CDR2 of mouse and chimeric CD3-19 antibodies, mouse, chimeric and humanized 19-26 antibodies, mouse, chimeric and humanized 19-15 antibodies, mouse and chimeric 19-37 antibodies
RIRSKYNNYATYYAX1SV (SEQ ID NO: 2)

| Description/Sequence/SEQ ID NO. |
| --- |

VH-CDR2 of mouse and chimeric CD3-19 antibodies, mouse, chimeric and humanized 19-26 antibodies
RIRSKYNNYATYYA<u>D</u>SV (SEQ ID NO:2, X1 = D)

VH-CDR2 of mouse, chimeric and humanized 19-15 antibodies, mouse and chimeric 19-37 antibodies
RIRSKYNNYATYYA<u>I</u>SV (SEQ ID NO:2, X1 = I)

VH-CDR3 of mouse and chimeric CD3-19 antibodies, mouse, chimeric and humanized 19-15 antibodies, mouse and chimeric 19-37 antibodies, mouse, chimeric and humanized 19-26 antibodies
HGNFGNSYX1SX2WAY (SEQ ID NO: 3)

VH-CDR3 of mouse and chimeric CD3-19 antibodies, mouse, chimeric and humanized 19-15 antibodies
HGNFGNSY<u>LS</u>YWAY (SEQ ID NO: 3, X1 = L, X2 = Y)

VH-CDR3 of mouse and chimeric 19-37 antibodies
HGNFGNSY<u>I</u>S<u>Y</u>WAY (SEQ ID NO: 3, X1 = I, X2 = Y)

VH-CDR3 of mouse, chimeric and humanized 19-26 antibodies
HGNFGNSY<u>I</u>S<u>W</u>WAY (SEQ ID NO: 3, X1 = I, X2 = W)

VL-CDR1 of mouse and chimeric CD3-19 antibodies, mouse, chimeric and humanized 19-15 antibodies, mouse, chimeric and humanized 19-26 antibodies, mouse and chimeric 19-37 antibodies
X1SSTGAVTTX2NYAN (SEQ ID NO: 4)

VL-CDR1 of mouse and chimeric CD3-19 antibodies
<u>D</u>SSTGAVTT<u>S</u>NYAN (SEQ ID NO: 4, X1 = D, X2 = S)

VL-CDR1 of mouse, chimeric and humanized 19-15 antibodies
<u>Q</u>SSTGAVTT<u>N</u>NYAN (SEQ ID NO: 4, X1 = Q, X2 = N)

VL-CDR1 of mouse, chimeric and humanized 19-26 antibodies
<u>K</u>SSTGAVTT<u>S</u>NYAN (SEQ ID NO: 4, X1 = K, X2 = S)

VL-CDR1 of mouse and chimeric 19-37 antibodies
<u>R</u>SSTGAVTT<u>N</u>NYAN (SEQ ID NO: 4, X1 = R, X2 = N)

VL-CDR2 of mouse and chimeric CD3-19 antibodies, mouse, chimeric and humanized 19-15 antibodies, mouse, chimeric and humanized 19-26 antibodies, mouse and chimeric 19-37 antibodies
GTX1X2X3AP (SEQ ID NO: 5)

VL-CDR2 of mouse and chimeric CD3-19 antibodies
GT<u>QRS</u>AP (SEQ ID NO: 5, X1 = Q, X2 = R, X3 = S)

VL-CDR2 of mouse, chimeric and humanized 19-15 antibodies
GT<u>KQR</u>AP (SEQ ID NO: 5, X1 = K, X2 = Q, X3 = R)

VL-CDR2 of mouse, chimeric and humanized 19-26 antibodies
GT<u>NLH</u>AP (SEQ ID NO: 5, X1 = N, X2 = L, X3 = H)

VL-CDR2 of mouse and chimeric 19-37 antibodies
GT<u>RLS</u>AP (SEQ ID NO: 5, X1 = R, X2 = L, X3 = S)

VL-CDR3 of mouse and chimeric CD3-19 antibodies, mouse, chimeric and humanized 19-15 antibodies, mouse and chimeric 19-37 antibodies, mouse, chimeric and humanized 19-26 antibodies
X1LWYSNLWV (SEQ ID NO: 6)

VL-CDR3 of mouse and chimeric CD3-19 antibodies, mouse, chimeric and humanized 19-15 antibodies, mouse and chimeric 19-37 antibodies
<u>V</u>LWYSNLWV (SEQ ID NO: 6, X1 = V)

VL-CDR3 of mouse, chimeric and humanized 19-26 antibodies
<u>A</u>LWYSNLWV (SEQ ID NO: 6, X1 = A)

VH of mouse and chimeric CD3-19 antibodies
EVKLLESGGGLVQPKGSLKLSCAASGFTFNSYAMNWVRQAPKGLEWVA**RIRSKYNNYAT
YYADSVKDRFTISRDDSQSILYLQMNNLKTEDTAMYYCVRHGNFGNSYLSYWAY**WGQTL
VTVSA (SEQ ID NO: 7)

VL of mouse and chimeric CD3-19 antibodies
QAVVTQESALTTSPGETVTLTCDSSTGAVTTSNYANWVQEKPDHLFTGLIGGTQRSAPGVP
ARFSGSLIGDKAALTITGAQTEDEAIYFCVLWYSNLWVFGGGTKLTVL (SEQ ID NO: 15)

| Description/Sequence/SEQ ID NO. |
|---|

VH of mouse and chimeric 19-15 antibodies
EVKLLESGGGLVQPKGSLKLSCAASGFTFNTYAMNWVRQAPGKGLEWVA**RIRSKYNNYAT
YYAISVKDRFTISRDDSQSILYLQMNNLKTEDTAMYYCVRHGNFGNSYLSYWAY**WGQGTL
VTVSA (SEQ ID NO: 8)

VH of humanized antibodies 15H2L2 and 15H2L3
EVQLLESGGGLVQPGGSLRLSCAASGFTFNTYAMNWVRQAPGKGLEWVA**RIRSKYNNYAT
YYAISVKDRFTISRDNSKNTLYLQMNSLRAEDTAVYYCVKHGNFGNSYLSYWAY**WGQGTL
VTVSS (SEQ ID NO: 9)

VH of humanized antibodies 15H3L2 and 15H3L3
EVQLLESGGGLVQPGGSLRLSCAASGFTFNTYAMNWVRQAPGKGLEWVA**RIRSKYNNYAT
YYAISVKDRFTISRDDSKNTLYLQMNSLRAEDTAMYYCVRHGNFGNSYLSYWAY**WGQGTL
VTVSS (SEQ ID NO: 10)

VL of mouse and chimeric 19-15 antibodies
QAVVTQESALTTSPGETVTLTCQSSTGAVTTNNYANWVQEKPDHLFTGLIGGTKQRAPGVP
ARFSGSLIGDKAALTITGAQTEDEAIYFCVLWYSNLWVFGGGTKLTVL (SEQ ID NO: 16)

VL of humanized antibodies 15H2L2 and 15H3L2
QTVVTQEPSLTVSPGGTVTLTCQSSTGAVTTNNYANWVQQKPGQAPRALIGGTKQRAPGTP
ARFSGSLLGGKAALTLSGVQPEDEAEYYCVLWYSNLWVFGGGTKLTVL (SEQ ID NO: 17)

VL of humanized antibodies 15H2L3 and 15H3L3
QAVVTQEPSLTVSPGGTVTLTCQSSTGAVTTNNYANWVQQKPGHAFRGLIGGTKQRAPGV
PARFSGSLLGGKAALTLSGVQPEDEAEYYCVLWYSNLWVFGGGTKLTVL (SEQ ID NO: 18)

VH of mouse and chimeric 19-26 antibodies
EVKLLESGGGLVQPKGSLKLSCAASGFTFNTYAMNWVRQAPGKGLEWVA**RIRSKYNNYAT
YYADSVKDRFTISRDDSQSILYLQMNNLKTEDTAMYYCVRHGNFGNSYISWWAY**WGQGTL
VTVSA (SEQ ID NO: 11)

VH of humanized antibody 26-H2L3
EVQLLESGGGLVQPGGSLRLSCAASGFTFNTYAMNWVRQAPGKGLEWVA**RIRSKYNNYAT
YYADSVKDRFTISRDNSKNTLYLQMNSLRAEDTAVYYCVKHGNFGNSYISWWAY**WGQGT
LVTVSS (SEQ ID NO: 12)

VH of humanized antibody 26-H3L3
EVQLLESGGGLVQPGGSLRLSCAASGFTFNTYAMNWVRQAPGKGLEWVA**RIRSKYNNYAT
YYADSVKDRFTISRDDSKNTLYLQMNSLRAEDTAMYYCVRHGNFGNSYISWWAY**WGQGT
LVTVSS (SEQ ID NO: 13)

VL of mouse and chimeric 19-26 antibodies
QAVVTQESALTTSPGETVTLTCKSSTGAVTTSNYANWVQEKPDHLFTGLIGGTNLHAPGVP
ARFSGSLIGDKAALTITGAQTEDEAIYFCALWYSNLWVFGGGTKLTVL (SEQ ID NO: 19)

VL of humanized antibodies 26-H2L3 and 26-H3L3
QAVVTQEPSLTVSPGGTVTLTCKSSTGAVTTSNYANWVQQKPGHAFRGLIGGTNLHAPGVP
ARFSGSLLGGKAALTLSGVQPEDEAEYYCALWYSNLWVFGGGTKLTVL (SEQ ID NO: 20)

VH of mouse and chimeric 19-37 antibodies
EVKLLESGGGLVQPKGSLKLSCAASGFTFNTYAMNWVRQAPGKGLEWVA**RIRSKYNNYAT
YYAISVKDRFTISRDDSQSILYLQMNNLKTEDTAMYYCVRHGNFGNSYISYWAY**WGQGTL
VTVSA (SEQ ID NO: 14)

VL of mouse and chimeric 19-37 antibodies
QAVVTQESALTTSPGETVTLTCRSSTGAVTTNNYANWVQEKPDHLFTGLIGGTRLSAPGVP
ARFSGSLIGDKAALTITGAQTEDEAIYFCVLWYSNLWVFGGGTKLTVL (SEQ ID NO: 21)

Human IgG1 - wildtype Fc, IgG1 Fc L234A/L235A, IgG1 Fc L234A/L235A/P329G, IgG1 Fc
L234A/L235A/N297A, IgG1 Fc L234A/L235A/N297A/P329G
ASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPEX1X2GGPSVFL
FPPKPKDTLMISRTPEVTCVVVDVSHEDPEVKFNWYVDGVEVHNAKTKPREEQYX3STYRV
VSVLTVLHQDWLNGKEYKCKVSNKALX4APIEKTISKAKGQPREPQVYTLPPSREEMTKNQV
SLTCLVKGFYPSDIAVEWESNGQPENNYKTTPPVLDSDGSFFLYSKLTVDKSRWQQGNVFSC
SVMHEALHNHYTQKSLSLSPGK (SEQ ID NO: 22)

human IgG1 - wildtype Fc
ASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPSREEMTKNQVSLTC
LVKGFYPSDIAVEWESNGQPENNYKTTPPVLDSDGSFFLYSKLTVDKSRWQQGNVFSCSVM
HEALHNHYTQKSLSLSPGK (SEQ ID NO: 22, X1 = L, X2 = L, X3 = N,
X4 = P)

| Description/Sequence/SEQ ID NO. |
| --- |

IgG1 Fc L234A/L235A
ASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPEAAGGPSVFLF
PPKPKDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQVSLT
CLVKGFYPSDIAVEWESNGQPENNYKTTPPVLDSDGSFFLYSKLTVDKSRWQQGNVFSCSV
MHEALHNHYTQKSLSLSPGK (SEQ ID NO: 22 X1 = A, X2 = A, X3 = N,
X4 = P)

IgG1 Fc L234A/L235A/P329G
ASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPEAAGGPSVFLF
PPKPKDTLMISRTPEVTCVVVDVSHEDPEVKFNWYVDGVEVHNAKTKPREEQYNSTYRVVS
VLTVLHQDWLNGKEYKCKVSNKALGAPIEKTISKAKGQPREPQVYTLPPSREEMTKNQVSLT
CLVKGFYPSDIAVEWESNGQPENNYKTTPPVLDSDGSFFLYSKLTVDKSRWQQGNVFSCSV
MHEALHNHYTQKSLSLSPGK (SEQ ID NO: 22, X1 = A, X2 = A, X3 = N,
X4 = G)

IgG1 Fc L234A/L235A/N297A
ASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPEAAGGPSVFLF
PPKPKDTLMISRTPEVTCVVVDVSHEDPEVKFNWYVDGVEVHNAKTKPREEQYASTYRVVS
VLTVLHQDWLNGKEYKCKVSNKALPAPIEKTISKAKGQPREPQVYTLPPSREEMTKNQVSLT
CLVKGFYPSDIAVEWESNGQPENNYKTTPPVLDSDGSFFLYSKLTVDKSRWQQGNVFSCSV
MHEALHNHYTQKSLSLSPGK (SEQ ID NO: 22, X1 = A, X2 = A, X3 = A,
X4 = P)

IgG1 Fc L234A/L235A/N297A/P329G
ASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPEAAGGPSVFLF
PPKPKDTLMISRTPEVTCVVVDVSHEDPEVKFNWYVDGVEVHNAKTKPREEQYASTYRVVS
VLTVLHQDWLNGKEYKCKVSNKALGAPIEKTISKAKGQPREPQVYTLPPSREEMTKNQVSLT
CLVKGFYPSDIAVEWESNGQPENNYKTTPPVLDSDGSFFLYSKLTVDKSRWQQGNVFSCSV
MHEALHNHYTQKSLSLSPGK (SEQ ID NO: 22, X1 = A, X2 = A, X3 = A,
X4 = G)

Human λ light chain constant region
GQPKAAPSVTLFPPSSEELQANKATLVCLISDFYPGAVTVAWKADSSPVKAGVETTTPSKQSN
NKYAASSYLSLTPEQWKSHRSYSCQVTHEGSTVEKTVAPTECS (SEQ ID NO: 23)

Human CD3 ε cDNA
ATGCAGTCGGGCACTCACTGGAGAGTTCTGGGCCTCTGCCTCTTATCAGTTGGCGTTTGG
GGGCAAGATGGTAATGAAGAAATGGGTGGTATTACACAGACACCATATAAAGTCTCCAT
CTCTGGAACCACAGTAATATTGACATGCCCTCAGTATCCTGGATCTGAAATACTATGGCA
ACACAATGATAAAAACATAGGCGGTGATGAGGATGATAAAAACATAGGCAGTGATGAG
GATCACCTGTCACTGAAGGAATTTTCAGAATTGGAGCAAAGTGGTTTTATGTCTGCTACC
CCAGAGGAAGCAAACCAGAAGATGCGAACTTTTATCTCTACCTGAGGGCAAGAGTGTGT
GAGAACTGCATGGAGATGGATGTGATGTCGGTGGCCACAATTGTCATAGTGGACATCTG
CATCACTGGGGGCTTGCTGCTGCTGGTTTACTACTGGAGCAAGAATAGAAAGGCCAAGG
CCAAGCCTGTGACACGAGGAGCGGGTGCTGGCGGCAGGCAAAGGGGACAAACAAGGA
GAGGCCACCACCTGTTCCCAACCCAGACTATGAGCCCATCCGGAAAGGCCAGCGGGACC
TGTATTCTGGCCTGAATCAGAGACGCATCTGA (SEQ ID NO: 24)

Human CD3δ cDNA
ATGGAACATAGCACGTTTCTCTCTGGCCTGGTACTGGCTACCCTTCTCTCGCAAGTGAGC
CCCTTCAAGATACCTATAGAGGAACTTGAGGACAGAGTGTTTGTGAATTGCAATACCAGC
ATCACATGGGTAGAGGGAACGGTGGGAACACTGCTCTCAGACATTACAAGACTGGACCT
GGGAAAACGCATCCTGGACCCACGAGGAATATATAGGTGTAATGGGACAGATATATACA
AGGACAAAGAATCTACCGTGCAAGTTCATTATCGAATGTGCCAGAGCTGTGTGGAGCTG
GATCCAGCCACCGTGGCTGGCATCATTGTCACTGATGTCATTGCCACTCTGCTCCTTGCTT
TGGGAGTCTTCTGCTTTGCTGGACATGAGACTGGAAGGCTGTCTGGGCGTGCCGACACAC
AAGCTCTGTTGAGGAATGACCAGGTCTATCAGCCCCTCCGAGATCGAGATGATGCTCAGT
ACAGCCACCTTGGAGGAAACTGGGCTCGGAACAAGTGA (SEQ ID NO: 25)

VH of MIL62
QVQLVQSGAEVKKPGSSVKVSCKASGYAFSYSWINWVRQAPGQGLEWMG**RIFPGDGDTD
YNGKFKGRVTITADKSTSTAYMELSSLRSEDTAVYYCARNVFDGYWLVY**WGQGTLVTVSS
(SEQ ID NO: 26)

VL of MIL62
DIVMTQTPLSLPVTPGEPASISCRSSKSLLHSNGITYLYWYLQKPGQSPQLLIYQMSNLVSGV
PDRFSGSGSGTDFTLKISRVEAEDVGVYYCAQNLELPYTFGGGTKVEIK (SEQ ID NO: 27)

Linker
GGGGSGGGGSGGGGS (SEQ ID NO: 28)

| Description/Sequence/SEQ ID NO. |
|---|
| MIL62 VH-linker-MIL62 VL-linker-15H2L3 VH<br>QVQLVQSGAEVKKPGSSVKVSCKASGYAFSYSWINWVRQAPGQGLEWMGRIFPGDGDTD<br>YNGKFKGRVTITADKSTSTAYMELSSLRSEDTAVYYCARNVFDGYWL VYWGQGTLVTVSS<br>GGGGSGGGGSGGGGSDIVMTQTPLSLPVTPGEPASISCRSSKSLLHSNGITYLYWYLQKPGQ<br>SPQLLIYQMSNLVSGVPDRFSGSGSGTDFTLKISRVEAEDVGVYYCAQNLELPYTFGGGTKV<br>EIKGGGGSGGGGSGGGGSEVQLLESGGGLVQPGGSLRLSCAASGFTFNTYAMNWVRQAPG<br>KGLEWVARIRSKYNNYATYYAISVKDRFTISRDNSKNTLYLQMNSLRAEDTAVYYCVKHG<br>NFGNSYLSYWAYWGQGTLVTVSS (SEQ ID NO: 29) |
| MIL62 VH-linker-MIL62 VL-linker-15H3L3 VH<br>QVQLVQSGAEVKKPGSSVKVSCKASGYAFSYSWINWVRQAPGQGLEWMGRIFPGDGDTD<br>YNGKFKGRVTITADKSTSTAYMELSSLRSEDTAVYYCARNVFDGYWL VYWGQGTLVTVSS<br>GGGGSGGGGSGGGGSDIVMTQTPLSLPVTPGEPASISCRSSKSLLHSNGITYLYWYLQKPGQ<br>SPQLLIYQMSNLVSGVPDRFSGSGSGTDFTLKISRVEAEDVGVYYCAQNLELPYTFGGGTKV<br>EIKGGGGSGGGGSGGGGSEVQLLESGGGLVQPGGSLRLSCAASGFTFNTYAMNWVRQAPG<br>KGLEWVARIRSKYNNYATYYAISVKDRFTISRDDSKNTLYLQMNSLRAEDTAMYYCVRHG<br>NFGNSYLSYWAYWGQGTLVTVSS (SEQ ID NO: 30) |
| Light chain constant region of MIL220 and MIL62<br>RTVAAPSVFIFPPSDEQLKSGTASVVCLLNNFYPREAKVQWKVDNALQSGNSQESVTEQDSK<br>DSTYSLSSTLTLSKADYEKHKVYACEVTHQGLSSPVTKSFNRGEC (SEQ ID NO: 31) |
| Light chain constant region of MIL221-1 and MIL221-2<br>GQPKAAPSVTLFPPSSEELQANKATLVCLISDFYPGAVTVAWKADSSPVKAGVETTTPSKQSN<br>NKYAASSYLSLTPEQWKSHRSYSCQVTHEGSTVEKTVAPT (SEQ ID NO: 32) |
| Heavy chain constant region of MIL220<br>ASTKGPSVFPLAPSSKSTSGGTAALGCLVKDYFPEPVTVSWNSGALTSGVHTFPAVLQSSGLY<br>SLSSVVTVPSSSLGTQTYICNVNHKPSNTKVDKKVEPKSCDKTHTCPPCPAPEAAGGPSVFLF<br>PPKPKDTLMISRTPEVTCVVVDVSHEDPEVKFNWYVDGVEVHNAKTKPREEQYASTYRVVS<br>VLTVLHQDWLNGKEYKCKVSNKALPAPIEKTISKAKGQPREPQVYTLPPSREEMTKNQVSLS<br>CAVKGFYPSDIAVEWESNGQPENNYKTTPPVLDSDGSFFLVSKLTVDKSRWQQGNVFSCSV<br>MHEALHNHYTQKSLSLSPGK (SEQ ID NO: 33) |
| Heavy chain constant region of MIL221-1 and 221-2<br>ASTKGPSVFPLAPSSKSTSGGTAALGCLVKDYFPEPVTVSWNSGALTSGVHTFPAVLQSSGLY<br>SLSSVVTVPSSSLGTQTYICNVNHKPSNTKVDKKVEPKSCDKTHTCPPCPAPEAAGGPSVFLF<br>PPKPKDTLMISRTPEVTCVVVDVSHEDPEVKFNWYVDGVEVHNAKTKPREEQYASTYRVVS<br>VLTVLHQDWLNGKEYKCKVSNKALPAPIEKTISKAKGQPREPQVYTLPPSREEMTKNQVSL<br>WCLVKGFYPSDIAVEWESNGQPENNYKTTPPVLDSDGSFFLYSKLTVDKSRWQQGNVFSCS<br>VMHEALHNHYTQKSLSLSPGK (SEQ ID NO: 34) |
| Human CD20<br>MTTPRNSVNGTFPAEPMKGPIAMQSGPKPLFRRMSSLVGPTQSFFMRESKTLGAVQIMNGLF<br>HIALGGLLMIPAGIYAPICVTVWYPLWGGIMYIISGSLLAATEKNSRKCLVKGKMIMNSLSLF<br>AAISGMILSIMDILNIKISHFLKMESLNFIRAHTPYINIYNCEPANPSEKNSPSTQYCYSIQSLFLG<br>ILSVMLIFAFFQELVIAGIVENEWKRTCSRPKSNIVLLSAEEKKEQTIEIKEEVVGLTETSSQPK<br>NEEDIEIIPIQEEEEEETETNFPEPPQDQESSPIENDSSP (SEQ ID NO: 35) |
| Monkey CD20<br>MTTPRNSVNGTFPAEPMKGPIAMQPGPKPLLRRMSSLVGPTQSFFMRESKALGAVQIMNGLF<br>HIALGGLLMIPAGIYAPICVTVWYPLWGGIMYIISGSLLAATEKNSRKCLVKGKMIMNSLSLF<br>AAISGMILSIMDILNIKISHFLKMESLNFIRVHTPYINIYYCEPANPSEKNSPSTQYCYSIQSLFLG<br>ILSVMLIFAFFQELVIAGIVENEWRRTCSRPKSSVVLLSAEEKKEQVIEIKEEVVGLTETSSQPK<br>NEEDIEIIPIQEEEEEETETNFPEPPQDQESSPIENDSSP (SEQ ID NO: 36) |
| Human CD16A<br>MWQLLLPTALLLLVSAGMRTEDLPKAVVFLEPQWYRVLEKDSVTLKCQGAYSPEDNSTQW<br>FHNESLISSQASSYFIDAATVDDSGEYRCQTNLSTLSDPVQLEVHIGWLLLQAPRWVFKEEDPI<br>HLRCHSWKNTALHKVTYLQNGKGRKYFHHNSDFYIPKATLKDSGSYFCRGLVGSKNVSSET<br>VNITITQGLAVSTISSFFPPGYQVSFCLVMVLLFAVDTGLYFSVKTNIRSSTRDWKDHKFKWR<br>KDPQDK (SEQ ID NO: 37) |
| Human CD32A<br>MTMETQMSQNVCPRNLWLLQPLTVLLLLASADSQAAAPPKAVLKLEPPWINVLQEDSVTLT<br>CQGARSPESDSIQWFHNGNLIPTHTQPSYRFKANNNDSGEYTCQTGQTSLSDPVHLTVLSEW<br>LVLQTPHLEFQEGETIMLRCHSWKDKPLVKVTFFQNGKSQKFSHLDPTFSIPQANHSHSGDY<br>HCTGNIGYTLFSSKPVTITVQVPSMGSSSPMGIIVAVVIATAVAAIVAAVVALIYCRKKRISAN<br>STDPVKAAQFEPPGRQMIAIRKRQLEETNNDYETADGGYMTLNPRAPTDDDKNIYLTLPPND<br>HVNSNN (SEQ ID NO: 38) |
| Human CD32B<br>MGILSFLPVLATESDWADCKSPQPWGHMLLWTAVLFLAPVAGTPAAPPKAVLKLEPQWINV<br>LQEDSVTLTCRGTHSPESDSIQWFHNGNLIPTHTQPSYRFKANNNDSGEYTCQTGQTSLSDPV<br>HLTVLSEWLVLQTPHLEFQEGETIVLRCHSWKDKPLVKVTFFQNGKSKKFSRSDPNFSIPQAN |

| Description/Sequence/SEQ ID NO. |
|---|
| HSHSGDYHCTGNIGYTLYSSKPVTITVQAPSSSPMGIIVAVVTGIAVAAIVAAVVALIYCRKKR<br>ISALPGYPECREMGETLPEKPANPTNPDEADKVGAENTITYSLLMHPDALEEPDDQNRI (SEQ<br>ID NO: 39) |
| Human CD64<br>MWFLTTLLLWVPVDGQVDTTKAVITLQPPWVSVFQEETVTLHCEVLHLPGSSSTQWFLNGT<br>ATQTSTPSYRITSASVNDSGEYRCQRGLSGRSDPIQLEIHRGWLLLQVSSRVFTEGEPLALRCH<br>AWKDKLVYNVLYYRNGKAFKFFHWNSNLTILKTNISHNGTYHCSGMGKHRYTSAGISVTVK<br>ELFPAPVLNASVTSPLLEGNLVTLSCETKLLLQRPGLQLYFSFYMGSKTLRGRNTSSEYQILTA<br>RREDSGLYWCEAATEDGNVLKRSPELELQVLGLQLPTPVWFHVLFYLAVGIMFLVNTVLWV<br>TIRKELKRKKKWDLEISLDSGHEKKVISSLQEDRHLEEELKCQEQKEEQLQEGVHRKEPQGA<br>T (SEQ ID NO: 40) |

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An isolated monoclonal antibody, or an antigen-binding portion thereof, capable of binding to CD3, comprising a heavy chain variable region comprising a VH CDR1 region, a VH CDR2 region and a VH CDR3 region, and a light chain variable region comprising a VL CDR1 region, a VL CDR2 region and a VL CDR3 region, wherein the VH CDR1 region comprises the amino acid sequence $X_1$YAMN (SEQ ID NO: 1), wherein $X_1$ is Thr (T), the VH CDR2 region comprises the amino acid sequence RIRSKYNNYATYYAX$_1$SV (SEQ ID NO:2), wherein $X_1$ is Be (I), the VH CDR3 region comprises the amino acid sequence HGNFGNSYX$_1$SX$_2$WAY (SEQ ID NO: 3), wherein $X_1$ and $X_2$ are Leu (L) and Tyr (Y), respectively, the VL CDR1 region comprises the amino acid sequence $X_1$SSTGAVTTX$_2$NYAN (SEQ ID NO: 4), wherein $X_1$ and $X_2$ are Gln (Q) and Asn (N), respectively, the VL CDR2 region comprises the amino acid sequence GTX$_1$X$_2$X$_3$AP (SEQ ID NO: 5), wherein $X_1$, $X_2$ and $X_3$ are Lys (K), Gln (Q) and Arg (R), respectively, and the VL CDR3 region comprises the amino acid sequence $X_1$LWYSNLWV (SEQ ID NO: 6), wherein $X_1$ is Val (V).

2. The isolated monoclonal antibody, or the antigen-binding portion thereof of claim 1, wherein the heavy chain variable region comprises an amino acid sequence having at least 95% identity to EVKLLESGGGLVQPKGSLKLSCAASGFTFNTYAMNWVRQAPGKGLEWVARIRSKYNN YATYYAISVKDRFTISRDDSQSILYLQMNNLKTEDTAMYYCVRHGNFGNSYLSYWA YW GQGTLVTVSA (SEQ ID NO: 8), EVQLLESGGGLVQPGGSLRLSCAASGFTFNTYAMNWVRQAPGKGLEWVARIRSKYNN YATYYAISVKDRFTISRDNSKNTLYLQMNSLRAEDTAVYYCVKHGNFGNS YLSYWAY WGQGTLVTVSS (SEQ ID NO: 9), or EVQLLESGGGLVQPGGSLRLSCAASGFTFNTYAMNWVRQAPGKGLEWVARIRSKYNN YATYYAISVKDRFTISRDDSKNTLYLQMNSLRAEDTAMYYCVRHGNFGNSYLSYWAY WGQGTLVTVSS (SEQ ID NO: 10).

3. The isolated monoclonal antibody, or the antigen-binding portion thereof of claim 1, wherein the light chain variable region comprises an amino acid sequence having at least 95% identity to QAVVTQESALTTSPGETVTLTCQSSTGAVTTN-NYANWVQEKPDHLFTGLIGGTKQRAPG VPARFSGSLIGDKAALTITGAQTEDEAIYFCVLWYSNLWVFGGG TKLTVL (SEQ ID NO: 16), QTVVTQEPSLTVSPGGTVTLTCQSSTGAVTTN-NYANWVQQKPGQAPRALIGGTKQRAP GTPARFSGSLLGGKAALTLSGVQPEDE-AEYYCVLWYSNLWVFGGGTKLTVL (SEQ ID NO: 17) or QAVVTQEPSLTVSPGGTVTLTCQSSTGAVTTN-NYANWVQQKPGHAFRGLIGGTKQRAP GVPARFSGSLLGGKAALTLSGVQPEDE-AEYYCVLWYSNLWVFGGGTKLTVL(SEQ ID NO: 18).

4. The isolated monoclonal antibody, or the antigen-binding portion thereof of claim 2, wherein the heavy chain variable region and the light chain variable region comprise amino acid sequences having at least 95% identity to (1) EVKLLESGGGLVQPKGSLKLSCAASGFTFNTYAMNWVRQAPGKGLEWVARI RSKYN-NYATYYAISVKDRFTISRDDSQSILYLQMNNLKT-EDTAMYYCVRHGNFGNSYL SYWAYWGQGTLVTVSA (SEQ ID NO: 8) and QAVVTQESALTTSPGETVTLTCQSSTGAV TTN-NYANWVQEKPDHLFTGLIGGTKQRAPGVPARFS GSLIGDKAALTITGAQTEDEAIYF CVLWYSNLWVFGGGTKLTVL (SEQ ID NO: 16), respectively;

(2) EVQLLESGGGLVQPGGSLRLSCAASGFTFNTYAMNWVRQAPGKGLEWVARI RSKYN-NYATYYAISVKDRFTISRDNSKNTLYLQMNSL-RAEDTAVYYCVKHGNFGNSYL SYWAYWGQGTLVTVSS (SEQ ID NO: 9) and QTVVTQEPSLTVSPGGTVTLTCQSSTGAV TTN-NYANWVQQKPGQAPRALIGGTKQRAPGT-PARFSGSLLGGKAALTLSGVQPEDEAE YYCVLWYSNLWVFGGGTKLTVL (SEQ ID NO: 17), respectively;

(3) EVQLLESGGGLVQPGGSLRLSCAASGFTFNTYAMNWVRQAPGKGLEWVARI RSKYN-NYATYYAISVKDRFTISRDNSKNTLYLQMNSL-RAEDTAVYYCVKHGNFGNSYL SYWAYWGQGTLVTVSS (SEQ ID NO: 9) and QAVVTQEPSLTVSPGGTVTLTCQSSTGAV TTN-NYANWVQQKPGHAFR- GLIGGTKQRAPGVPARFSGSLLGG-KAALTLSGVQPEDEAE YYCVLWYSNLWVFGGGTKLTVL (SEQ ID NO: 18), respectively;

(4) EVQLLESGGGLVQPGGSLRLSCAASGFTFN-TYAMNWVRQAPGKGLEWVARI RSKYN-NYATYYAISVKDRFTISRDDSKNTLYLQMNSL-RAEDTAMYYCVRHGNFGNSYL SYWAYWGQGTLVTVSS (SEQ ID NO: 10) and QTVVTQEPSLTVSPGGTVTLTCQSSTGA VTTN-NYANWVQQKPGQAPRALIGGTKQRAPGT-PARFSGSLLGGKAALTLSGVQPEDEA EYYCVLWYSNLWVFGGGTKLTVL (SEQ ID NO: 17), respectively; or (5) EVQLLESGGGLVQPGGSLRLSCAASGFTFN-TYAMNWVRQAPGKGLEWVARI RSKYN-NYATYYAISVKDRFTISRDDSKNTLYLQMNSL-RAEDTAMYYCVRHGNFGNSYL SYWAYWGQGTLVTVSS (SEQ ID NO: 10) and QAVVTQEPSLTVSPGGTVTLTCQSSTGA VTTN-NYANWVQQKPGHAFR-GLIGGTKQRAPGVPARFSGSLLGG-KAALTLSGVQPEDEA EYYCVLWYSNLWVFGGGTKLTVL (SEQ ID NO: 18), respectively.

5. The isolated monoclonal antibody, or the antigen-binding portion thereof of claim 1, comprising
i) a heavy chain constant region having the amino acid sequence ASTKGPSVFPLAPSSKSTSGGTAAL-GCLVKDYFPEPVTVSWNSGALT-SGVHTFPAVLQSS GLYS-LSSVVTVPSSSLGTQTYICNVNHKPSNTKV DKKVEPKSCDKTHTCPPCPAPEX$_1$X$_2$G GPSVFLFPPKPKDTLMISRTPE-VTCVVVDVSSHEDPE-VKFNWYVDGVEVHNAKTKPREEQ YX$_3$STYRVVSVLTVLHQDWLNGKEYKCKVSNK ALX$_4$APIEKTISKAKGQPREPQVYTLP PSREEMT-KNQVSLTCLVKGFYPSDIAVEWESNGQPEN-NYKTTPPVLDSDGSFFLYSKLT VDKSRWQQGNVFSCSVMHEALHN-HYTQKSLSLSPGK (SEQ ID NO: 22) wherein X$_1$, X$_2$, X$_3$ and X$_4$ are A, A, N and P, respectively; A, A, N and G, respectively; A, A, A and P, respectively; or A, A, A and G, respectively, linked to the heavy chain variable region, and
ii) a light chain constant region having the amino acid sequence GQPKAAPSVTLFPPS-SEELQANKATLVCLISDFYP-GAVTVAWKADSSPVKAGVETTTPS KQSNNKYAASSYLSLTPEQWKSHRSYS-CQVTHEGSTVEKTVAPTECS (SEQ ID NO: 23) or GQPKAAPSVTLFPPSSEELQANKATLVCLIS-DFYPGAVTVAWKADSSPVKAGVETTTPS KQSNNKYAASSYLSLTPEQWKSHRSYS-CQVTHEGSTVEKTVAPT (SEQ ID NO: 32), linked to the light chain variable region.

6. A bispecific antibody, comprising
i) an antigen binding domain against CD3, which comprises the isolated monoclonal antibody or the antigen binding portion thereof of claim 1, and
ii) an antigen binding domain against a disease associated antigen, wherein the disease associated antigen is a tumor associated antigen, an infectious disease associated antigen, or an inflammatory disease associated antigen,
wherein the antigen binding domain against CD3 is linked to the antigen binding domain against a disease associated antigen.

7. The bispecific antibody of claim 6, wherein the disease associated antigen is CD20 protein, and the antigen binding domain against CD20 protein comprises an antibody or an antigen-binding portion thereof that binds CD20 protein, wherein the antibody or antigen-binding portion thereof that binds CD20 protein comprises a heavy chain variable region and a light chain variable region.

8. The bispecific antibody of claim 7, comprising one antigen binding domain against CD3 and two antigen binding domains against CD20 protein.

9. The bispecific antibody of claim 8, comprising
i) a first polypeptide, comprising an anti-CD20 heavy chain variable region and a heavy chain constant region,
ii) a second polypeptide, comprising an anti-CD20 light chain variable region,
iii) a third polypeptide, comprising an anti-CD20 heavy chain variable region, an anti-CD20 light chain variable region, an anti-CD3 heavy chain variable region, and a heavy chain constant region, and
iv) a fourth polypeptide, comprising an anti-CD3 light chain variable region,
wherein the anti-CD20 heavy chain variable region in the first polypeptide and the anti-CD20 light chain variable region in the second polypeptide associate to form the antigen binding fragment against CD20 protein,
wherein the anti-CD20 heavy chain variable region and the anti-CD20 light chain variable region in the third polypeptide associate to form the antigen binding fragment against CD20 protein,
wherein the anti-CD3 heavy chain variable region in the third polypeptide and the anti-CD3 light chain variable region in the fourth polypeptide associate to form an antigen binding fragment against CD3,
wherein the heavy chain constant region in the first polypeptide and the heavy chain constant region in the third polypeptide are associated together.

10. The bispecific antibody of claim 9, wherein the anti-CD20 heavy chain variable region contained in the first and third polypeptides comprises the amino acid sequence QVQLVQSGAEVKKPGSSVKVSCKASGYAFSYS-WINWVRQAPGQGLEWMGRIFPGDGD TDYN-GKFKGRVTITADKSTSTAYMELSSLRSEDTAVYY-CARNVFDGYWLVYWGQGTL VTVSS (SEQ ID NO: 26), and the anti-CD20 light chain variable region contained in the second and third polypeptides comprises the amino acid sequence DIVMTQTPLSLPVTPGEPASIS-CRSSKSLLHSNGITY-LYWYLQKPGQSPQLLIYQMSNLVS GVPDRFSGSGSGTDFTLKISRVEAEDVGVYYCAQN-LELPYTFGGGTKVEIK (SEQ ID NO: 27).

11. The bispecific antibody of claim 9, wherein the heavy chain constant region in the first polypeptide comprises the amino acid sequence ASTKGPSVFPLAPSSKST-SGGTAALGCLVKDYFPEPVTVSWNSGALT-SGVHTFPAVLQSS GLYS-LSSVVTVPSSSLGTQTYICNVNHKPSNTKVDKKVEP KSCDKTHTCPPCPAPEAAG GPSVFLFPPKPKDTLMIS-RTPEVTCVVVDVSSHEDPE-VKFNWYVDGVEVHNAKTKPREEQ YASTYRVVSVLTVLHQDWLNGKEYKCKVSNKALPA-PIEKTISKAKGQPREPQVYTLPPS REEMTKNQVSLS-CAVKGFYPSDIAVEWESNGQPEN-NYKTTPPVLDSDGSFFLVSKLTVD KSRWQQGNVFSCSVMHEALHNHYTQKSLSLSPGK (SEQ ID NO: 33), and the heavy chain constant region in the third polypeptide comprises the amino acid sequence ASTKGPSVFPLAPSSKSTSGGTAALGCLVKDYFPEPVTVSWNSGALTSGVHTFPAVLQSS GLYSLSSVVTVPSSSLGTQTYICNVNHKPSNTKVDKKVEPKSCDKTHTCPPCPAPEAAG GPSVFLFPPKPKDTLMISRTPEVTCVVVDVSSHEDPEVKFNWYVDGVEVHNAKTKPREEQ YASTYRVVSVLTVLHQDWLNGKEYKCKVSNKALPAPIEKTISKAKGQPREPQVYTLPPS REEMTKNQVSLWCLVKGFYPSDIAVEWESNGQPENNYKTTPPVLDSDGSFFLYSKLTV DKSRWQQGNVFSCSVMHEALHNHYTQKSLSLSPGK (SEQ ID NO: 34).

12. The bispecific antibody of claim 9, wherein the first polypeptide comprises, from N terminus to C terminus, the anti-CD20 heavy chain variable region and the heavy chain constant region, and the third polypeptide comprises, from N terminus to C terminus, the anti-CD20 heavy chain variable region, the anti-CD20 light chain variable region, the anti-CD3 heavy chain variable region, and the heavy chain constant region; or the first polypeptide comprises, from N terminus to C terminus, the anti-CD20 heavy chain variable region and the heavy chain constant region, and the third polypeptide comprises, from N terminus to C terminus, the anti-CD20 light chain variable region, the anti-CD20 heavy chain variable region, the anti-CD3 heavy chain variable region, and the heavy chain constant region.

13. The bispecific antibody of claim 12, wherein the anti-CD20 heavy chain variable region is linked, via a linker comprising the amino acid sequence GGGGSGGGGSGGGGS (SEQ ID NO: 28), to the anti-CD20 light chain variable region, and the anti-CD20 light chain variable region is linked, via a linker comprising the amino acid sequence GGGGSGGGGSGGGGS (SEQ ID NO: 28), to the anti-CD3 heavy chain variable region.

14. The bispecific antibody of claim 13, wherein the third polypeptide comprises the amino acid sequence QVQLVQSGAEVKKPGSSVKVSCKASGYAFSYSWINWVRQAPGQGLEWMGRIFPGDGD TDYNGKFKGRVTITADKSTSTAYMELSSLRSEDTAVYYCARNVFDGYWLVYWGQGTL VTVSSGGGGSGGGGSGGGGSDIVMTQTPLSLPVTPGEPASISCRSSKSLLHSNGITYLYW YLQKPGQSPQLLIYQMSNLVSGVPDRFSGSGSGTD FTLKISRVEAEDVGVYYCAQNLEL PYTFGGGTKVEIKGGGGSGGGGSGGGGSEVQLLESGGGLVQPGGSLRLSCAASGFTFNT YAMNWVRQAPGKGLEWVARIRSKYNNYATYYAISVKDRFTISRDNSKNTLYLQMNSL RAEDTAVYYCVKHGNFGNSYLSYWAYWGQGTLVTVSS (SEQ ID NO: 29) or QVQLVQSGAEVKKPGSSVKVSCKASGYAFSYSWINWVRQAPGQGLEWMGRIFPGDGD TDYNGKFKGRVTITADKSTSTAYMELSSLRSEDTAVYYCARNVFDGYWLVYWGQGTL VTVSSGGGGSGGGGSGGGGSDIVMTQTPLSLPVTPGEPASISCRSSKSLLHSNGITYLYW YLQKPGQSPQLLIYQMSNLVSGVPDRFSGSGSGTD FTLKISRVEAEDVGVYYCAQNLEL PYTFGGGTKVEIKGGGGSGGGGSGGGGSEVQLLESGGGLVQPGGSLRLSCAASGFTFNT YAMNWVRQAPGKGLEWVARIRSKYN-NYATYYAISVKDRFTISRDDSKNTLYLQMNSL RAEDTAMYYCVRHGNFGNSYLSYWAYWGQGTLVTVSS (SEQ ID NO: 30).

15. The bispecific antibody of claim 9, wherein the second polypeptide further comprises at the C terminus a light chain constant region comprising the amino acid sequence RTVAAPSVFIFPPSDEQLKSGTASVVCLLNNFYPREAKVQWKVDNALQSGNSQESVTEQ DSKDSTYSLSSTLTLSKADYEKHKVYACEVTHQGLSSPVTKSFNRGEC (SEQ ID NO: 31), and the fourth polypeptide further comprises at the C terminus a light chain constant region comprising the amino acid sequence GQPKAAPSVTLFPPSSEELQANKATLVCLISDFYPGAVTVAWKADSSPVKAGVETTTPS KQSNNKYAASSYLSLTPEQWKSHRSYSCQVTHEGSTVEKTVAPT (SEQ ID NO: 32).

16. A pharmaceutical composition comprising a pharmaceutically effective amount of the isolated monoclonal antibody or the antigen-binding portion thereof of claim 1, and a pharmaceutically acceptable carrier.

17. An isolated monoclonal antibody, or an antigen-binding portion thereof, capable of binding to CD3, comprising a heavy chain variable region and a light chain variable region, wherein the heavy chain variable region and the light chain variable region comprise the amino acid sequences (1) EVKLLESGGGLVQPKGSLKLSCAASGFTFNTYAMNWVRQAPGKGLEWVARI RSKYNNYATYYAISVKDRFTISRDDSQSILYLQMNNLKTEDTAMYYCVRHGNFGNSYL SYWAYWGQGTLVTVSA (SEQ ID NO: 8) and QAVVTQESALTTSPGETVTLTCQSSTGAV TTNNYANWVQEKPDHLFTGLIGGTKQRAPGVPARF SGSLIGDKAALTITGAQTEDEAIYF CVLWYSNLWVFGGGTKLTVL (SEQ ID NO: 16), respectively;

(2) EVQLLESGGGLVQPGGSLRLSCAASGFTFNTYAMNWVRQAPGKGLEWVARI RSKYNNYATYYAISVKDRFTISRDNSKNTLYLQMNSL-RAEDTAVYYCVKHGNFGNSYL SYWAYWGQGTLVTVSS (SEQ ID NO: 9) and QTVVTQEPSLTVSPGGTVTLTCQSSTGAV TTNNYANWVQQKPGQAPRALIGGTKQRAPGTPARFSGSLLGGKAALTLSGVQPEDEAE YYCVLWYSNLWVFGGGTKLTVL (SEQ ID NO: 17), respectively;

(3) EVQLLESGGGLVQPGGSLRLSCAASGFTFNTYAMNWVRQAPGKGLEWVARI RSKYNNYATYYAISVKDRFTISRDNSKNTLYLQMNSL-RAEDTAVYYCVKHGNFGNSYL SYWAYWGQGTLVTVSS (SEQ ID NO: 9) and QAVVTQEPSLTVSPGGTVTLTCQSSTGAV TTNNYANWVQQKPGHAFR-GLIGGTKQRAPGVPARFSGSLLGG-KAALTLSGVQPEDEAE YYCVLWYSNLWVFGGGTKLTVL(SEQ ID NO: 18), respectively;

(4) EVQLLESGGGLVQPGGSLRLSCAASGFTFNTYAMNWVRQAPGKGLEWVARI RSKYNNYATYYAISVKDRFTISRDDSKNTLYLQMNSL-RAEDTAMYYCVRHGNFGNSYL SYWAYWGQGTLVTVSS (SEQ ID NO: 10) and QTVVTQEPSLTVSPGGTVTLTCQSSTGA VTTNNYANWVQQKPGQAPRALIGGTKQRAPGTPARFSGSLLGGKAALTLSGVQPEDEA EYYCVLWYSNLWVFGGGTKLTVL (SEQ ID NO: 17), respectively; or (5) EVQLLESGGGLVQPGGSLRLSCAASGFTFN-TYAMNWVRQAPGKGLEWVARI RSKYN-NYATYYAISVKDRFTISRDDSKNTLYLQMNSL-RAEDTAMYYCVRHGNFGNSYL SYWAYWGQGTLVTVSS (SEQ ID NO: 10) and QAVVTQEPSLTVSPGGTVTLTCQSSTGA VTTN-NYANWVQQKPGHAFR-GLIGGTKQRAPGVPARFSGSLLGG-KAALTLSGVQPEDEA EYYCVLWYSNLWVFGGGTKLTVL(SEQ ID NO: 18), respectively.

\* \* \* \* \*

SEQUENCE LISTING

```
<160> NUMBER OF SEQ ID NOS: 40

<210> SEQ ID NO 1
<211> LENGTH: 5
<212> TYPE: PRT
<213> ORGANISM: Artificial Sequence
<220> FEATURE:
<223> OTHER INFORMATION: VH-CDR1 of mouse and chimeric CD3-19 and 19-37,
      mouse, chimeric and humanized 19-15 and 19-26
<220> FEATURE:
<221> NAME/KEY: misc_feature
<222> LOCATION: (1)..(1)
<223> OTHER INFORMATION: Xaa can be Ser or Thr

<400> SEQUENCE: 1

Xaa Tyr Ala Met Asn
1               5

<210> SEQ ID NO 2
<211> LENGTH: 17
<212> TYPE: PRT
<213> ORGANISM: Artificial Sequence
<220> FEATURE:
<223> OTHER INFORMATION: VH-CDR2 of mouse and chimeric CD3-19 and 19-37,
      mouse, chimeric and humanized 19-15 and 19-26
<220> FEATURE:
<221> NAME/KEY: misc_feature
<222> LOCATION: (15)..(15)
<223> OTHER INFORMATION: Xaa can be Asp or Ile

<400> SEQUENCE: 2

Arg Ile Arg Ser Lys Tyr Asn Asn Tyr Ala Thr Tyr Tyr Ala Xaa Ser
1               5                   10                  15

Val

<210> SEQ ID NO 3
<211> LENGTH: 14
<212> TYPE: PRT
<213> ORGANISM: Artificial Sequence
<220> FEATURE:
<223> OTHER INFORMATION: VH-CDR3 of mouse and chimeric CD3-19 and 19-37,
      mouse, chimeric and humanized 19-15 and 19-26
<220> FEATURE:
<221> NAME/KEY: misc_feature
<222> LOCATION: (9)..(9)
<223> OTHER INFORMATION: Xaa can be Leu or Ile
<220> FEATURE:
<221> NAME/KEY: misc_feature
<222> LOCATION: (11)..(11)
```

```
<223> OTHER INFORMATION: Xaa can be Tyr or Trp

<400> SEQUENCE: 3

His Gly Asn Phe Gly Asn Ser Tyr Xaa Ser Xaa Trp Ala Tyr
1               5                   10

<210> SEQ ID NO 4
<211> LENGTH: 14
<212> TYPE: PRT
<213> ORGANISM: Artificial Sequence
<220> FEATURE:
<223> OTHER INFORMATION: VL-CDR1 of mouse and chimeric CD3-19 and 19-37,
      mouse, chimeric and humanized 19-15 and 19-26
<220> FEATURE:
<221> NAME/KEY: misc_feature
<222> LOCATION: (1)..(1)
<223> OTHER INFORMATION: Xaa can be Asp, Gln, Lys or Arg
<220> FEATURE:
<221> NAME/KEY: misc_feature
<222> LOCATION: (10)..(10)
<223> OTHER INFORMATION: Xaa can be Ser or Asn

<400> SEQUENCE: 4

Xaa Ser Ser Thr Gly Ala Val Thr Thr Xaa Asn Tyr Ala Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: VL-CDR2 of mouse and chimeric CD3-19 and 19-37,
      mouse, chimeric and humanized 19-15 and 19-26
<220> FEATURE:
<221> NAME/KEY: misc_feature
<222> LOCATION: (3)..(3)
<223> OTHER INFORMATION: Xaa can be Gln, Lys, Asn or Arg
<220> FEATURE:
<221> NAME/KEY: misc_feature
<222> LOCATION: (4)..(4)
<223> OTHER INFORMATION: Xaa can be Arg, Gln or Leu
<220> FEATURE:
<221> NAME/KEY: misc_feature
<222> LOCATION: (5)..(5)
<223> OTHER INFORMATION: Xaa can be Ser, Arg or His

<400> SEQUENCE: 5

Gly Thr Xaa Xaa Xaa Ala Pro
1               5

<210> SEQ ID NO 6
<211> LENGTH: 9
<212> TYPE: PRT
<213> ORGANISM: Artificial Sequence
<220> FEATURE:
<223> OTHER INFORMATION: VL-CDR3 of mouse and chimeric CD3-19 and 19-37,
      mouse, chimeric and humanized 19-15 and 19-26
<220> FEATURE:
<221> NAME/KEY: misc_feature
<222> LOCATION: (1)..(1)
<223> OTHER INFORMATION: Xaa can be Val or Ala

<400> SEQUENCE: 6

Xaa Leu Trp Tyr Ser Asn Leu Trp Val
1               5

<210> SEQ ID NO 7
<211> LENGTH: 125
<212> TYPE: PRT
<213> ORGANISM: Artificial Sequence
<220> FEATURE:
```

<223> OTHER INFORMATION: VH of mouse and chimeric CD3-19

<400> SEQUENCE: 7

```
Glu Val Lys Leu Leu Glu Ser Gly Gly Gly Leu Val Gln Pro Lys Gly
1               5                   10                  15

Ser Leu Lys Leu Ser Cys Ala Ala Ser Gly Phe Thr Phe Asn Ser Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Leu Ser Tyr Trp
            100                 105                 110

Ala Tyr Trp Gly Gln Gly Thr Leu Val Thr Val Ser Ala
        115                 120                 125
```

<210> SEQ ID NO 8
<211> LENGTH: 125
<212> TYPE: PRT
<213> ORGANISM: Artificial Sequence
<220> FEATURE:
<223> OTHER INFORMATION: VH of mouse and chimeric 19-15

<400> SEQUENCE: 8

```
Glu Val Lys Leu Leu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Ile
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Leu Ser Tyr Trp
            100                 105                 110

Ala Tyr Trp Gly Gln Gly Thr Leu Val Thr Val Ser Ala
        115                 120                 125
```

<210> SEQ ID NO 9
<211> LENGTH: 125
<212> TYPE: PRT
<213> ORGANISM: Artificial Sequence
<220> FEATURE:
<223> OTHER INFORMATION: VH of 15H2L2 and 15H2L3

<400> SEQUENCE: 9

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
```

```
            35                  40                  45

Ala Arg Ile Arg Ser Lys Tyr Asn Asn Tyr Ala Thr Tyr Tyr Ala Ile
 50                  55                  60

Ser Val Lys Asp Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Lys His Gly Asn Phe Gly Asn Ser Tyr Leu Ser Tyr Trp
            100                 105                 110

Ala Tyr Trp Gly Gln Gly Thr Leu Val Thr Val Ser Ser
            115                 120                 125

<210> SEQ ID NO 10
<211> LENGTH: 125
<212> TYPE: PRT
<213> ORGANISM: Artificial Sequence
<220> FEATURE:
<223> OTHER INFORMATION: VH of 15H3L2 and 15H3L3

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Ile
 50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Met Tyr
                85                  90                  95

Tyr Cys Val Arg His Gly Asn Phe Gly Asn Ser Tyr Leu Ser Tyr Trp
            100                 105                 110

Ala Tyr Trp Gly Gln Gly Thr Leu Val Thr Val Ser Ser
            115                 120                 125

<210> SEQ ID NO 11
<211> LENGTH: 125
<212> TYPE: PRT
<213> ORGANISM: Artificial Sequence
<220> FEATURE:
<223> OTHER INFORMATION: VH of mouse and chimeric 19-26

<400> SEQUENCE: 11

Glu Val Lys Leu Leu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95
```

Tyr Cys Val Arg His Gly Asn Phe Gly Asn Ser Tyr Ile Ser Trp Trp
            100                 105                 110

Ala Tyr Trp Gly Gln Gly Thr Leu Val Thr Val Ser Ala
            115                 120                 125

<210> SEQ ID NO 12
<211> LENGTH: 125
<212> TYPE: PRT
<213> ORGANISM: Artificial Sequence
<220> FEATURE:
<223> OTHER INFORMATION: VH of 26-H2L3

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Lys His Gly Asn Phe Gly Asn Ser Tyr Ile Ser Trp Trp
            100                 105                 110

Ala Tyr Trp Gly Gln Gly Thr Leu Val Thr Val Ser Ser
            115                 120                 125

<210> SEQ ID NO 13
<211> LENGTH: 125
<212> TYPE: PRT
<213> ORGANISM: Artificial Sequence
<220> FEATURE:
<223> OTHER INFORMATION: VH of 26-H3L3

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Met Tyr
                85                  90                  95

Tyr Cys Val Arg His Gly Asn Phe Gly Asn Ser Tyr Ile Ser Trp Trp
            100                 105                 110

Ala Tyr Trp Gly Gln Gly Thr Leu Val Thr Val Ser Ser
            115                 120                 125

<210> SEQ ID NO 14
<211> LENGTH: 125
<212> TYPE: PRT
<213> ORGANISM: Artificial Sequence

```
<220> FEATURE:
<223> OTHER INFORMATION: VH of mouse and chimeric 19-37

<400> SEQUENCE: 14

Glu Val Lys Leu Leu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Ile
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ala
        115                 120                 125

<210> SEQ ID NO 15
<211> LENGTH: 109
<212> TYPE: PRT
<213> ORGANISM: Artificial Sequence
<220> FEATURE:
<223> OTHER INFORMATION: VL of mouse and chimeric CD3-19

<400> SEQUENCE: 15

Gln Ala Val Val Thr Gln Glu Ser Ala Leu Thr Thr Ser Pro Gly Glu
1               5                   10                  15

Thr Val Thr Leu Thr Cys Asp Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Gln Arg Ser Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Val Leu Trp Tyr Ser Asn
                85                  90                  95

Leu Trp Val Phe Gly Gly Gly Thr Lys Leu Thr Val Leu
            100                 105

<210> SEQ ID NO 16
<211> LENGTH: 109
<212> TYPE: PRT
<213> ORGANISM: Artificial Sequence
<220> FEATURE:
<223> OTHER INFORMATION: VL of mouse and chimeric 19-15

<400> SEQUENCE: 16

Gln Ala Val Val Thr Gln Glu Ser Ala Leu Thr Thr Ser Pro Gly Glu
1               5                   10                  15

Thr Val Thr Leu Thr Cys Gln Ser Ser Thr Gly Ala Val Thr Thr Asn
            20                  25                  30

Asn Tyr Ala Asn Trp Val Gln Glu Lys Pro Asp His Leu Phe Thr Gly
        35                  40                  45
```

Leu Ile Gly Gly Thr Lys Gln Arg Ala Pro Gly Val Pro Ala Arg Phe
            50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Val Leu Trp Tyr Ser Asn
                85                  90                  95

Leu Trp Val Phe Gly Gly Gly Thr Lys Leu Thr Val Leu
                100                 105

<210> SEQ ID NO 17
<211> LENGTH: 109
<212> TYPE: PRT
<213> ORGANISM: Artificial Sequence
<220> FEATURE:
<223> OTHER INFORMATION: VL of 15H2L2 and 15H3L2

<400> SEQUENCE: 17

Gln Thr Val Val Thr Gln Glu Pro Ser Leu Thr Val Ser Pro Gly Gly
1               5                   10                  15

Thr Val Thr Leu Thr Cys Gln Ser Ser Thr Gly Ala Val Thr Thr Asn
            20                  25                  30

Asn Tyr Ala Asn Trp Val Gln Gln Lys Pro Gly Gln Ala Pro Arg Ala
        35                  40                  45

Leu Ile Gly Gly Thr Lys Gln Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Leu Trp Val Phe Gly Gly Gly Thr Lys Leu Thr Val Leu
                100                 105

<210> SEQ ID NO 18
<211> LENGTH: 109
<212> TYPE: PRT
<213> ORGANISM: Artificial Sequence
<220> FEATURE:
<223> OTHER INFORMATION: VL of 15H2L3 and 15H3L3

<400> SEQUENCE: 18

Gln Ala Val Val Thr Gln Glu Pro Ser Leu Thr Val Ser Pro Gly Gly
1               5                   10                  15

Thr Val Thr Leu Thr Cys Gln Ser Ser Thr Gly Ala Val Thr Thr Asn
            20                  25                  30

Asn Tyr Ala Asn Trp Val Gln Gln Lys Pro Gly His Ala Phe Arg Gly
        35                  40                  45

Leu Ile Gly Gly Thr Lys Gln Arg Ala Pro Gly Val Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Leu Trp Val Phe Gly Gly Gly Thr Lys Leu Thr Val Leu
                100                 105

<210> SEQ ID NO 19
<211> LENGTH: 109
<212> TYPE: PRT
<213> ORGANISM: Artificial Sequence

```
<220> FEATURE:
<223> OTHER INFORMATION: VL of mouse and chimeric 19-26

<400> SEQUENCE: 19

Gln Ala Val Val Thr Gln Glu Ser Ala Leu Thr Thr Ser Pro Gly Glu
1               5                   10                  15

Thr Val Thr Leu Thr Cys Lys Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Leu His Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 20
<211> LENGTH: 109
<212> TYPE: PRT
<213> ORGANISM: Artificial Sequence
<220> FEATURE:
<223> OTHER INFORMATION: VL of 26-H2L3 and 26-H3L3

<400> SEQUENCE: 20

Gln Ala Val Val Thr Gln Glu Pro Ser Leu Thr Val Ser Pro Gly Gly
1               5                   10                  15

Thr Val Thr Leu Thr Cys Lys Ser Ser Thr Gly Ala Val Thr Thr Ser
            20                  25                  30

Asn Tyr Ala Asn Trp Val Gln Gln Lys Pro Gly His Ala Phe Arg Gly
        35                  40                  45

Leu Ile Gly Gly Thr Asn Leu His Ala Pro Gly Val Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 21
<211> LENGTH: 109
<212> TYPE: PRT
<213> ORGANISM: Artificial Sequence
<220> FEATURE:
<223> OTHER INFORMATION: VL of mouse and chimeric 19-37

<400> SEQUENCE: 21

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Asn
            20                  25                  30

Asn Tyr Ala Asn Trp Val Gln Glu Lys Pro Asp His Leu Phe Thr Gly
        35                  40                  45

Leu Ile Gly Gly Thr Arg Leu Ser Ala Pro Gly Val Pro Ala Arg Phe
    50                  55                  60
```

```
Ser Gly Ser Leu Ile Gly Asp Lys Ala Ala Leu Thr Ile Thr Gly Ala
 65                  70                  75                  80

Gln Thr Glu Asp Glu Ala Ile Tyr Phe Cys Val Leu Trp Tyr Ser Asn
                 85                  90                  95

Leu Trp Val Phe Gly Gly Gly Thr Lys Leu Thr Val Leu
            100                 105

<210> SEQ ID NO 22
<211> LENGTH: 330
<212> TYPE: PRT
<213> ORGANISM: Artificial Sequence
<220> FEATURE:
<223> OTHER INFORMATION: human IgG1 Fc-wildtype IgG1 Fc L234A/L235A IgG1
      Fc L234A/L235A/P329G IgG1 Fc L234A/L235A/N297A IgG1 Fc
      L234A/L235A/N297A/P329G
<220> FEATURE:
<221> NAME/KEY: misc_feature
<222> LOCATION: (117)..(117)
<223> OTHER INFORMATION: Xaa can be Leu or Ala
<220> FEATURE:
<221> NAME/KEY: misc_feature
<222> LOCATION: (118)..(118)
<223> OTHER INFORMATION: Xaa can be Leu or Ala
<220> FEATURE:
<221> NAME/KEY: misc_feature
<222> LOCATION: (180)..(180)
<223> OTHER INFORMATION: Xaa can be Asn or Ala
<220> FEATURE:
<221> NAME/KEY: misc_feature
<222> LOCATION: (212)..(212)
<223> OTHER INFORMATION: Xaa can be Pro or Gly

<400> SEQUENCE: 22

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Xaa Xaa Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Xaa Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Xaa Ala Pro Ile Glu Lys Thr Ile Ser Lys Ala Lys Gly
    210                 215                 220
```

```
Gln Pro Arg Glu Pro Gln Val Tyr Thr Leu Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 23
<211> LENGTH: 106
<212> TYPE: PRT
<213> ORGANISM: Artificial Sequence
<220> FEATURE:
<223> OTHER INFORMATION: human lambda light chain constant region

<400> SEQUENCE: 23

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 24
<211> LENGTH: 623
<212> TYPE: DNA
<213> ORGANISM: Artificial Sequence
<220> FEATURE:
<223> OTHER INFORMATION: human CD3 cDNA

<400> SEQUENCE: 24
atgcagtcgg gcactcactg gagagttctg ggcctctgcc tcttatcagt tggcgtttgg     60
gggcaagatg gtaatgaaga aatgggtggt attacacaga caccatataa agtctccatc    120
tctggaacca cagtaatatt gacatgccct cagtatcctg atctgaaat actatggcaa     180 cacaatgata aaaacatagg cggtgatgag gatgataaaa acataggcag tgatgaggat    240
cacctgtcac tgaaggaatt ttcagaattg agcaaagtg gttttatgtc tgctacccca    300
gaggaagcaa accagaagat gcgaactttt atctctacct gagggcaaga gtgtgtgaga    360
actgcatgga gatggatgtg atgtcggtgg ccacaattgt catagtggac atctgcatca    420 ctggggctt gctgctgctg gtttactact ggagcaagaa tagaaaggcc aaggccaagc    480
ctgtgacacg aggagcgggt gctggcggca ggcaaagggg acaaaacaag gagaggccac    540
```

```
cacctgttcc caacccagac tatgagccca tccggaaagg ccagcgggac ctgtattctg    600
gcctgaatca gagacgcatc tga                                            623
```

<210> SEQ ID NO 25
<211> LENGTH: 516
<212> TYPE: DNA
<213> ORGANISM: Artificial Sequence
<220> FEATURE:
<223> OTHER INFORMATION: human CD3 cDNA

<400> SEQUENCE: 25

```
atggaacata gcacgtttct ctctggcctg gtactggcta cccttctctc gcaagtgagc     60
cccttcaaga tacctataga ggaacttgag acagagtgt ttgtgaattg caataccagc    120
atcacatggg tagagggaac ggtgggaaca ctgctctcag acattacaag actggacctg    180
ggaaaacgca tcctggaccc acgaggaata tataggtgta atgggacaga tatatacaag    240
gacaaagaat ctaccgtgca agttcattat cgaatgtgcc agagctgtgt ggagctggat    300
ccagccaccg tggctggcat cattgtcact gatgtcattg ccactctgct ccttgctttg    360
ggagtcttct gctttgctgg acatgagact ggaaggctgt ctggggctgc cgacacacaa    420
gctctgttga ggaatgacca ggtctatcag cccctccgag atcgagatga tgctcagtac    480
agccaccttg gaggaaactg ggctcggaac aagtga                             516
```

<210> SEQ ID NO 26
<211> LENGTH: 119
<212> TYPE: PRT
<213> ORGANISM: Artificial Sequence
<220> FEATURE:
<223> OTHER INFORMATION: VH of MIL62

<400> SEQUENCE: 26

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115
```

<210> SEQ ID NO 27
<211> LENGTH: 112
<212> TYPE: PRT
<213> ORGANISM: Artificial Sequence
<220> FEATURE:
<223> OTHER INFORMATION: VL of MIL62

<400> SEQUENCE: 27

```
Asp Ile Val Met Thr Gln Thr Pro Leu Ser Leu Pro Val Thr Pro Gly
1               5                   10                  15
```

```
Glu Pro Ala Ser Ile Ser Cys Arg Ser Ser Lys Ser Leu His Ser
                20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110
```

<210> SEQ ID NO 28
<211> LENGTH: 15
<212> TYPE: PRT
<213> ORGANISM: Artificial Sequence
<220> FEATURE:
<223> OTHER INFORMATION: Linker

<400> SEQUENCE: 28

```
Gly Gly Gly Gly Ser Gly Gly Gly Gly Ser Gly Gly Gly Gly Ser
1               5                   10                  15
```

<210> SEQ ID NO 29
<211> LENGTH: 386
<212> TYPE: PRT
<213> ORGANISM: Artificial Sequence
<220> FEATURE:
<223> OTHER INFORMATION: MIL62 VH-linker-MIL62 VL-linker-15H2L3 VH

<400> SEQUENCE: 29

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
                20                  25                  30

Trp Ile Asn Trp Val Arg Gln Ala Pro Gly Gln Gly Leu Glu Trp Met
            35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Gly Gly Gly Gly Ser Gly Gly Gly Gly
            115                 120                 125

Ser Gly Gly Gly Gly Ser Asp Ile Val Met Thr Gln Thr Pro Leu Ser
        130                 135                 140

Leu Pro Val Thr Pro Gly Glu Pro Ala Ser Ile Ser Cys Arg Ser Ser
145                 150                 155                 160

Lys Ser Leu Leu His Ser Asn Gly Ile Thr Tyr Leu Tyr Trp Tyr Leu
                165                 170                 175

Gln Lys Pro Gly Gln Ser Pro Gln Leu Leu Ile Tyr Gln Met Ser Asn
            180                 185                 190

Leu Val Ser Gly Val Pro Asp Arg Phe Ser Gly Ser Gly Ser Gly Thr
```

```
              195                 200                 205
Asp Phe Thr Leu Lys Ile Ser Arg Val Glu Ala Glu Asp Val Gly Val
    210                 215                 220

Tyr Tyr Cys Ala Gln Asn Leu Glu Leu Pro Tyr Thr Phe Gly Gly Gly
225                 230                 235                 240

Thr Lys Val Glu Ile Lys Gly Gly Gly Ser Gly Gly Gly Gly Ser
                245                 250                 255

Gly Gly Gly Gly Ser Glu Val Gln Leu Leu Glu Ser Gly Gly Gly Leu
                260                 265                 270

Val Gln Pro Gly Gly Ser Leu Arg Leu Ser Cys Ala Ala Ser Gly Phe
            275                 280                 285

Thr Phe Asn Thr Tyr Ala Met Asn Trp Val Arg Gln Ala Pro Gly Lys
        290                 295                 300

Gly Leu Glu Trp Val Ala Arg Ile Arg Ser Lys Tyr Asn Asn Tyr Ala
305                 310                 315                 320

Thr Tyr Tyr Ala Ile Ser Val Lys Asp Arg Phe Thr Ile Ser Arg Asp
                325                 330                 335

Asn Ser Lys Asn Thr Leu Tyr Leu Gln Met Asn Ser Leu Arg Ala Glu
                340                 345                 350

Asp Thr Ala Val Tyr Tyr Cys Val Lys His Gly Asn Phe Gly Asn Ser
            355                 360                 365

Tyr Leu Ser Tyr Ala Tyr Trp Gly Gln Gly Thr Leu Val Thr Val
370                 375                 380

Ser Ser
385

<210> SEQ ID NO 30
<211> LENGTH: 386
<212> TYPE: PRT
<213> ORGANISM: Artificial Sequence
<220> FEATURE:
<223> OTHER INFORMATION: MIL62 VH-linker-MIL62 VL-linker-15H3L3 VH

<400> SEQUENCE: 30

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
                20                  25                  30

Trp Ile Asn Trp Val Arg Gln Ala Pro Gly Gln Gly Leu Glu Trp Met
            35                  40                  45

Gly Arg Ile Phe Pro Gly Asp Gly Asp Thr Asp Tyr Asn Gly Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
                100                 105                 110

Thr Leu Val Thr Val Ser Ser Gly Gly Gly Gly Ser Gly Gly Gly Gly
            115                 120                 125

Ser Gly Gly Gly Gly Ser Asp Ile Val Met Thr Gln Thr Pro Leu Ser
        130                 135                 140

Leu Pro Val Thr Pro Gly Glu Pro Ala Ser Ile Ser Cys Arg Ser Ser
145                 150                 155                 160

Lys Ser Leu Leu His Ser Asn Gly Ile Thr Tyr Leu Tyr Trp Tyr Leu
```

```
                    165                 170                 175
Gln Lys Pro Gly Gln Ser Pro Gln Leu Leu Ile Tyr Gln Met Ser Asn
            180                 185                 190

Leu Val Ser Gly Val Pro Asp Arg Phe Ser Gly Ser Gly Ser Gly Thr
            195                 200                 205

Asp Phe Thr Leu Lys Ile Ser Arg Val Glu Ala Glu Asp Val Gly Val
210                 215                 220

Tyr Tyr Cys Ala Gln Asn Leu Glu Leu Pro Tyr Thr Phe Gly Gly Gly
225                 230                 235                 240

Thr Lys Val Glu Ile Lys Gly Gly Gly Ser Gly Gly Gly Gly Ser
            245                 250                 255

Gly Gly Gly Gly Ser Glu Val Gln Leu Leu Glu Ser Gly Gly Gly Leu
            260                 265                 270

Val Gln Pro Gly Gly Ser Leu Arg Leu Ser Cys Ala Ala Ser Gly Phe
            275                 280                 285

Thr Phe Asn Thr Tyr Ala Met Asn Trp Val Arg Gln Ala Pro Gly Lys
            290                 295                 300

Gly Leu Glu Trp Val Ala Arg Ile Arg Ser Lys Tyr Asn Asn Tyr Ala
305                 310                 315                 320

Thr Tyr Tyr Ala Ile Ser Val Lys Asp Arg Phe Thr Ile Ser Arg Asp
                325                 330                 335

Asp Ser Lys Asn Thr Leu Tyr Leu Gln Met Asn Ser Leu Arg Ala Glu
            340                 345                 350

Asp Thr Ala Met Tyr Tyr Cys Val Arg His Gly Asn Phe Gly Asn Ser
            355                 360                 365

Tyr Leu Ser Tyr Trp Ala Tyr Trp Gly Gln Gly Thr Leu Val Thr Val
            370                 375                 380

Ser Ser
385

<210> SEQ ID NO 31
<211> LENGTH: 107
<212> TYPE: PRT
<213> ORGANISM: Artificial Sequence
<220> FEATURE:
<223> OTHER INFORMATION: Light chain constant region of MIL220 and MIL62

<400> SEQUENCE: 31

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 32
<211> LENGTH: 103
<212> TYPE: PRT
```

<213> ORGANISM: Artificial Sequence
<220> FEATURE:
<223> OTHER INFORMATION: Light chain constant region of MIL221-1 and MIL221-2

<400> SEQUENCE: 32

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr
            100
```

<210> SEQ ID NO 33
<211> LENGTH: 330
<212> TYPE: PRT
<213> ORGANISM: Artificial Sequence
<220> FEATURE:
<223> OTHER INFORMATION: Heavy chain constant region of MIL220

<400> SEQUENCE: 33

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

```
Gln Pro Arg Glu Pro Gln Val Tyr Thr Leu Pro Pro Ser Arg Glu Glu
225                 230                 235                 240

Met Thr Lys Asn Gln Val Ser Leu Ser Cys Ala Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Val Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 34
<211> LENGTH: 330
<212> TYPE: PRT
<213> ORGANISM: Artificial Sequence
<220> FEATURE:
<223> OTHER INFORMATION: Heavy chain constant region of MIL221-1 and
      221-2

<400> SEQUENCE: 34

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Trp Cys Leu Val Lys Gly Phe Tyr
```

```
                        245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
            275                 280                 285
Leu Tyr Ser Lys Leu Thr Val Asp Lys Ser Arg Trp Gln Gln Gly Asn
        290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 35
<211> LENGTH: 297
<212> TYPE: PRT
<213> ORGANISM: Homo sapiens

<400> SEQUENCE: 35

Met Thr Thr Pro Arg Asn Ser Val Asn Gly Thr Phe Pro Ala Glu Pro
1               5                   10                  15
Met Lys Gly Pro Ile Ala Met Gln Ser Gly Pro Lys Pro Leu Phe Arg
            20                  25                  30
Arg Met Ser Ser Leu Val Gly Pro Thr Gln Ser Phe Phe Met Arg Glu
        35                  40                  45
Ser Lys Thr Leu Gly Ala Val Gln Ile Met Asn Gly Leu Phe His Ile
    50                  55                  60
Ala Leu Gly Gly Leu Leu Met Ile Pro Ala Gly Ile Tyr Ala Pro Ile
65                  70                  75                  80
Cys Val Thr Val Trp Tyr Pro Leu Trp Gly Gly Ile Met Tyr Ile Ile
                85                  90                  95
Ser Gly Ser Leu Leu Ala Ala Thr Glu Lys Asn Ser Arg Lys Cys Leu
            100                 105                 110
Val Lys Gly Lys Met Ile Met Asn Ser Leu Ser Leu Phe Ala Ala Ile
        115                 120                 125
Ser Gly Met Ile Leu Ser Ile Met Asp Ile Leu Asn Ile Lys Ile Ser
    130                 135                 140
His Phe Leu Lys Met Glu Ser Leu Asn Phe Ile Arg Ala His Thr Pro
145                 150                 155                 160
Tyr Ile Asn Ile Tyr Asn Cys Glu Pro Ala Asn Pro Ser Glu Lys Asn
                165                 170                 175
Ser Pro Ser Thr Gln Tyr Cys Tyr Ser Ile Gln Ser Leu Phe Leu Gly
            180                 185                 190
Ile Leu Ser Val Met Leu Ile Phe Ala Phe Phe Gln Glu Leu Val Ile
        195                 200                 205
Ala Gly Ile Val Glu Asn Glu Trp Lys Arg Thr Cys Ser Arg Pro Lys
    210                 215                 220
Ser Asn Ile Val Leu Leu Ser Ala Glu Glu Lys Lys Glu Gln Thr Ile
225                 230                 235                 240
Glu Ile Lys Glu Glu Val Val Gly Leu Thr Glu Thr Ser Ser Gln Pro
                245                 250                 255
Lys Asn Glu Glu Asp Ile Glu Ile Ile Pro Ile Gln Glu Glu Glu Glu
            260                 265                 270
Glu Glu Thr Glu Thr Asn Phe Pro Glu Pro Pro Gln Asp Gln Glu Ser
        275                 280                 285
```

Ser Pro Ile Glu Asn Asp Ser Ser Pro
    290                 295

<210> SEQ ID NO 36
<211> LENGTH: 297
<212> TYPE: PRT
<213> ORGANISM: macaca fascicularis

<400> SEQUENCE: 36

Met Thr Thr Pro Arg Asn Ser Val Asn Gly Thr Phe Pro Ala Glu Pro
1               5                   10                  15

Met Lys Gly Pro Ile Ala Met Gln Pro Gly Pro Lys Pro Leu Leu Arg
            20                  25                  30

Arg Met Ser Ser Leu Val Gly Pro Thr Gln Ser Phe Phe Met Arg Glu
        35                  40                  45

Ser Lys Ala Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Val His Thr Pro
145                 150                 155                 160

Tyr Ile Asn Ile Tyr Tyr Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Arg Arg Thr Cys Ser Arg Pro Lys
    210                 215                 220

Ser Ser Val Val Leu Leu Ser Ala Glu Glu Lys Lys Glu Gln Val Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Pro Ile Gln Glu Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295

<210> SEQ ID NO 37
<211> LENGTH: 254
<212> TYPE: PRT
<213> ORGANISM: Homo sapiens

<400> SEQUENCE: 37

Met Trp Gln Leu Leu Leu Pro Thr Ala Leu Leu Leu Leu Val Ser Ala
1               5                   10                  15

```
Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 38
<211> LENGTH: 317
<212> TYPE: PRT
<213> ORGANISM: Homo sapiens

<400> SEQUENCE: 38

Met Thr Met Glu Thr Gln Met Ser Gln Asn Val Cys Pro Arg Asn Leu
1               5                   10                  15

Trp Leu Leu Gln Pro Leu Thr Val Leu Leu Leu Leu Ala Ser Ala Asp
            20                  25                  30

Ser Gln Ala Ala Ala Pro Pro Lys Ala Val Leu Lys Leu Glu Pro Pro
        35                  40                  45

Trp Ile Asn Val Leu Gln Glu Asp Ser Val Thr Leu Thr Cys Gln Gly
50                  55                  60

Ala Arg Ser Pro Glu Ser Asp Ser Ile Gln Trp Phe His Asn Gly Asn
65                  70                  75                  80

Leu Ile Pro Thr His Thr Gln Pro Ser Tyr Arg Phe Lys Ala Asn Asn
                85                  90                  95

Asn Asp Ser Gly Glu Tyr Thr Cys Gln Thr Gly Gln Thr Ser Leu Ser
            100                 105                 110

Asp Pro Val His Leu Thr Val Leu Ser Glu Trp Leu Val Leu Gln Thr
        115                 120                 125

Pro His Leu Glu Phe Gln Glu Gly Glu Thr Ile Met Leu Arg Cys His
130                 135                 140
```

```
Ser Trp Lys Asp Lys Pro Leu Val Lys Val Thr Phe Phe Gln Asn Gly
145                 150                 155                 160

Lys Ser Gln Lys Phe Ser His Leu Asp Pro Thr Phe Ser Ile Pro Gln
                165                 170                 175

Ala Asn His Ser His Ser Gly Asp Tyr His Cys Thr Gly Asn Ile Gly
            180                 185                 190

Tyr Thr Leu Phe Ser Ser Lys Pro Val Thr Ile Thr Val Gln Val Pro
        195                 200                 205

Ser Met Gly Ser Ser Ser Pro Met Gly Ile Ile Val Ala Val Val Ile
210                 215                 220

Ala Thr Ala Val Ala Ala Ile Val Ala Ala Val Val Ala Leu Ile Tyr
225                 230                 235                 240

Cys Arg Lys Lys Arg Ile Ser Ala Asn Ser Thr Asp Pro Val Lys Ala
                245                 250                 255

Ala Gln Phe Glu Pro Pro Gly Arg Gln Met Ile Ala Ile Arg Lys Arg
            260                 265                 270

Gln Leu Glu Glu Thr Asn Asn Asp Tyr Glu Thr Ala Asp Gly Gly Tyr
        275                 280                 285

Met Thr Leu Asn Pro Arg Ala Pro Thr Asp Asp Lys Asn Ile Tyr
290                 295                 300

Leu Thr Leu Pro Pro Asn Asp His Val Asn Ser Asn
305                 310                 315

<210> SEQ ID NO 39
<211> LENGTH: 310
<212> TYPE: PRT
<213> ORGANISM: Homo sapiens

<400> SEQUENCE: 39

Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
            20                  25                  30

Ala Val Leu Phe Leu Ala Pro Val Ala Gly Thr Pro Ala Ala Pro Pro
        35                  40                  45

Lys Ala Val Leu Lys Leu Glu Pro Gln Trp Ile Asn Val Leu Gln Glu
    50                  55                  60

Asp Ser Val Thr Leu Thr Cys Arg Gly Thr His Ser Pro Glu Ser Asp
65                  70                  75                  80

Ser Ile Gln Trp Phe His Asn Gly Asn Leu Ile Pro Thr His Thr Gln
                85                  90                  95

Pro Ser Tyr Arg Phe Lys Ala Asn Asn Asn Asp Ser Gly Glu Tyr Thr
            100                 105                 110

Cys Gln Thr Gly Gln Thr Ser Leu Ser Asp Pro Val His Leu Thr Val
        115                 120                 125

Leu Ser Glu Trp Leu Val Leu Gln Thr Pro His Leu Glu Phe Gln Glu
    130                 135                 140

Gly Glu Thr Ile Val Leu Arg Cys His Ser Trp Lys Asp Lys Pro Leu
145                 150                 155                 160

Val Lys Val Thr Phe Phe Gln Asn Gly Lys Ser Lys Lys Phe Ser Arg
                165                 170                 175

Ser Asp Pro Asn Phe Ser Ile Pro Gln Ala Asn His Ser His Ser Gly
            180                 185                 190

Asp Tyr His Cys Thr Gly Asn Ile Gly Tyr Thr Leu Tyr Ser Ser Lys
```

-continued

```
                195                 200                 205
Pro Val Thr Ile Thr Val Gln Ala Pro Ser Ser Pro Met Gly Ile
            210                 215                 220

Ile Val Ala Val Val Thr Gly Ile Ala Val Ala Ile Val Ala Ala
225                 230                 235                 240

Val Val Ala Leu Ile Tyr Cys Arg Lys Lys Arg Ile Ser Ala Leu Pro
                245                 250                 255

Gly Tyr Pro Glu Cys Arg Glu Met Gly Glu Thr Leu Pro Glu Lys Pro
                260                 265                 270

Ala Asn Pro Thr Asn Pro Asp Glu Ala Asp Lys Val Gly Ala Glu Asn
                275                 280                 285

Thr Ile Thr Tyr Ser Leu Leu Met His Pro Asp Ala Leu Glu Glu Pro
            290                 295                 300

Asp Asp Gln Asn Arg Ile
305                 310

<210> SEQ ID NO 40
<211> LENGTH: 374
<212> TYPE: PRT
<213> ORGANISM: Homo sapiens

<400> SEQUENCE: 40

Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
                20                  25                  30

Val Phe Gln Glu Glu Thr Val Thr Leu His Cys Glu Val Leu His Leu
            35                  40                  45

Pro Gly Ser Ser Thr Gln Trp Phe Leu Asn Gly Thr Ala Thr Gln
        50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255
```

```
Leu Tyr Trp Cys Glu Ala Ala Thr Glu Asp Gly Asn Val Leu Lys Arg
            260             265             270

Ser Pro Glu Leu Glu Leu Gln Val Leu Gly Leu Gln Leu Pro Thr Pro
        275             280             285

Val Trp Phe His Val Leu Phe Tyr Leu Ala Val Gly Ile Met Phe Leu
    290             295             300

Val Asn Thr Val Leu Trp Val Thr Ile Arg Lys Glu Leu Lys Arg Lys
305             310             315             320

Lys Lys Trp Asp Leu Glu Ile Ser Leu Asp Ser Gly His Glu Lys Lys
            325             330             335

Val Ile Ser Ser Leu Gln Glu Asp Arg His Leu Glu Glu Glu Leu Lys
            340             345             350

Cys Gln Glu Gln Lys Glu Glu Gln Leu Gln Glu Gly Val His Arg Lys
            355             360             365

Glu Pro Gln Gly Ala Thr
    370
```